(12) United States Patent
Aebi et al.

(10) Patent No.: US 9,353,081 B2
(45) Date of Patent: May 31, 2016

(54) BICYCLIC DIHYDROQUINOLINE-2-ONE DERIVATIVES

(75) Inventors: Johannes Aebi, Binningen (CH); Kurt Amrein, Itingen (CH); Serena Maria Fantasia, Basel (CH); Benoit Hornsperger, Altkirch (FR); Bernd Kuhn, Reinach BL (CH); Yongfu Liu, Shanghai (CN); Hans P. Maerki, Basel (CH); Alexander V. Mayweg, Shanghai (CN); Peter Mohr, Basel (CH); Michelangelo Scalone, Birsfelden (CH); Xuefei Tan, Shanghai (CN); Mingwei Zhou, Shanghai (CN)

(73) Assignee: Hoffmann-La Roche Inc., Nutley, NJ (US)

(*) Notice: Subject to any disclaimer, the term of this patent is extended or adjusted under 35 U.S.C. 154(b) by 143 days.

(21) Appl. No.: 13/615,901

(22) Filed: Sep. 14, 2012

(65) Prior Publication Data

US 2013/0079365 A1    Mar. 28, 2013

(30) Foreign Application Priority Data

Sep. 23, 2011 (WO) ................ PCT/CN2011/080078

(51) Int. Cl.
  C07D 471/02 (2006.01)
  C07D 401/04 (2006.01)
  C07D 471/04 (2006.01)

(52) U.S. Cl.
  CPC ............ C07D 401/04 (2013.01); C07D 471/04 (2013.01)

(58) Field of Classification Search
  USPC ................................. 514/183, 300
  See application file for complete search history.

(56) References Cited

U.S. PATENT DOCUMENTS 4,898,872 A    2/1990   Campbell et al.
2007/0249605 A1   10/2007   Allen et al.

FOREIGN PATENT DOCUMENTS

WO    2009/135651    12/2009

OTHER PUBLICATIONS

International Search Report for PCT/EP2012/068472 dated Oct. 30, 2012.
Lucas et al., "In Vivo Active Aldosterone Synthase Inhibitors with Improved Selectivity: Lead Optimization Providing a Series of Pyridine Substituted 3,4-Dihydro-1H-quinolin-2-one Derivatives," J. Med. Chem. 2008, 51, 8077-8087.
The English translation of the Colombian Office Action, issued on Feb. 24, 2015, in the corresponding Colombian Application No. 14-020.664.
The English translation of the Japanese Office Action, issued on Jan. 6, 2015, in the corresponding Japanese Application No. 2014-531214.

*Primary Examiner* — Shobha Kantamneni

(57) ABSTRACT

The invention provides novel compounds having the general formula (I)

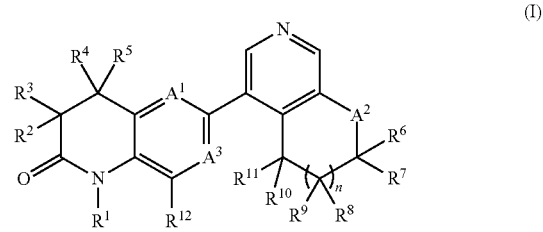

wherein $R^1, R^2, R^3, R^4, R^5, R^6, R^7, R^8, R^9, R^{10}, R^{11}, R^{12}, A^1, A^2, A^3$ and n are as described herein, compositions including the compounds and methods of using the compounds.

The compounds of the present invention are useful as inhibitors of aldosterone synthase. The compounds may be used, for example, in the treatment or prophylaxis of chronic kidney disease, congestive heart failure, hypertension, primary aldosteronism and Cushing syndrome.

21 Claims, No Drawings

BICYCLIC DIHYDROQUINOLINE-2-ONE DERIVATIVES

PRIORITY TO RELATED APPLICATION(S)

This application claims the benefit of International Patent Application No. PCT/CN2011/080078, filed Sep. 23, 2011, which is hereby incorporated by reference in its entirety.

FIELD OF THE INVENTION

The present invention relates to organic compounds useful for therapy or prophylaxis in a mammal, and in particular to aldosterone synthase (CYP11B2 or CYP11B1) inhibitors for the treatment or prophylaxis of chronic kidney disease, congestive heart failure, hypertension, primary aldosteronism and Cushing syndrome.

BACKGROUND OF THE INVENTION

Herein we describe inhibitors of aldosterone synthase that have the potential to protect from organ/tissue damage caused by an absolute or relative excess of aldosterone. Hypertension affects about 20% of the adult population in developed countries. In persons 60 years and older, this percentage increases to above 60%. Hypertensive subjects display an increased risk of other physiological complications including stroke, myocardial infarction, atrial fibrillation, heart failure, peripheral vascular disease and renal impairment. The renin angiotensin aldosterone system is a pathway that has been linked to hypertension, volume and salt balance and more recently to contribute directly to end organ damage in advanced stages of heart failure or kidney disease. ACE inhibitors and angiotensin receptor blockers (ARBs) are successfully used to improve duration and quality of life of patients. These drugs are not yielding maximum protection. In a relatively large number of patients ACE and ARB's lead to so-called aldosterone breakthrough, a phenomenon where aldosterone levels, after a first initial decline, return to pathological levels. It has been demonstrated that the deleterious consequences of inappropriately increased aldosterone levels (in relation to salt intake/levels) can be minimized by aldosterone blockade with mineralocorticoid receptor antagonists. A direct inhibition of aldosterone synthesis is expected to provide even better protection as it will also reduce non-genomic effects of aldosterone as well.

The effects of aldosterone on Na/K transport lead to increased re-absorption of sodium and water and the secretion of potassium in the kidneys. Overall this results in increased blood volume and, therefore, increased blood pressure. Beyond its role in the regulation of renal sodium re-absorption aldosterone can exert deleterious effects on the kidney, the heart and the vascular system especially in a "high sodium" context. It has been shown that under such conditions aldosterone leads to increased oxidative stress which ultimately may contribute to organ damage. Infusion of aldosterone into renally compromised rats (either by high salt treatment or by unilaterally nephrectomy) induces a wide array of injuries to the kidney including glomerular expansion, podocyte injury, interstitial inflammation, mesangial cell proliferation and fibrosis reflected by proteinuria. More specifically aldosterone was shown to increase the expression of the adhesion molecule ICAM-1 in the kidney. ICAM-1 is critically involved in glomerular inflammation. Similarly, aldosterone was shown to increase the expression of inflammatory cytokines, such as interleukin IL-1b and IL-6, MCP-1 and osteopontin. On a cellular level it was demonstrated that in vascular fibroblasts aldosterone increased the expression of type I collagen mRNA, a mediator of fibrosis. Aldosterone also stimulates type IV collagen accumulation in rat mesangial cells and induces plasminogen activator inhibitor-1 (PAI-1) expression in smooth muscle cells. In summary aldosterone has emerged as a key hormone involved in renal damage. Aldosterone plays an equally important role in mediating cardiovascular risk.

There is ample preclinical evidence that MR-antagonists (spironolactone and eplerenone) improve blood pressure, cardiac and renal function in various pre-clinical models.

More recently preclinical studies highlight the important contribution of CYP11B2 to cardiovascular and renal morbidity and mortality. The CYP11B2 inhibitor FAD286 and the MR antagonist spironolactone were evaluated in a rat model of chronic kidney disease (high angiotensin II exposure; high salt and uni-nephrectomy). Angiotensin II and high salt treatment caused albuminuria, azotemia, renovascular hypertrophy, glomerular injury, increased PAI-1, and osteopontin mRNA expression, as well as tubulointerstitial fibrosis. Both drugs prevented these renal effects and attenuated cardiac and aortic medial hypertrophy. Following 4 weeks of treatment with FAD286, plasma aldosterone was reduced, whereas spironolactone increased aldosterone at 4 and 8 weeks of treatment. Similarly only spironolactone but not FAD286 enhanced angiotensin II and salt-stimulated PAI-1 mRNA expression in the aorta and the heart. In other studies the CYP11B2 inhibitor FAD286 improved blood pressure and cardiovascular function and structure in rats with experimental heart failure. In the same studies FAD286 was shown to improve kidney function and morphology.

Administration of an orally active CYP11B2 inhibitor, LCI699, to patients with primary aldosteronism, lead to the conclusion that it effectively inhibits CYP11B2 in patients with primary aldosteronism resulting in significantly lower circulating aldosterone levels and that it corrected the hypokalemia and mildly decreased blood pressure. The effects on the glucocorticoid axis were consistent with a poor selectivity of the compound and a latent inhibition of cortisol synthesis. Taken together these data support the concept that a CYP11B2 inhibitor can lower inappropriately high aldosterone levels. Achieving good selectivity against CYP11B1 is important to be free of undesired side effects on the HPA axis and will differentiate different CYP11B2 inhibitors.

Objects of the present invention are the compounds of formula (I) and their aforementioned salts and esters and their use as therapeutically active substances, a process for the manufacture of the said compounds, intermediates, pharmaceutical compositions, medicaments containing the said compounds, their pharmaceutically acceptable salts or esters, the use of the said compounds, salts or esters for the treatment or prophylaxis of illnesses, especially in the treatment or prophylaxis of chronic kidney disease, congestive heart failure, hypertension, primary aldosteronism and Cushing syndrome and the use of the said compounds, salts or esters for the production of medicaments for the treatment or prophylaxis of chronic kidney disease, congestive heart failure, hypertension, primary aldosteronism and Cushing syndrome.

The term "alkoxy" denotes a group of the formula —O—R', wherein R' is an alkyl group. Examples of alkoxy group include methoxy, ethoxy, n-propoxy, isopropoxy, n-butoxy, isobutoxy and tert-butoxy. Particular alkoxy group include methoxy, ethoxy and tert-butoxy. The term "alkoxyalkoxy" denotes an alkoxy group wherein at least one of the hydrogen atoms of the alkoxy group has been replaced by another alkoxy group. Examples of alkoxyalkoxy group include methoxymethoxy, ethoxymethoxy, methoxyethoxy, ethoxyethoxy, methoxypropoxy and ethoxypropoxy. Particular alkoxyalkoxy groups include methoxymethoxy and methoxyethoxy.

SUMMARY OF THE INVENTION

The present invention relates to a compound according to formula (I),

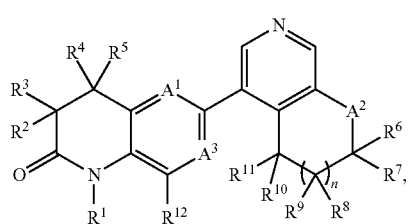

(I)

wherein
$R^1$ is selected from the group consisting of H, alkyl, haloalkyl, cycloalkyl and halocycloalkyl;
$R^2$ is selected from the group consisting of H, alkyl, haloalkyl, cycloalkyl and halocycloalkyl;
$R^3$ is selected from the group consisting of H, alkyl, haloalkyl, cycloalkyl and halocycloalkyl;
$R^4$ is selected from the group consisting of H, alkyl, haloalkyl, cycloalkyl and halocycloalkyl;
$R^5$ is selected from the group consisting of H, alkyl, haloalkyl, cycloalkyl and halocycloalkyl;
$R^6$ is selected from the group consisting of H, alkyl, haloalkyl, cycloalkyl and halocycloalkyl;
$R^7$ is selected from the group consisting of H, alkyl, haloalkyl, cycloalkyl and halocycloalkyl;
$R^8$ is selected from the group consisting of H, alkyl, haloalkyl, cycloalkyl and halocycloalkyl;
$R^9$ is selected from the group consisting of H, alkyl, haloalkyl, cycloalkyl and halocycloalkyl;
$R^{10}$ is selected from the group consisting of H, alkyl, haloalkyl, cycloalkyl and halocycloalkyl;
$R^{11}$ is selected from the group consisting of H, alkyl, haloalkyl, cycloalkyl and halocycloalkyl;
$R^{12}$ is selected from the group consisting of H, halogen, alkyl, haloalkyl, cycloalkyl and halocycloalkyl;
$A^1$ is N or $CR^{13}$;
$A^2$ is $NR^{14}$ or $CR^{15}R^{16}$;
$A^3$ is N or $CR^{17}$;
$R^{13}$ is selected from the group consisting of H, halogen, alkyl, haloalkyl, cycloalkyl and halocycloalkyl;
$R^{14}$ is selected from the group consisting of $-S(O)_2R^{18}$, $-S(O)_2OR^{18}$, $-S(O)_2NR^{18}R^{19}$, $-C(O)R^{18}$, $-C(O)OR^{18}$, $-C(O)NR^{18}R^{19}$ and $-(CR^{20}R^{21})_q-(CR^{22}R^{23})_r-(CR^{24}R^{25})_p-NR^{26}R^{27}$, wherein the sum of q, r and p is at least 2;
$R^{15}$ is $-(CR^{20}R^{21})_q-(CR^{22}R^{23})_r-(CR^{24}R^{25})_p-NR^{26}R^{27}$;
$R^{16}$ is selected from the group consisting of H, alkyl, haloalkyl, cycloalkyl and halocycloalkyl;
or $R^6$ and $R^{16}$ together with the carbon atoms to which they are attached form a double bond;
$R^{17}$ is selected from the group consisting of H, halogen, alkyl, haloalkyl, cycloalkyl and halocycloalkyl;
$R^{18}$ is selected from the group consisting of cycloalkyl, alkylcycloalkyl, halocycloalkyl, alkylcycloalkylalkyl, halocycloalkylalkyl, cycloalkylalkyl, cycloalkoxyalkyl, cycloalkylalkoxyalkyl, triazolylalkyl, tetrazolylalkyl, aminoalkyl, substituted aminoalkyl, substituted aryl, substituted heterocycloalkyl and substituted heteroaryl, wherein said substituted aminoalkyl is substituted on the nitrogen atom with one to two substituents independently selected from the group consisting of alkyl, cycloalkyl, alkylcycloalkyl, cycloalkylalkyl, alkylcycloalkylalkyl, hydroxyalkyl and alkoxyalkyl, and wherein said substituted aryl, substituted heterocycloalkyl and substituted heteroaryl are substituted with $R^{28}$, $R^{29}$ and $R^{30}$;
$R^{19}$ is selected from the group consisting of H, alkyl, haloalkyl, cycloalkyl, halocycloalkyl, alkoxyalkyl, haloalkoxyalkyl and hydroxyalkyl;
or $R^{18}$ and $R^{19}$ together with the nitrogen atom to which they are attached form a substituted heterocycloalkyl or a substituted heteroaryl, wherein said substituted heterocycloalkyl and substituted heteroaryl are substituted with $R^{28}$, $R^{29}$ and $R^{30}$;
$R^{20}$ is selected from the group consisting of H, alkyl, haloalkyl, cycloalkyl and halocycloalkyl;
$R^{21}$ is selected from the group consisting of H, alkyl, haloalkyl, cycloalkyl and halocycloalkyl;
$R^{22}$ is selected from the group consisting of H, alkyl, haloalkyl, cycloalkyl and halocycloalkyl;
$R^{23}$ is selected from the group consisting of H, alkyl, haloalkyl, cycloalkyl and halocycloalkyl;
or $R^{22}$ and $R^{23}$ together with the carbon atom to which they are attached form a cycloalkyl;
$R^{24}$ is selected from the group consisting of H, alkyl, haloalkyl, cycloalkyl and halocycloalkyl;
$R^{25}$ is selected from the group consisting of H, alkyl, haloalkyl, cycloalkyl and halocycloalkyl; or $R^{21}$ and $R^{25}$ together form $-(CH_2)_t-$;
$R^{26}$ is selected from the group consisting of H, alkyl, haloalkyl, cycloalkyl, halocycloalkyl, alkoxyalkyl, haloalkoxyalkyl and hydroxyalkyl;
$R^{27}$ is selected from the group consisting of H, alkyl, haloalkyl, cycloalkyl, halocycloalkyl, hydroxyalkyl, alkoxyalkyl, haloalkoxyalkyl, phenylalkyl, substituted phenylalkyl, substituted aryl, heterocycloalkyl, substituted heterocycloalkyl, substituted heteroaryl, $-S(O)_2R^{31}$, $-S(O)_2OR^{31}$, $-S(O)_2NR^{31}R^{32}$, $-C(O)R^{31}$, $-C(O)OR^{31}$ and $-C(O)NR^{31}R^{32}$, wherein said substituted phenylalkyl, substituted aryl, substituted heterocycloalkyl and substituted heteroaryl are substituted with $R^{28}$, $R^{29}$ and $R^{30}$, wherein in case $R^{26}$ is H or alkyl and $R^{27}$ is H or alkyl, then the sum of q, r and p is at least 1;
or $R^{26}$ and $R^{27}$ together with the nitrogen atom to which they are attached form a substituted heterocycloalkyl or a substituted heteroaryl, wherein said substituted heterocycloalkyl and substituted heteroaryl are substituted with $R^{28}$, $R^{29}$ and $R^{30}$;
or $R^{25}$ and $R^{26}$ together with the nitrogen atom to which they are attached form a substituted heterocycloalkyl or a substituted heteroaryl, wherein said substituted heterocycloalkyl and substituted heteroaryl are substituted with $R^{28}$, $R^{29}$ and $R^{30}$;
or $R^{23}$ and $R^{26}$ together with the nitrogen atom to which they are attached form a substituted heterocycloalkyl or a substituted heteroaryl, wherein said substituted heterocycloalkyl and substituted heteroaryl are substituted with $R^{28}$, $R^{29}$ and $R^{30}$;
or $R^{21}$ and $R^{26}$ together with the nitrogen atom to which they are attached form a substituted heterocycloalkyl or a substituted heteroaryl, wherein said substituted heterocycloalkyl and substituted heteroaryl are substituted with $R^{28}$, $R^{29}$ and $R^{30}$;

$R^{28}$, $R^{29}$ and $R^{30}$ are each independently selected from the group consisting of H, alkyl, hydroxyalkyl, haloalkyl, cycloalkyl, alkylcycloalkyl, halocycloalkyl, alkylcycloalkylalkyl, halocycloalkylalkyl, cycloalkylalkyl, cycloalkylalkoxy, cycloalkoxy, cycloalkoxyalkyl, cycloalkylalkoxyalkyl, alkoxy, alkoxyalkyl, haloalkoxy, haloalkoxyalkyl, alkoxyalkoxy, alkoxyalkoxyalkyl, alkoxycarbonyl, halogen, hydroxy, oxo, cyano, triazolylalkyl, tetrazolylalkyl, amino, substituted amino, aminoalkyl, substituted aminoalkyl, aminocarbonyl, substituted aminocarbonyl, alkylcarbonylamino, cycloalkylcarbonylamino, alkylcarbonylaminoalkyl and cycloalkylcarbonylaminoalkyl, wherein said substituted amino, substituted aminoalkyl and substituted aminocarbonyl are substituted on the nitrogen atom with one to two substituents independently selected from the group consisting of alkyl, cycloalkyl, alkylcycloalkyl, cycloalkylalkyl, alkylcycloalkylalkyl, hydroxyalkyl and alkoxyalkyl;

wherein in case $R^{14}$ is —S(O)$_2$$R^{18}$ or in case $R^{26}$ and $R^{27}$ or $R^{21}$ and $R^{26}$ or $R^{23}$ and $R^{26}$ or $R^{25}$ and $R^{26}$ together with the nitrogen atom to which they are attached form a substituted heterocycloalkyl or a substituted heteroaryl, then at least one of $R^{27}$, $R^{28}$, $R^{29}$ and $R^{30}$ is different from H, alkyl, haloalkyl, alkoxy, haloalkoxy, halogen, hydroxy, cyano, amino, substituted amino, aminocarbonyl or substituted aminocarbonyl, wherein substituted amino and substituted aminocarbonyl are substituted on the nitrogen atom with one to two alkyl;

$R^{31}$ is selected from the group consisting of H, alkyl, hydroxyalkyl, haloalkyl, cycloalkyl, alkylcycloalkyl, halocycloalkyl, alkylcycloalkylalkyl, halocycloalkylalkyl, cycloalkylalkyl, cycloalkoxyalkyl, cycloalkylalkoxyalkyl, alkoxyalkyl, haloalkoxyalkyl, alkoxyalkoxyalkyl, triazolylalkyl, tetrazolylalkyl, aminoalkyl, substituted aminoalkyl, substituted aryl, substituted heterocycloalkyl and substituted heteroaryl, wherein said substituted aminoalkyl is substituted on the nitrogen atom with one to two substituents independently selected from the group consisting of alkyl, cycloalkyl, alkylcycloalkyl, cycloalkylalkyl, alkylcycloalkylalkyl, hydroxyalkyl and alkoxyalkyl, and wherein said substituted aryl, substituted heterocycloalkyl and substituted heteroaryl are substituted with $R^{28}$, $R^{29}$ and $R^{30}$;

$R^{32}$ is selected from the group consisting of H, alkyl, haloalkyl, cycloalkyl, halocycloalkyl, alkoxyalkyl, haloalkoxyalkyl and hydroxyalkyl;

n is zero, 1 or 2;

P is zero, 1 or 2;

q is zero, 1 or 2;

r is zero, 1 or 2; and t is zero, 1, 2 or 3;

or a pharmaceutically acceptable salt or ester thereof.

The present invention relates also to a pharmaceutical composition comprising a compound as described above and a therapeutically inert carrier.

DETAILED DESCRIPTION OF THE INVENTION

The term "alkoxyalkoxyalkyl" denotes an alkyl group wherein at least one of the hydrogen atoms of the alkyl group has been replaced by an alkoxyalkoxy group. Examples of alkoxyalkoxyalkyl group include methoxymethoxymethyl, ethoxymethoxymethyl, methoxyethoxymethyl, ethoxyethoxymethyl, methoxypropoxymethyl, ethoxypropoxymethyl, methoxymethoxyethyl, ethoxymethoxyethyl, methoxyethoxyethyl, ethoxyethoxyethyl, methoxypropoxyethyl and ethoxypropoxyethyl.

The term "alkoxyalkyl" denotes an alkyl group wherein at least one of the hydrogen atoms of the alkyl group has been replaced by an alkoxy group. Exemplary alkoxyalkyl groups include methoxymethyl, ethoxymethyl, methoxymethyl, ethoxyethyl, methoxypropyl and ethoxypropyl. Particular alkoxyalkyl group include methoxymethyl and methoxyethyl. More particular alkoxyalkyl group is methoxymethyl.

The term "alkoxycarbonyl" denotes a group of the formula —C(O)—R', wherein R' is an alkoxy group. Examples of alkoxycarbonyl groups include groups of the formula —C(O)—R', wherein R' is methoxy, ethoxy, n-propoxy, isopropoxy, n-butoxy, isobutoxy and tert-butoxy. Particular alkoxycarbonyl group is a group of the formula —C(O)—R', wherein R' is methoxy or tert-butoxy.

The term "alkyl" denotes a monovalent linear or branched saturated hydrocarbon group of 1 to 12 carbon atoms. In particular embodiments, alkyl has 1 to 7 carbon atoms, and in more particular embodiments 1 to 4 carbon atoms. Examples of alkyl include methyl, ethyl, propyl, isopropyl, n-butyl, iso-butyl, sec-butyl, and, Particular alkyl groups include methyl, isopropyl, ethyl and tert-butyl. More particular alkyl group is ethyl.

The term "alkylcarbonyl" of the formula —C(O)—R', wherein R' is an alkyl group. Examples of alkylcarbonyl groups include groups of the formula —C(O)—R', wherein R' is methyl or ethyl.

The term "alkylcarbonylamino" denotes an amino group wherein one of the hydrogen atoms of the —NH$_2$ group is replaced by an alkylcarbonyl group. Examples of alkylcarbonylamino groups include groups wherein R' is methyl or ethyl.

The term "alkylcarbonylaminoalkyl" denotes an aminoalkyl group wherein one of the hydrogen atoms of the —NH$_2$ group is replaced by an alkylcarbonyl group. Examples of alkylcarbonylaminoalkyl groups include groups wherein R' is methyl or ethyl.

The term "alkylcycloalkyl" denotes a cycloalkyl group wherein at least one of the hydrogen atoms of the cycloalkyl group is replaced by an alkyl group. Examples of alkylcycloalkyl include methyl-cyclopropyl, dimethyl-cyclopropyl, methyl-cyclobutyl, dimethyl-cyclobutyl, methyl-cyclopentyl, dimethyl-cyclopentyl, methyl-cyclohexyl and dimethyl-cyclohexyl. Particular alkylcycloalkyl groups include methyl-cyclopropyl and dimethyl-cyclopropyl.

The term "alkylcycloalkylalkyl" denotes an alkyl group wherein at least one of the hydrogen atoms of the alkyl group is replaced by an alkylcycloalkyl group. Examples of alkylcycloalkylalkyl include methyl-cyclopropylmethyl, dimethyl-cyclopropylmethyl, methyl-cyclopropylethyl, dimethyl-cyclopropylethyl, methyl-cyclobutylmethyl, dimethyl-cyclobutylmethyl, methyl-cyclobutylethyl, dimethyl-cyclobutylethyl, methyl-cylopentylmethyl, dimethyl-cylopentylmethyl, methyl-cyclopentylethyl, dimethyl-cyclopentylethyl, methyl-cyclohexylmethyl, dimethyl-cyclohexylmethyl, methyl-cyclohexylethyl, dimethyl-cyclohexylethyl, methyl-cycloheptylmethyl, dimethyl-cycloheptylmethyl, methyl-cycloheptylethyl, dimethyl-cycloheptylethyl, methyl-cyclooctylmethyl, dimethyl-cyclooctylmethyl, methyl-cyclooctylethyl and dimethyl-cyclooctylethyl.

The term "amino" denotes a —NH$_2$ group.

The term "aminoalkyl" denotes an alkyl group wherein at least one of the hydrogen atoms of the alkyl group has been replaced by an amino group. Examples of aminoalkyl include aminomethyl, aminoethyl, aminopropyl, aminomethylpropyl and diaminopropyl.

The term "aminocarbonyl" of the formula —C(O)—NH$_2$

The term "aryl" denotes a monovalent aromatic carbocyclic mono- or bicyclic ring system comprising 6 to 10 carbon ring atoms. Examples of aryl group include phenyl and naphthyl. Particular aryl group is phenyl.

The term "bicyclic ring system" denotes two rings which are fused to each other via a common single or double bond (annelated bicyclic ring system), via a sequence of three or more common atoms (bridged bicyclic ring system) or via a common single atom (spiro bicyclic ring system). Bicyclic ring systems can be saturated, partially unsaturated, unsaturated or aromatic. Bicyclic ring systems can comprise heteroatoms selected from N, O and S.

The term "carbonyl" denotes a —C(O)— group.

The term "cyano" denotes a —C≡N group.

The term "cycloalkoxy" denotes a group of the formula —O—R', wherein R' is a cycloalkyl group. Examples of cycloalkoxy group include cyclopropoxy, cyclobutoxy, cyclopentyloxy, cyclohexyloxy, cycloheptyloxy and cyclooctyloxy. Particular cycloalkoxy group is cyclopropoxy.

The term "cycloalkoxyalkyl" denotes an alkyl group wherein at least one of the hydrogen atoms of the alkyl group has been replaced by a cycloalkoxy group. Examples of cycloalkoxyalkyl group include cyclopropoxymethyl, cyclopropoxyethyl, cyclobutoxymethyl, cyclobutoxyethyl, cyclopentyloxymethyl, cyclopentyloxyethyl, cyclohexyloxymethyl, cyclohexyloxyethyl, cycloheptyloxymethyl, cycloheptyloxyethyl, cyclooctyloxymethyl and cyclooctyloxyethyl.

The term "cycloalkyl" denotes a monovalent saturated monocyclic or bicyclic hydrocarbon group of 3 to 10 ring carbon atoms. In particular embodiments, cycloalkyl denotes a monovalent saturated monocyclic hydrocarbon group of 3 to 8 ring carbon atoms. Bicyclic means consisting of two saturated carbocycles having two carbon atoms in common. Particular cycloalkyl groups are monocyclic. Examples for monocyclic cycloalkyl are cyclopropyl, cyclobutanyl, cyclopentyl, cyclohexyl or cycloheptyl. Examples for bicyclic cycloalkyl are bicyclo[2.2.1]heptanyl or bicyclo[2.2.2]octanyl. Particular monocyclic cycloalkyl group is cyclopropyl.

The term "cycloalkylalkoxy" denotes an alkoxy group wherein at least one of the hydrogen atoms of the alkoxy group is replaced by a cycloalkyl group. Examples of cycloalkylalkoxy include cyclopropylmethoxy, cyclobutylmethoxy, cyclopentylmethoxy, cyclohexylmethoxy, cycloheptylmethoxy and cyclooctylmethoxy.

The term "cycloalkylalkoxyalkyl" denotes an alkyl group wherein at least one of the hydrogen atoms of the alkyl group is replaced by a cycloalkylalkoxy group. Examples of cycloalkylalkoxyalkyl include cyclopropylmethoxymethyl, cyclopropylmethoxyethyl, cyclobutylmethoxymethyl, cyclobutylmethoxyethyl, cyclopentylmethoxymethyl, cyclopentylmethoxyethyl, cyclohexylmethoxymethyl, cyclohexylmethoxyethyl, cycloheptylmethoxymethyl, cycloheptylmethoxyethyl, cyclooctylmethoxymethyl and cyclooctylmethoxyethyl.

The term "cycloalkylalkyl" denotes an alkyl group wherein at least one of the hydrogen atoms of the alkyl group is replaced by a cycloalkyl group. Examples of cycloalkylalkyl include cyclopropylmethyl, cyclopropylethyl, cyclobutylpropyl and cyclopentylbutyl.

The term "cycloalkylcarbonyl" of the formula —C(O)—R', wherein R' is a cycloalkyl group. Examples of cycloalkylcarbonyl groups include groups of the formula —C(O)—R', wherein R' is cyclopropyl.

The term "cycloalkylcarbonylamino" denotes an amino group wherein one of the hydrogen atoms of the —NH₂ group is replaced by a cycloalkylcarbonyl group. Examples of alkylcarbonylamino groups include groups wherein R' is cyclopropyl.

The term "cycloalkylcarbonylaminoalkyl" denotes an aminoalkyl group wherein one of the hydrogen atoms of the —NH₂ group is replaced by a cycloalkylcarbonyl group. Examples of alkylcarbonylaminoalkyl groups include groups wherein R' is cyclopropyl.

The term "haloalkoxy" denotes an alkoxy group wherein at least one of the hydrogen atoms of the alkoxy group has been replaced by same or different halogen atoms. The term "perhaloalkoxy" denotes an alkoxy group where all hydrogen atoms of the alkoxy group have been replaced by the same or different halogen atoms. Examples of haloalkoxy include fluoromethoxy, difluoromethoxy, trifluoromethoxy, trifluoroethoxy, trifluoromethylethoxy, trifluorodimethylethoxy and pentafluoroethoxy. Particular haloalkoxy groups are trifluoromethoxy and 2,2-difluoroethoxy.

The term "haloalkoxyalkyl" denotes an alkyl group wherein at least one of the hydrogen atoms of the alkyl group has been replaced by a haloalkoxy group. Examples of haloalkoxyalkyl include fluoromethoxymethyl, difluoromethoxymethyl, trifluoromethoxymethyl, fluoroethoxymethyl, difluoroethoxymethyl, trifluoroethoxymethyl, fluoromethoxyethyl, difluoromethoxyethyl, trifluoromethoxyethyl, fluoroethoxyethyl, difluoroethoxyethyl, trifluoroethoxyethyl, fluoromethoxypropyl, difluoromethoxypropyl, trifluoromethoxypropyl, fluoroethoxypropyl, difluoroethoxypropyl and trifluoroethoxypropyl. Particular haloalkoxyalkyl is 2,2-difluoroethoxyethyl The term "haloalkyl" denotes an alkyl group wherein at least one of the hydrogen atoms of the alkyl group has been replaced by same or different halogen atoms. The term "perhaloalkyl" denotes an alkyl group where all hydrogen atoms of the alkyl group have been replaced by the same or different halogen atoms. Examples of haloalkyl include fluoromethyl, difluoromethyl, trifluoromethyl, trifluoroethyl, trifluoromethylethyl and pentafluoroethyl. Particular haloalkyl groups are trifluoromethyl and trifluoroethyl.

The term "halocycloalkyl" denotes a cycloalkyl group wherein at least one of the hydrogen atoms of the cycloalkyl group has been replaced by same or different halogen atoms, particularly fluoro atoms. Examples of halocycloalkyl groups include fluorocyclopropyl, difluorocyclopropyl, fluorocyclobutyl and difluorocyclobutyl.

The term "halocycloalkylalkyl" denotes an alkyl group wherein at least one of the hydrogen atoms of the alkyl group has been replaced by a halocycloalkyl. Examples of halocycloalkylalkyl groups include fluorocyclopropylmethyl, fluorocyclopropylethyl, difluorocyclopropylmethyl, difluorocyclopropylethyl, fluorocyclobutylmethyl, fluorocyclobutylethyl, difluorocyclobutylmethyl and difluorocyclobutylethyl.

The term "halogen" and "halo" are used interchangeably herein and denote fluoro, chloro, bromo, or iodo. Particular halogens are chloro and fluoro.

The term "halohydroxyalkyl" denotes an alkyl group wherein at least one of the hydrogen atoms of the alkyl group has been replaced by same or different halogen atoms and at least one of the hydrogen atoms of the alkyl group has been replaced by hydroxy.

The term "heteroaryl" denotes a monovalent aromatic heterocyclic mono- or bicyclic ring system of 5 to 12 ring atoms, comprising 1, 2, 3 or 4 heteroatoms selected from N, O and S, the remaining ring atoms being carbon. Examples of heteroaryl group include pyrrolyl, furanyl, thienyl, imidazolyl, oxazolyl, thiazolyl, triazolyl, oxadiazolyl, thiadiazolyl, tetrazolyl, pyridinyl, pyrazinyl, pyrazolyl, pyridazinyl, pyrimidinyl, triazinyl, azepinyl, diazepinyl, isoxazolyl, benzofuranyl, isothiazolyl, benzothienyl, indolyl, isoindolyl, isobenzofuranyl, benzimidazolyl, benzoxazolyl, benzoisoxazolyl, benzothiazolyl, benzoisothiazolyl, benzooxadiazolyl, benzothiadiazolyl, benzotriazolyl, purinyl, quinolinyl, isoquinolinyl, quinazolinyl and quinoxalinyl. Particular heteroaryl groups include pyrrolyl, furanyl, thienyl, imidazolyl, oxazolyl, thiazolyl, triazolyl, oxadiazolyl, thiadiazolyl, tetrazolyl, pyridinyl, pyrazinyl, pyrazolyl, pyridazinyl, pyrimidinyl, isoxazolyl and isothiazolyl. More particular heteroaryl groups include imidazolyl, oxazolyl, thiazolyl, oxadiazolyl, thiadiazolyl, tetrazolyl, pyridinyl, pyrazinyl, pyrazolyl, pyridazinyl, pyrimidinyl, isoxazolyl and isothiazolyl.

The term "heterocycloalkyl" denotes a monovalent saturated or partly unsaturated mono- or bicyclic ring system of 3 to 9 ring atoms, comprising 1, 2, or 3 ring heteroatoms selected from N, O and S, the remaining ring atoms being carbon. In particular embodiments, heterocycloalkyl is a monovalent saturated monocyclic ring system of 4 to 7 ring atoms, comprising 1, 2, or 3 ring heteroatoms selected from N, O and S, the remaining ring atoms being carbon. Examples for monocyclic saturated heterocycloalkyl are aziridinyl, oxiranyl, azetidinyl, oxetanyl, pyrrolidinyl, tetrahydrofuranyl, tetrahydro-thienyl, pyrazolidinyl, imidazolidinyl, oxazolidinyl, isoxazolidinyl, thiazolidinyl, piperidinyl, tetrahydropyranyl, tetrahydrothiopyranyl, piperazinyl, morpholinyl, thiomorpholinyl, 1,1-dioxo-thiomorpholin-4-yl, azepanyl, diazepanyl, homopiperazinyl, oxazepanyl and thiazinanyl. Examples for bicyclic saturated heterocycloalkyl are 8-aza-bicyclo[3.2.1]octyl, quinuclidinyl, 8-oxa-3-aza-bicyclo[3.2.1]octyl, 9-aza-bicyclo[3.3.1]nonyl, 3-oxa-9-aza-bicyclo[3.3.1]nonyl, 3-thia-9-aza-bicyclo[3.3.1]nonyl and 2,6-diaza-spiro[3.3]heptanyl. Examples for partly unsaturated heterocycloalkyl are dihydrofuryl, imidazolinyl, dihydro-oxazolyl, tetrahydro-pyridinyl, or dihydropyranyl. More particular examples of heterocycloalkyl group are pyrrolidinyl, pyrazolidinyl, imidazolidinyl, oxazolidinyl, isoxazolidinyl, thiazolidinyl, piperidinyl, tetrahydropyranyl, tetrahydrothiopyranyl, piperazinyl, morpholinyl, thiomorpholinyl, 1,1-dioxo-thiomorpholin-4-yl, azepanyl, diazepanyl, homopiperazinyl, oxazepanyl, thiazinanyl and 2,6-diaza-spiro[3.3]heptanyl. More particular examples of a heterocycloalkyl are pyrrolydinyl, piperidinyl, thiomorpholinyl, thiazinanyl and 2,6-diaza-spiro[3.3]heptanyl.

The term "hydroxy" denotes a —OH group.

The term "hydroxyalkyl" denotes an alkyl group wherein at least one of the hydrogen atoms of the alkyl group has been replaced by a hydroxy group. Examples of hydroxyalkyl include hydroxymethyl, hydroxyethyl, hydroxypropyl, hydroxymethylpropyl and dihydroxypropyl. Particular example is hydroxymethyl.

The term "oxo" denotes a divalent oxygen atom =O.

The term "phenylalkyl" denotes an alkyl group wherein one of the hydrogen atoms of the alkyl group has been replaced by a phenyl. Examples of phenylalkyl are benzyl and phenylethyl. Particular example of phenylalkyl is benzyl.

The term "tetrazolylalkyl" denotes an alkyl group wherein one of the hydrogen atoms of the alkyl group has been replaced by a tetrazolyl. Examples of tetrazolylalkyl are tetrazolylmethyl and tetrazolylethyl. Particular example of tetrazolylalkyl is tetrazolylmethyl.

The term "triazolylalkyl" denotes an alkyl group wherein one of the hydrogen atoms of the alkyl group has been replaced by a triazolyl. Examples of triazolylalkyl are triazolylmethyl and triazolylethyl. Particular example of triazolylalkyl is triazolylmethyl.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, in particular hydrochloric acid, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. In addition these salts may be prepared by addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyimine resins and the like. Particular pharmaceutically acceptable salts of compounds of formula (I) are the hydrochloride salts, methanesulfonic acid salts and citric acid salts.

"Pharmaceutically acceptable esters" means that compounds of general formula (I) may be derivatised at functional groups to provide derivatives which are capable of conversion back to the parent compounds in vivo. Examples of such compounds include physiologically acceptable and metabolically labile ester derivatives, such as methoxymethyl esters, methylthiomethyl esters and pivaloyloxymethyl esters. Additionally, any physiologically acceptable equivalents of the compounds of general formula (I), similar to the metabolically labile esters, which are capable of producing the parent compounds of general formula (I) in vivo, are within the scope of this invention.

The term "protecting group" (PG) denotes the group which selectively blocks a reactive site in a multifunctional compound such that a chemical reaction can be carried out selectively at another unprotected reactive site in the meaning conventionally associated with it in synthetic chemistry. Protecting groups can be removed at the appropriate point. Exemplary protecting groups are amino-protecting groups, carboxy-protecting groups or hydroxy-protecting groups. Particular protecting groups are the tert-butoxycarbonyl (Boc), benzyloxycarbonyl (Cbz), fluorenylmethoxycarbonyl (Fmoc) and benzyl (Bn). Further particular protecting groups are the tert-butoxycarbonyl (Boc) and the fluorenylmethoxycarbonyl (Fmoc). More particular protecting group is the tert-butoxycarbonyl (Boc).

The abbreviation uM means microMolar and is equivalent to the symbol μM.

The compounds of the present invention can also contain unnatural proportions of atomic isotopes at one or more of the atoms that constitute such compounds. For example, the present invention also embraces isotopically-labeled variants of the present invention which are identical to those recited herein, but for the fact that one or more atoms are replaced by an atom having the atomic mass or mass number different from the predominant atomic mass or mass number usually found in nature for the atom. All isotopes of any particular atom or element as specified are contemplated within the scope of the compounds of the invention, and their uses. Exemplary isotopes that can be incorporated into compounds of the invention include isotopes of hydrogen, carbon, nitrogen, oxygen, phosphorous, sulfur, fluorine, chlorine and iodine, such as $^{2}H$ ("D"), $^{3}H$ ("T"), $^{11}C$, $^{13}C$, $^{14}C$, $^{13}N$, $^{15}N$, $^{15}O$, $^{17}O$, $^{18}O$, $^{32}P$, $^{33}P$, $^{35}S$, $^{18}F$, $^{36}Cl$, $^{123}I$ and $^{125}I$. Certain isotopically labeled compounds of the present invention (e.g., those labeled with $^3$H or $^{14}$C) are useful in compound and/or substrate tissue distribution assays. Tritiated ($^3$H) and carbon-14 ($^{14}$C) isotopes are useful for their ease of preparation and detectability. Further substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Positron emitting isotopes such as $^{15}$O, $^{13}$N, $^{11}$C, and $^{18}$F are useful for positron emission tomography (PET) studies to examine substrate receptor occupancy. Isotopically labeled compounds of the present inventions can generally be prepared by following procedures analogous to those disclosed in the Schemes and/or in the Examples herein below, by substituting a non-isotopically labeled reagent with a isotopically labeled reagent. In particular, compounds of formula (I) wherein one or more H atom have been replaced by a $^2$H atom are also an embodiment of this invention.

The present invention relates to a compound according to formula (I), (I)

[chemical structure showing a bicyclic system with substituents $R^1$ through $R^{12}$, ring atoms $A^1$, $A^2$, $A^3$, a pyridine ring, and indices $n$]

wherein
$R^1$ is selected from the group consisting of H, alkyl, haloalkyl, cycloalkyl and halocycloalkyl;
$R^2$ is selected from the group consisting of H, alkyl, haloalkyl, cycloalkyl and halocycloalkyl;
$R^3$ is selected from the group consisting of H, alkyl, haloalkyl, cycloalkyl and halocycloalkyl;
$R^4$ is selected from the group consisting of H, alkyl, haloalkyl, cycloalkyl and halocycloalkyl;
$R^5$ is selected from the group consisting of H, alkyl, haloalkyl, cycloalkyl and halocycloalkyl;
$R^6$ is selected from the group consisting of H, alkyl, haloalkyl, cycloalkyl and halocycloalkyl;
$R^7$ is selected from the group consisting of H, alkyl, haloalkyl, cycloalkyl and halocycloalkyl;
$R^8$ is selected from the group consisting of H, alkyl, haloalkyl, cycloalkyl and halocycloalkyl;
$R^9$ is selected from the group consisting of H, alkyl, haloalkyl, cycloalkyl and halocycloalkyl;
$R^{10}$ is selected from the group consisting of H, alkyl, haloalkyl, cycloalkyl and halocycloalkyl;
$R^{11}$ is selected from the group consisting of H, alkyl, haloalkyl, cycloalkyl and halocycloalkyl;
$R^{12}$ is selected from the group consisting of H, halogen, alkyl, haloalkyl, cycloalkyl and halocycloalkyl;
$A^1$ is N or $CR^{13}$;
$A^2$ is $NR^{14}$ or $CR^{15}R^{16}$;
$A^3$ is N or $CR^{17}$;
$R^{13}$ is selected from the group consisting of H, halogen, alkyl, haloalkyl, cycloalkyl and halocycloalkyl;
$R^{14}$ is selected from the group consisting of —S(O)$_2$R$^{18}$, —S(O)$_2$OR$^{18}$, —S(O)$_2$NR$^{18}$R$^{19}$, —C(O)R$^{18}$, —C(O)OR$^{18}$, —C(O)NR$^{18}$R$^{19}$ and —(CR$^{20}$R$^{21}$)$_q$—(CR$^{22}$R$^{23}$)$_r$—(CR$^{24}$R$^{25}$)$_p$—NR$^{26}$R$^{27}$, wherein the sum of q, r and p is at least 2;
$R^{15}$ is —(CR$^{20}$R$^{21}$)$_q$—(CR$^{22}$R$^{23}$)$_r$—(CR$^{24}$R$^{25}$)$_p$—NR$^{26}$R$^{27}$;
$R^{16}$ is selected from the group consisting of H, alkyl, haloalkyl, cycloalkyl and halocycloalkyl;
or $R^6$ and $R^{16}$ together with the carbon atoms to which they are attached form a double bond;
$R^{17}$ is selected from the group consisting of H, halogen, alkyl, haloalkyl, cycloalkyl and halocycloalkyl;
$R^{18}$ is selected from the group consisting of cycloalkyl, alkylcycloalkyl, halocycloalkyl, alkylcycloalkylalkyl, halocycloalkylalkyl, cycloalkylalkyl, cycloalkoxyalkyl, cycloalkylalkoxyalkyl, triazolylalkyl, tetrazolylalkyl, aminoalkyl, substituted aminoalkyl, substituted aryl, substituted heterocycloalkyl and substituted heteroaryl, wherein said substituted aminoalkyl is substituted on the nitrogen atom with one to two substituents independently selected from the group consisting of alkyl, cycloalkyl, alkylcycloalkyl, cycloalkylalkyl, alkylcycloalkylalkyl, hydroxyalkyl and alkoxyalkyl, and wherein said substituted aryl, substituted heterocycloalkyl and substituted heteroaryl are substituted with R$^{28}$, R$^{29}$ and R$^{30}$;
$R^{19}$ is selected from the group consisting of H, alkyl, haloalkyl, cycloalkyl, halocycloalkyl, alkoxyalkyl, haloalkoxyalkyl and hydroxyalkyl; or $R^{18}$ and $R^{19}$ together with the nitrogen atom to which they are attached form a substituted heterocycloalkyl or a substituted heteroaryl, wherein said substituted heterocycloalkyl and substituted heteroaryl are substituted with R$^{28}$, R$^{29}$ and R$^{30}$;
$R^{20}$ is selected from the group consisting of H, alkyl, haloalkyl, cycloalkyl and halocycloalkyl;
$R^{21}$ is selected from the group consisting of H, alkyl, haloalkyl, cycloalkyl and halocycloalkyl;
$R^{22}$ is selected from the group consisting of H, alkyl, haloalkyl, cycloalkyl and halocycloalkyl;
$R^{23}$ is selected from the group consisting of H, alkyl, haloalkyl, cycloalkyl and halocycloalkyl;
or $R^{22}$ and $R^{23}$ together with the carbon atom to which they are attached form a cycloalkyl;
$R^{24}$ is selected from the group consisting of H, alkyl, haloalkyl, cycloalkyl and halocycloalkyl;
$R^{25}$ is selected from the group consisting of H, alkyl, haloalkyl, cycloalkyl and halocycloalkyl;
or $R^{21}$ and $R^{25}$ together form —(CH$_2$)$_t$—;
$R^{26}$ is selected from the group consisting of H, alkyl, haloalkyl, cycloalkyl, halocycloalkyl, alkoxyalkyl, haloalkoxyalkyl and hydroxyalkyl;
$R^{27}$ is selected from the group consisting of H, alkyl, haloalkyl, cycloalkyl, halocycloalkyl, hydroxyalkyl, alkoxyalkyl, haloalkoxyalkyl, phenylalkyl, substituted phenylalkyl, substituted aryl, heterocycloalkyl, substituted heterocycloalkyl, substituted heteroaryl, —S(O)$_2$R$^{31}$, —S(O)$_2$OR$^{31}$, —S(O)$_2$NR$^{31}$R$^{32}$, —C(O)R$^{31}$, —C(O)OR$^{31}$ and —C(O)NR$^{31}$R$^{32}$, wherein said substituted phenylalkyl, substituted aryl, substituted heterocycloalkyl and substituted heteroaryl are substituted with R$^{28}$, R$^{29}$ and R$^{30}$, wherein in case R$^{26}$ is H or alkyl and R$^{27}$ is H or alkyl, then the sum of q, r and p is at least 1;
or $R^{26}$ and $R^{27}$ together with the nitrogen atom to which they are attached form a substituted heterocycloalkyl or a substituted heteroaryl, wherein said substituted heterocycloalkyl and substituted heteroaryl are substituted with R$^{28}$, R$^{29}$ and R$^{30}$;
or $R^{25}$ and $R^{26}$ together with the nitrogen atom to which they are attached form a substituted heterocycloalkyl or a substituted heteroaryl, wherein said substituted heterocycloalkyl and substituted heteroaryl are substituted with $R^{28}$, $R^{29}$ and $R^{30}$;

or $R^{23}$ and $R^{26}$ together with the nitrogen atom to which they are attached form a substituted heterocycloalkyl or a substituted heteroaryl, wherein said substituted heterocycloalkyl and substituted heteroaryl are substituted with $R^{28}$, $R^{29}$ and $R^{30}$;

or $R^{21}$ and $R^{26}$ together with the nitrogen atom to which they are attached form a substituted heterocycloalkyl or a substituted heteroaryl, wherein said substituted heterocycloalkyl and substituted heteroaryl are substituted with $R^{28}$, $R^{29}$ and $R^{30}$;

$R^{28}$, $R^{29}$ and $R^{30}$ are each independently selected from the group consisting of H, alkyl, hydroxyalkyl, haloalkyl, cycloalkyl, alkylcycloalkyl, halocycloalkyl, alkylcycloalkylalkyl, halocycloalkylalkyl, cycloalkylalkyl, cycloalkylalkoxy, cycloalkoxy, cycloalkoxyalkyl, cycloalkylalkoxyalkyl, alkoxy, alkoxyalkyl, haloalkoxy, haloalkoxyalkyl, alkoxyalkoxy, alkoxyalkoxyalkyl, alkoxycarbonyl, halogen, hydroxy, oxo, cyano, triazolylalkyl, tetrazolylalkyl, amino, substituted amino, aminoalkyl, substituted aminoalkyl, aminocarbonyl, substituted aminocarbonyl, alkylcarbonylamino, cycloalkylcarbonylamino, alkylcarbonylaminoalkyl and cycloalkylcarbonylaminoalkyl, wherein said substituted amino, substituted aminoalkyl and substituted aminocarbonyl are substituted on the nitrogen atom with one to two substituents independently selected from the group consisting of alkyl, cycloalkyl, alkylcycloalkyl, cycloalkylalkyl, alkylcycloalkylalkyl, hydroxyalkyl and alkoxyalkyl;

wherein in case $R^{14}$ is —S(O)$_2$R$^{18}$ or in case $R^{26}$ and $R^{27}$ or $R^{21}$ and $R^{26}$ or $R^{23}$ and $R^{26}$ or $R^{25}$ and $R^{26}$ together with the nitrogen atom to which they are attached form a substituted heterocycloalkyl or a substituted heteroaryl, then at least one of $R^{27}$, $R^{28}$, $R^{29}$ and $R^{30}$ is different from H, alkyl, haloalkyl, alkoxy, haloalkoxy, halogen, hydroxy, cyano, amino, substituted amino, aminocarbonyl or substituted aminocarbonyl, wherein substituted amino and substituted aminocarbonyl are substituted on the nitrogen atom with one to two alkyl;

$R^{31}$ is selected from the group consisting of H, alkyl, hydroxyalkyl, haloalkyl, cycloalkyl, alkylcycloalkyl, halocycloalkyl, alkylcycloalkylalkyl, halocycloalkylalkyl, cycloalkylalkyl, cycloalkoxyalkyl, cycloalkylalkoxyalkyl, alkoxyalkyl, haloalkoxyalkyl, alkoxyalkoxyalkyl, triazolylalkyl, tetrazolylalkyl, aminoalkyl, substituted aminoalkyl, substituted aryl, substituted heterocycloalkyl and substituted heteroaryl, wherein said substituted aminoalkyl is substituted on the nitrogen atom with one to two substituents independently selected from the group consisting of alkyl, cycloalkyl, alkylcycloalkyl, cycloalkylalkyl, alkylcycloalkylalkyl, hydroxyalkyl and alkoxyalkyl, and wherein said substituted aryl, substituted heterocycloalkyl and substituted heteroaryl are substituted with $R^{28}$, $R^{29}$ and $R^{30}$;

$R^{32}$ is selected from the group consisting of H, alkyl, haloalkyl, cycloalkyl, halocycloalkyl, alkoxyalkyl, haloalkoxyalkyl and hydroxyalkyl;

n is zero, 1 or 2;
p is zero, 1 or 2;
q is zero, 1 or 2;
r is zero, 1 or 2; and
t is zero, 1, 2 or 3;
or a pharmaceutically acceptable salt or ester thereof.

The compounds of formula (I) can contain several asymmetric centers and can be present in the form of optically pure enantiomers, mixtures of enantiomers such as, for example, racemates, optically pure diastereoisomers, mixtures of diastereoisomers, diastereoisomeric racemates or mixtures of diastereoisomeric racemates.

According to the Cahn-Ingold-Prelog Convention the asymmetric carbon atom can be of the "R" or "S" configuration.

Also an embodiment of the present invention are compounds according to formula (I) as described herein and pharmaceutically acceptable salts or esters thereof, in particular compounds according to formula (I) as described herein and pharmaceutically acceptable salts thereof, more particularly compounds according to formula (I) as described herein.

A further embodiment of the present invention are compounds according to formula (I) as described herein, wherein $R^1$ is H or alkyl.

A particular embodiment of the present invention are compounds according to formula (I) as described herein, wherein $R^1$ is alkyl.

In a further embodiment of the present invention are compounds according to formula (I) as described herein, wherein $R^1$ is methyl.

Another further embodiment of the present invention are compounds according to formula (I) as described herein, wherein $R^2$ is H.

Another embodiment of the present invention are compounds according to formula (I) as described herein, wherein $R^3$ is H.

The present invention also relates to compounds according to formula (I) as described herein, wherein $R^4$ is H or alkyl.

A further particular embodiment of the present invention are compounds according to formula (I) as described herein, wherein $R^4$ is H.

A more particular embodiment of the present invention are compounds according to formula (I) as described herein, wherein $R^5$ is H or alkyl.

Also an embodiment of the present invention are compounds according to formula (I) as described herein, wherein $R^5$ is H.

Also an embodiment of the present invention are compounds according to formula (I) as described herein, wherein $R^6$ is selected from the group consisting of H, halogen and alkyl.

The present invention also relates to compounds according to formula (I) as described herein, wherein $R^6$ is H.

Another embodiment of the present invention are compounds according to formula (I) as described herein, wherein $R^7$ is H.

A further particular embodiment of the present invention are compounds according to formula (I) as described herein, wherein is $R^8$ is H.

A particular embodiment of the present invention are compounds according to formula (I) as described herein, wherein $R^9$ is H.

Also an embodiment of the present invention are compounds according to formula (I) as described herein, wherein $R^{10}$ is H.

The present invention also relates to compounds according to formula (I) as described herein, wherein $R^{11}$ is H.

Another embodiment of the present invention are compounds according to formula (I) as described herein, wherein $R^{12}$ is H or halogen.

The present invention also relates to compounds according to formula (I) as described herein, wherein $R^{12}$ is H.

Also an embodiment of the present invention are compounds according to formula (I) as described herein, wherein $A^1$ is $CR^{13}$.

Another embodiment of the present invention are compounds according to formula (I) as described herein, wherein $A^2$ is $NR^{14}$.

Also an embodiment of the present invention are compounds according to formula (I) as described herein, wherein $A^2$ is $CR^{15}R^{16}$.

A particular embodiment of the present invention are compounds according to formula (I) as described herein, wherein $A^3$ is $CR^{17}$.

A particular embodiment of the present invention are compounds according to formula (I) as described herein, wherein $R^{13}$ is H or halogen.

A further particular embodiment of the present invention are compounds according to formula (I) as described herein, wherein $R^{13}$ is H.

A more particular embodiment of the present invention are compounds according to formula (I) as described herein, wherein $R^{14}$ is selected from the group consisting of $-S(O)_2R^{18}$, $-S(O)_2OR^{18}$, $-S(O)_2NR^{18}R^{19}$, $-C(O)R^{18}$, $-C(O)OR^{18}$, and $-C(O)NR^{18}R^{19}$.

Also a particular embodiment of the present invention are compounds according to formula (I) as described herein, wherein $R^{14}$ is $-(CR^{20}R^{21})_q-(CR^{22}R^{23})_r-(CR^{24}R^{25})_p-NR^{26}R^{27}$, wherein the sum of q, r and p is at least 2.

Also a particular embodiment of the present invention are compounds according to formula (I) as described herein, wherein $R^6$ and $R^{16}$ together with the carbon atoms to which they are attached form a double bond.

Another embodiment of the present invention are compounds according to formula (I) as described herein, wherein $R^{16}$ is selected from the group consisting of H, alkyl, haloalkyl, cycloalkyl and halocycloalkyl.

Also a particular embodiment of the present invention are compounds according to formula (I) as described herein, wherein $R^{16}$ is H.

Another embodiment of the present invention are compounds according to formula (I) as described herein, wherein $R^{17}$ is H.

Another embodiment of the present invention are compounds according to formula (I) as described herein, wherein $R^{18}$ is selected from the group consisting of cycloalkyl, alkylcycloalkyl, halocycloalkyl, alkylcycloalkylalkyl, halocycloalkylalkyl, cycloalkylalkyl, cycloalkoxyalkyl, cycloalkylalkoxyalkyl, triazolylalkyl, tetrazolylalkyl, aminoalkyl, substituted aminoalkyl, substituted aryl, substituted heterocycloalkyl and substituted heteroaryl, wherein substituted aminoalkyl is substituted on the nitrogen atom with one to two substituents independently selected from the group consisting of alkyl, cycloalkyl, alkylcycloalkyl, cycloalkylalkyl, alkylcycloalkylalkyl, hydroxyalkyl and alkoxyalkyl, and wherein said substituted aryl, substituted heterocycloalkyl and substituted heteroaryl are substituted with $R^{28}$, $R^{29}$ and $R^{30}$.

Also an embodiment of the present invention are compounds according to formula (I) as described herein, wherein $R^{19}$ is selected from the group consisting of H, alkyl, haloalkyl, cycloalkyl, halocycloalkyl, alkoxyalkyl, haloalkoxyalkyl and hydroxyalkyl.

Also an embodiment of the present invention are compounds according to formula (I) as described herein, wherein $R^{18}$ and $R^{19}$ together with the nitrogen atom to which they are attached form a substituted heterocycloalkyl or a substituted heteroaryl, wherein substituted heterocycloalkyl and substituted heteroaryl are substituted with $R^{28}$, $R^{29}$ and $R^{30}$.

Also an embodiment of the present invention are compounds according to formula (I) as described herein, wherein $R^{20}$ is H.

Also an embodiment of the present invention are compounds according to formula (I) as described herein, wherein $R^{21}$ is H.

A further embodiment of the present invention are compounds according to formula (I) as described herein, wherein $R^{22}$ is H.

Also an embodiment of the present invention are compounds according to formula (I) as described herein, wherein $R^{23}$ is H.

Another embodiment of the present invention are compounds according to formula (I) as described herein, wherein $R^{24}$ is H.

A further embodiment of the present invention are compounds according to formula (I) as described herein, wherein $R^{25}$ is H.

A particular embodiment of the present invention are compounds according to formula (I) as described herein, wherein $R^{22}$ and $R^{23}$ together with the carbon atom to which they are attached form a cycloalkyl.

A further particular embodiment of the present invention are compounds according to formula (I) as described herein, wherein $R^{21}$ and $R^{25}$ together form $-(CH_2)_t-$.

A more particular embodiment of the present invention are compounds according to formula (I) as described herein, wherein $R^{26}$ is selected from the group consisting of H, alkyl, haloalkyl, cycloalkyl, halocycloalkyl, alkoxyalkyl, haloalkoxyalkyl and hydroxyalkyl.

Another embodiment of the present invention are compounds according to formula (I) as described herein, wherein $R^{26}$ is H.

Another particular embodiment of the present invention are compounds according to formula (I) as described herein, wherein $R^{27}$ is selected from the group consisting of H, alkyl, haloalkyl, cycloalkyl, halocycloalkyl, hydroxyalkyl, alkoxyalkyl, haloalkoxyalkyl, phenylalkyl, substituted phenylalkyl, substituted aryl, heterocycloalkyl, substituted heterocycloalkyl, substituted heteroaryl, $-S(O)_2R^{31}$, $-S(O)_2OR^{31}$, $-S(O)_2NR^{31}R^{32}$, $-C(O)R^{31}$, $-C(O)OR^{31}$ and $-C(O)NR^{31}R^{32}$, wherein said substituted phenylalkyl, substituted aryl, substituted heterocycloalkyl and substituted heteroaryl are substituted with $R^{28}$, $R^{29}$ and $R^{30}$, wherein in case $R^{26}$ is H or alkyl and $R^{27}$ is H or alkyl, then the sum of q, r and p is at least 1.

A particular embodiment of the present invention are compounds according to formula (I) as described herein, wherein $R^{27}$ is selected from the group consisting of H, $-S(O)_2R^{31}$, $-C(O)R^{31}$ and $-C(O)OR^{31}$, wherein in case $R^{26}$ is H or alkyl and $R^{27}$ is H, then the sum of q, r and p is at least 1.

Also an embodiment of the present invention are compounds according to formula (I) as described herein, wherein $R^{27}$ is $-S(O)_2R^{31}$ or $-C(O)R^{31}$.

Another embodiment of the present invention are compounds according to formula (I) as described herein, wherein $R^{27}$ is $-S(O)_2R^{31}$.

The present invention also relates to compounds according to formula (I) as described herein, wherein $R^{27}$ is $-C(O)R^{31}$.

A further embodiment of the present invention are compounds according to formula (I) as described herein, wherein $R^{26}$ and $R^{27}$ together with the nitrogen atom to which they are attached form a substituted heterocycloalkyl or a substituted heteroaryl, wherein substituted heterocycloalkyl and substituted heteroaryl are substituted with $R^{28}$, $R^{29}$ and $R^{30}$.

A further embodiment of the present invention are compounds according to formula (I) as described herein, wherein $R^{28}$ is halogen.

A embodiment of the present invention are compounds according to formula (I) as described herein, wherein $R^{29}$ and $R^{30}$ are H.

Also an embodiment of the present invention are compounds according to formula (I) as described herein, wherein $R^{31}$ is selected from the group consisting of hydroxyalkyl, cycloalkyl, alkyl and heteroaryl substituted with $R^{28}$, $R^{29}$ and $R^{30}$.

A embodiment of the present invention are compounds according to formula (I) as described herein, wherein $R^{31}$ is alkyl or chloropyridynyl.

A embodiment of the present invention are compounds according to formula (I) as described herein, wherein $R^{31}$ is alkyl.

A embodiment of the present invention are compounds according to formula (I) as described herein, wherein $R^{31}$ is ethyl or tert-butyl.

A embodiment of the present invention are compounds according to formula (I) as described herein, wherein $R^{31}$ is ethyl.

Also an embodiment of the present invention are compounds according to formula (I) as described herein, wherein n is zero or 1.

The present invention also relates to compounds according to formula (I) as described herein, wherein n is zero.

The present invention also relates to compounds according to formula (I) as described herein, wherein n is 1.

Also an embodiment of the present invention are compounds according to formula (I) as described herein, wherein q is zero or 1.

A further embodiment of the present invention are compounds according to formula (I) as described herein, wherein r is zero or 1.

The present invention also relates to compounds according to formula (I) as described herein, wherein p is zero or 1.

The present invention also relates to compounds according to formula (I) as described herein, wherein the sum of q, r and p is zero or 2.

The present invention also relates to compounds according to formula (I) as described herein, wherein q, r and p are zero.

The present invention also relates to compounds according to formula (I) as described herein, wherein the sum of q, r and p is 2.

Particular examples of compounds of formula (I) as described herein are selected from the group consisting of
(rac)-N-[4-(1-Methyl-2-oxo-1,2,3,4-tetrahydro-quinolin-6-yl)-5,6,7,8-tetrahydro-isoquinolin-8-yl]-propionamide;
(−)-N-(4-(1-Methyl-2-oxo-1,2,3,4-tetrahydroquinolin-6-yl)-5,6,7,8-tetrahydroisoquinolin-8-yl)propionamide;
(+)-N-(4-(1-Methyl-2-oxo-1,2,3,4-tetrahydroquinolin-6-yl)-5,6,7,8-tetrahydroisoquinolin-8-yl)propionamide;
(R)—N-(4-(1-Methyl-2-oxo-1,2,3,4-tetrahydroquinolin-6-yl)-5,6,7,8-tetrahydroisoquinolin-8-yl)propionamide;
(S)—N-(4-(1-Methyl-2-oxo-1,2,3,4-tetrahydroquinolin-6-yl)-5,6,7,8-tetrahydroisoquinolin-8-yl)propionamide;
(rac)-N-(4-(1-Methyl-2-oxo-1,2,3,4-tetrahydroquinolin-6-yl)-5,6,7,8-tetrahydroisoquinolin-8-yl)ethanesulfonamide;
(−)-N-(4-(1-Methyl-2-oxo-1,2,3,4-tetrahydroquinolin-6-yl)-5,6,7,8-tetrahydroisoquinolin-8-yl)ethanesulfonamide;
(+)-N-(4-(1-Methyl-2-oxo-1,2,3,4-tetrahydroquinolin-6-yl)-5,6,7,8-tetrahydroisoquinolin-8-yl)ethanesulfonamide;
(R)—N-(4-(1-Methyl-2-oxo-1,2,3,4-tetrahydroquinolin-6-yl)-5,6,7,8-tetrahydroisoquinolin-8-yl)ethanesulfonamide;
(S)—N-(4-(1-Methyl-2-oxo-1,2,3,4-tetrahydroquinolin-6-yl)-5,6,7,8-tetrahydroisoquinolin-8-yl)ethanesulfonamide;
(rac)-N-(4-(1-Methyl-2-oxo-1,2,3,4-tetrahydroquinolin-6-yl)-6,7-dihydro-5H-cyclopenta[c]pyridin-7-yl)propionamide;
(−)-N-(4-(1-Methyl-2-oxo-1,2,3,4-tetrahydroquinolin-6-yl)-6,7-dihydro-5H-cyclopenta[c]pyridin-7-yl)propionamide;
(+)-N-(4-(1-Methyl-2-oxo-1,2,3,4-tetrahydroquinolin-6-yl)-6,7-dihydro-5H-cyclopenta[c]pyridin-7-yl)propionamide;
(R)—N-(4-(1-Methyl-2-oxo-1,2,3,4-tetrahydroquinolin-6-yl)-6,7-dihydro-5H-cyclopenta[c]pyridin-7-yl)propionamide;
(S)—N-(4-(1-Methyl-2-oxo-1,2,3,4-tetrahydroquinolin-6-yl)-6,7-dihydro-5H-cyclopenta[c]pyridin-7-yl)propionamide;
(rac)-N-(4-(1-Methyl-2-oxo-1,2,3,4-tetrahydroquinolin-6-yl)-6,7-dihydro-5H-cyclopenta[c]pyridin-7-yl)ethanesulfonamide;
{2-[5-(1-Methyl-2-oxo-1,2,3,4-tetrahydro-quinolin-6-yl)-3,4-dihydro-2H-[1,7]naphthyridin-1-yl]-ethyl}-carbamic acid tert-butyl ester;
6-[1-(2-Amino-ethyl)-1,2,3,4-tetrahydro-[1,7]naphthyridin-5-yl]-1-methyl-3,4-dihydro-1H-quinolin-2-one hydrochloride;
N-{2-[5-(1-Methyl-2-oxo-1,2,3,4-tetrahydro-quinolin-6-yl)-3,4-dihydro-2H-[1,7]naphthyridin-1-yl]-ethyl}-propionamide;
N-(2-(5-(1-Methyl-2-oxo-1,2,3,4-tetrahydroquinolin-6-yl)-3,4-dihydro-1,7-naphthyridin-1(2H)-yl)ethyl)ethanesulfonamide;
and pharmaceutically acceptable salts thereof.

Also particular examples of compounds of formula (I) as described herein are selected from the group consisting of
(2R,S)-2-Hydroxy-N-((4R,S)-4-(1-methyl-2-oxo-1,2,3,4-tetrahydroquinolin-6-yl)-5,6,7,8-tetrahydroisoquinolin-8-yl)propanamide;
(2R)-2-Hydroxy-N-((4R,S)-4-(1-methyl-2-oxo-1,2,3,4-tetrahydroquinolin-6-yl)-5,6,7,8-tetrahydroisoquinolin-8-yl)propanamide;
(2S)-2-Hydroxy-N-((4R,S)-4-(1-methyl-2-oxo-1,2,3,4-tetrahydroquinolin-6-yl)-5,6,7,8-tetrahydroisoquinolin-8-yl)propanamide;
(+)-(2R)-2-Hydroxy-N-((4R or 4S)-4-(1-methyl-2-oxo-1,2,3,4-tetrahydroquinolin-6-yl)-5,6,7,8-tetrahydroisoquinolin-8-yl)propanamide;
(−)-(2R)-2-Hydroxy-N-((4S or 4R)-4-(1-methyl-2-oxo-1,2,3,4-tetrahydroquinolin-6-yl)-5,6,7,8-tetrahydroisoquinolin-8-yl)propanamide;
(−)-(2S)-2-Hydroxy-N-((4S or 4R)-4-(1-methyl-2-oxo-1,2,3,4-tetrahydroquinolin-6-yl)-5,6,7,8-tetrahydroisoquinolin-8-yl)propanamide;
(+)-(2S)-2-Hydroxy-N-((4R or 4S)-4-(1-methyl-2-oxo-1,2,3,4-tetrahydroquinolin-6-yl)-5,6,7,8-tetrahydroisoquinolin-8-yl)propanamide;
(rac)-N-(4-(7-Fluoro-1-methyl-2-oxo-1,2,3,4-tetrahydroquinolin-6-yl)-6,7-dihydro-5H-cyclopenta[c]pyridin-7-yl)propionamide;
(−)-(S or R)—N-(4-(7-Fluoro-1-methyl-2-oxo-1,2,3,4-tetrahydroquinolin-6-yl)-6,7-dihydro-5H-cyclopenta[c]pyridin-7-yl)propionamide;
(+)-(R or S)—N-(4-(7-Fluoro-1-methyl-2-oxo-1,2,3,4-tetrahydroquinolin-6-yl)-6,7-dihydro-5H-cyclopenta[c]pyridin-7-yl)propionamide;
(rac)-N-(4-(7-Fluoro-1-methyl-2-oxo-1,2,3,4-tetrahydroquinolin-6-yl)-6,7-dihydro-5H-cyclopenta[c]pyridin-7-yl)ethanesulfonamide;

(−)-(S or R)—N-(4-(7-Fluoro-1-methyl-2-oxo-1,2,3,4-tetrahydroquinolin-6-yl)-6,7-dihydro-5H-cyclopenta[c]pyridin-7-yl)ethanesulfonamide;
(+)-(R or S)—N-(4-(7-Fluoro-1-methyl-2-oxo-1,2,3,4-tetrahydroquinolin-6-yl)-6,7-dihydro-5H-cyclopenta[c]pyridin-7-yl)ethanesulfonamide;
(rac)-N-[4-(7-Fluoro-1-methyl-2-oxo-1,2,3,4-tetrahydro-quinolin-6-yl)-5,6,7,8-tetrahydro-isoquinolin-8-yl]-propionamide;
(−)-(S or R)—N-[4-(7-Fluoro-1-methyl-2-oxo-1,2,3,4-tetrahydro-quinolin-6-yl)-5,6,7,8-tetrahydro-isoquinolin-8-yl]-propionamide;
(+)-(R or S)—N-[4-(7-Fluoro-1-methyl-2-oxo-1,2,3,4-tetrahydro-quinolin-6-yl)-5,6,7,8-tetrahydro-isoquinolin-8-yl]-propionamide;
(−)-(S or R)-Ethanesulfonic acid [4-(7-fluoro-1-methyl-2-oxo-1,2,3,4-tetrahydro-quinolin-6-yl)-5,6,7,8-tetrahydro-isoquinolin-8-yl]-amide;
(+)-(R or S)-Ethanesulfonic acid [4-(7-fluoro-1-methyl-2-oxo-1,2,3,4-tetrahydro-quinolin-6-yl)-5,6,7,8-tetrahydro-isoquinolin-8-yl]-amide;
(rac)-N-[4-(8-Chloro-1-methyl-2-oxo-1,2,3,4-tetrahydro-quinolin-6-yl)-5,6,7,8-tetrahydro-isoquinolin-8-yl]-propionamide;
(rac)-Ethanesulfonic acid [4-(7-chloro-1-methyl-2-oxo-1,2,3,4-tetrahydro-quinolin-6-yl)-5,6,7,8-tetrahydro-isoquinolin-8-yl]-amide;
N—[(R or S)-4-(7-Chloro-1-methyl-2-oxo-1,2,3,4-tetrahydro-quinolin-6-yl)-5,6,7,8-tetrahydro-isoquinolin-8-yl]-propionamide;
(rac)-Ethanesulfonic acid [4-(8-fluoro-1-methyl-2-oxo-1,2,3,4-tetrahydro-quinolin-6-yl)-5,6,7,8-tetrahydro-isoquinolin-8-yl]-amide;
(rac)-Ethanesulfonic acid [4-(8-chloro-1-methyl-2-oxo-1,2,3,4-tetrahydro-quinolin-6-yl)-5,6,7,8-tetrahydro-isoquinolin-8-yl]-amide;
(+)-Ethanesulfonic acid [(R or S)-4-(8-chloro-1-methyl-2-oxo-1,2,3,4-tetrahydro-quinolin-6-yl)-5,6,7,8-tetrahydro-isoquinolin-8-yl]-amide;
(−)-Ethanesulfonic acid [(S or R)-4-(8-chloro-1-methyl-2-oxo-1,2,3,4-tetrahydro-quinolin-6-yl)-5,6,7,8-tetrahydro-isoquinolin-8-yl]-amide;
(−)-N—[(S or R)-4-(8-Chloro-1-methyl-2-oxo-1,2,3,4-tetrahydro-quinolin-6-yl)-5,6,7,8-tetrahydro-isoquinolin-8-yl]-propionamide;
(+)-N—[(R or S)-4-(8-Chloro-1-methyl-2-oxo-1,2,3,4-tetrahydro-quinolin-6-yl)-5,6,7,8-tetrahydro-isoquinolin-8-yl]-propionamide;
(+)-N-[(7S,8R or 7R,8S)-7-Methyl-4-(1-methyl-2-oxo-1,2,3,4-tetrahydro-quinolin-6-yl)-5,6,7,8-tetrahydro-isoquinolin-8-yl]-propionamide;
(−)-N-[(7S,8S or 7R,8R)-4-(7-Fluoro-1-methyl-2-oxo-1,2,3,4-tetrahydro-quinolin-6-yl)-7-methyl-5,6,7,8-tetrahydro-isoquinolin-8-yl]-propionamide;
(−)-N-[(7R,8S or 7S,8R)-4-(7-Fluoro-1-methyl-2-oxo-1,2,3,4-tetrahydro-quinolin-6-yl)-7-methyl-5,6,7,8-tetrahydro-isoquinolin-8-yl]-propionamide;
(+)-N-[(7S,8R or 7R,8S)-4-(7-Fluoro-1-methyl-2-oxo-1,2,3,4-tetrahydro-quinolin-6-yl)-7-methyl-5,6,7,8-tetrahydro-isoquinolin-8-yl]-propionamide;
(−)-N-[(7S,8S or 7R,8R)-7-Methyl-4-(1-methyl-2-oxo-1,2,3,4-tetrahydro-quinolin-6-yl)-5,6,7,8-tetrahydro-isoquinolin-8-yl]-propionamide;
(−)-N-[(7R,8S or 7S,8R)-7-Methyl-4-(1-methyl-2-oxo-1,2,3,4-tetrahydro-quinolin-6-yl)-5,6,7,8-tetrahydro-isoquinolin-8-yl]-propionamide;
(+)-N-[(7R,8R or 7S,8S)-4-(7-Fluoro-1-methyl-2-oxo-1,2,3,4-tetrahydro-quinolin-6-yl)-7-methyl-5,6,7,8-tetrahydro-isoquinolin-8-yl]-propionamide;
(+)-N-[(7R,8R or 7S,8S)-7-Methyl-4-(1-methyl-2-oxo-1,2,3,4-tetrahydro-quinolin-6-yl)-5,6,7,8-tetrahydro-isoquinolin-8-yl]-propionamide;
(−)-N-[(7R,8R or 7S,8S)-7-Fluoro-4-(1-methyl-2-oxo-1,2,3,4-tetrahydro-quinolin-6-yl)-5,6,7,8-tetrahydro-isoquinolin-8-yl]-propionamide;
(−)-N-[(7S,8R or 7R,8S)-7-Fluoro-4-(1-methyl-2-oxo-1,2,3,4-tetrahydro-quinolin-6-yl)-5,6,7,8-tetrahydro-isoquinolin-8-yl]-propionamide;
(+)-N-[(7S,8S or 7R,8R)-7-Fluoro-4-(1-methyl-2-oxo-1,2,3,4-tetrahydro-quinolin-6-yl)-5,6,7,8-tetrahydro-isoquinolin-8-yl]-propionamide;
(+)-N-[(7R,8S or 7S,8R)-7-Fluoro-4-(1-methyl-2-oxo-1,2,3,4-tetrahydro-quinolin-6-yl)-5,6,7,8-tetrahydro-isoquinolin-8-yl]-propionamide;
(+)-N-[(7S,8S or 7R,8R)-7-Fluoro-4-(7-fluoro-1-methyl-2-oxo-1,2,3,4-tetrahydro-quinolin-6-yl)-5,6,7,8-tetrahydro-isoquinolin-8-yl]-propionamide;
(+)-N-[(7R,8S or 7S,8R)-7-Fluoro-4-(7-fluoro-1-methyl-2-oxo-1,2,3,4-tetrahydro-quinolin-6-yl)-5,6,7,8-tetrahydro-isoquinolin-8-yl]-propionamide;
(−)-N-[(7R,8R or 7S,8S)-7-Fluoro-4-(7-fluoro-1-methyl-2-oxo-1,2,3,4-tetrahydro-quinolin-6-yl)-5,6,7,8-tetrahydro-isoquinolin-8-yl]-propionamide;
(−)-N-[(7S,8R or 7R,8S)-7-Fluoro-4-(7-fluoro-1-methyl-2-oxo-1,2,3,4-tetrahydro-quinolin-6-yl)-5,6,7,8-tetrahydro-isoquinolin-8-yl]-propionamide;
(rac)-N-(4-(8-Chloro-1-methyl-2-oxo-1,2,3,4-tetrahydro-quinolin-6-yl)-6,7-dihydro-5H-cyclopenta[c]pyridin-7-yl)propionamide;
(−)-(S or R)—N-(4-(8-Chloro-1-methyl-2-oxo-1,2,3,4-tetrahydroquinolin-6-yl)-6,7-dihydro-5H-cyclopenta[c]pyridin-7-yl)propionamide;
(+)-(R or S)—N-(4-(8-Chloro-1-methyl-2-oxo-1,2,3,4-tetrahydroquinolin-6-yl)-6,7-dihydro-5H-cyclopenta[c]pyridin-7-yl)propionamide;
(R)-6-(8-Amino-5,6,7,8-tetrahydroisoquinolin-4-yl)-1-methyl-3,4-dihydroquinolin-2(1H)-one;
3-Chloro-pyridine-2-carboxylic acid [(R)-4-(1-methyl-2-oxo-1,2,3,4-tetrahydro-quinolin-6-yl)-5,6,7,8-tetrahydro-isoquinolin-8-yl]-amide;
N—[(R)-4-(1-Methyl-2-oxo-1,2,3,4-tetrahydro-quinolin-6-yl)-5,6,7,8-tetrahydro-isoquinolin-8-yl]-acetamide;
Cyclopropanecarboxylic acid [(R)-4-(1-methyl-2-oxo-1,2,3,4-tetrahydro-quinolin-6-yl)-5,6,7,8-tetrahydro-isoquinolin-8-yl]-amide;
N—[(R)-4-(1-Methyl-2-oxo-1,2,3,4-tetrahydro-quinolin-6-yl)-5,6,7,8-tetrahydro-isoquinolin-8-yl]-methanesulfonamide;
Cyclopropanesulfonic acid [(R)-4-(1-methyl-2-oxo-1,2,3,4-tetrahydro-quinolin-6-yl)-5,6,7,8-tetrahydro-isoquinolin-8-yl]-amide;
(rac)-6-(8-Hydroxy-5,6,7,8-tetrahydro-isoquinolin-4-yl)-1-methyl-3,4-dihydroquinolin-2(1H)-one;
(S or R)-6-(8-Hydroxy-5,6,7,8-tetrahydro-isoquinolin-4-yl)-1-methyl-3,4-dihydroquinolin-2(1H)-one;
(R or S)-6-(8-Hydroxy-5,6,7,8-tetrahydro-isoquinolin-4-yl)-1-methyl-3,4-dihydroquinolin-2(1H)-one;
1-Methyl-6-(8-oxo-5,6,7,8-tetrahydro-isoquinolin-4-yl)-3,4-dihydro-1H-quinolin-2-one;
N-[4-(1-Methyl-2-oxo-1,2,3,4-tetrahydro-quinolin-6-yl)-5,6-dihydro-isoquinolin-8-yl]-propionamide;
(+)-(R)—N-(4-(1-Methyl-2-oxo-1,2,3,4-tetrahydroquinolin-6-yl)-5,6,7,8-tetrahydroisoquinolin-8-yl)propionamide;
and pharmaceutically acceptable salts thereof.

Further particular examples of compounds of formula (I) as described herein are selected from the group consisting of
(+)-N-(4-(1-Methyl-2-oxo-1,2,3,4-tetrahydroquinolin-6-yl)-5,6,7,8-tetrahydroisoquinolin-8-yl)propionamide;
(+)-N-(4-(1-Methyl-2-oxo-1,2,3,4-tetrahydroquinolin-6-yl)-5,6,7,8-tetrahydroisoquinolin-8-yl)ethanesulfonamide;
(+)-N-(4-(1-Methyl-2-oxo-1,2,3,4-tetrahydroquinolin-6-yl)-6,7-dihydro-5H-cyclopenta[c]pyridin-7-yl)propionamide;
(rac)-N-(4-(1-Methyl-2-oxo-1,2,3,4-tetrahydroquinolin-6-yl)-6,7-dihydro-5H-cyclopenta[c]pyridin-7-yl)ethanesulfonamide;
N-{2-[5-(1-Methyl-2-oxo-1,2,3,4-tetrahydro-quinolin-6-yl)-3,4-dihydro-2H-[1,7]naphthyridin-1-yl]-ethyl}-propionamide;
and pharmaceutically acceptable salts thereof.

Also further particular examples of compounds of formula (I) as described herein are selected from the group consisting of
(+)-(R or S)—N-(4-(7-Fluoro-1-methyl-2-oxo-1,2,3,4-tetrahydroquinolin-6-yl)-6,7-dihydro-5H-cyclopenta[c]pyridin-7-yl)propionamide;
(+)-(R or S)—N-(4-(7-Fluoro-1-methyl-2-oxo-1,2,3,4-tetrahydroquinolin-6-yl)-6,7-dihydro-5H-cyclopenta[c]pyridin-7-yl)ethanesulfonamide;
(+)-(R or S)—N-[4-(7-Fluoro-1-methyl-2-oxo-1,2,3,4-tetrahydro-quinolin-6-yl)-5,6,7,8-tetrahydro-isoquinolin-8-yl]-propionamide;
(+)-N—[(R or S)-4-(8-Chloro-1-methyl-2-oxo-1,2,3,4-tetrahydro-quinolin-6-yl)-5,6,7,8-tetrahydro-isoquinolin-8-yl]-propionamide;
(+)-N-[(7S,8R or 7R,8S)-7-Methyl-4-(1-methyl-2-oxo-1,2,3,4-tetrahydro-quinolin-6-yl)-5,6,7,8-tetrahydro-isoquinolin-8-yl]-propionamide;
(+)-N-[(7R,8R or 7S,8S)-4-(7-Fluoro-1-methyl-2-oxo-1,2,3,4-tetrahydro-quinolin-6-yl)-7-methyl-5,6,7,8-tetrahydro-isoquinolin-8-yl]-propionamide;
(+)-N-[(7S,8S or 7R,8R)-7-Fluoro-4-(1-methyl-2-oxo-1,2,3,4-tetrahydro-quinolin-6-yl)-5,6,7,8-tetrahydro-isoquinolin-8-yl]-propionamide;
(+)-(R or S)—N-(4-(8-Chloro-1-methyl-2-oxo-1,2,3,4-tetrahydroquinolin-6-yl)-6,7-dihydro-5H-cyclopenta[c]pyridin-7-yl)propionamide;
3-Chloro-pyridine-2-carboxylic acid [(R)-4-(1-methyl-2-oxo-1,2,3,4-tetrahydro-quinolin-6-yl)-5,6,7,8-tetrahydro-isoquinolin-8-yl]-amide;
N—[(R)-4-(1-Methyl-2-oxo-1,2,3,4-tetrahydro-quinolin-6-yl)-5,6,7,8-tetrahydro-isoquinolin-8-yl]-acetamide;
(+)-(R)—N-(4-(1-Methyl-2-oxo-1,2,3,4-tetrahydroquinolin-6-yl)-5,6,7,8-tetrahydroisoquinolin-8-yl)propionamide;
and pharmaceutically acceptable salts thereof.

A more particular example of compounds of formula (I) as described herein is (+)-(S or R)—N-(4-(1-Methyl-2-oxo-1,2,3,4-tetrahydroquinolin-6-yl)-5,6,7,8-tetrahydroisoquinolin-8-yl)propionamide or a pharmaceutically acceptable salt thereof.

Also a more particular example of compounds of formula (I) as described herein is (+)—(R)—N-(4-(1-Methyl-2-oxo-1,2,3,4-tetrahydroquinolin-6-yl)-5,6,7,8-tetrahydroisoquinolin-8-yl)propionamide or a pharmaceutically acceptable salt thereof.

Processes for the manufacture of compounds of formula (I) as described herein are an object of the invention.

The preparation of compounds of formula (I) of the present invention may be carried out in sequential or convergent synthetic routes. Syntheses of the invention are shown in the following general schemes. The skills required for carrying out the reaction and purification of the resulting products are known to those persons skilled in the art. In case a mixture of enantiomers or diastereoisomers is produced during a reaction, these enantiomers or diastereoisomers can be separated by methods described herein or known to the man skilled in the art such as e.g. chiral chromatography or crystallization. The substituents and indices used in the following description of the processes have the significance given herein.

The following abbreviations are used in the present text:
AcOH=acetic acid, BOC=t-butyloxycarbonyl, BuLi=butyllithium, CDI=1,1-carbonyldiimidazole, $CH_2Cl_2$=dichloromethane, DBU=2,3,4,6,7,8,9,10-octahydro-pyrimido[1,2-a]azepine, DCE=1,2-dichloroethane, DIBALH=di-1-butylaluminium hydride, DCC=N,N'-dicyclohexylcarbodiimide, DCM=dichloromethane, DMA=N,N-dimethylacetamide, DMAP=4-dimethylaminopyridine, DMF=N,N-dimethylformamide, EDCI=N-(3-dimethylaminopropyl)-N'-ethylcarbodiimide hydrochloride, EtOAc=ethylacetate, EtOH=ethanol, $Et_2O$=diethylether, $Et_3N$=triethylamine, eq=equivalents, HATU=O-(7-azabenzotriazol-1-yl)-1,1,3,3-tetramethyluronium hexafluorophosphate, HPLC=high performance liquid chromatography, HOBT=1-hydroxybenzo-triazole, Huenig's base=$iPr_2NEt$=N-ethyl diisopropylamine, IPA=2-propanol, IPC=in process control, LAH=lithium aluminium hydride, LDA=lithium diisopropylamide, $LiBH_4$=lithium borohydride, MeOH=methanol, $NaBH_3CN$, sodium cyanoborohydride, $NaBH_4$=sodium borohydride, NaI=sodium iodide, Red-Al=sodium bis(2-methoxyethoxy) aluminium hydride, RT=room temperature, TBDMSCl=t-butyldimethylsilyl chloride, TFA=trifluoroacetic acid, THF=tetrahydrofuran, quant=quantitative.

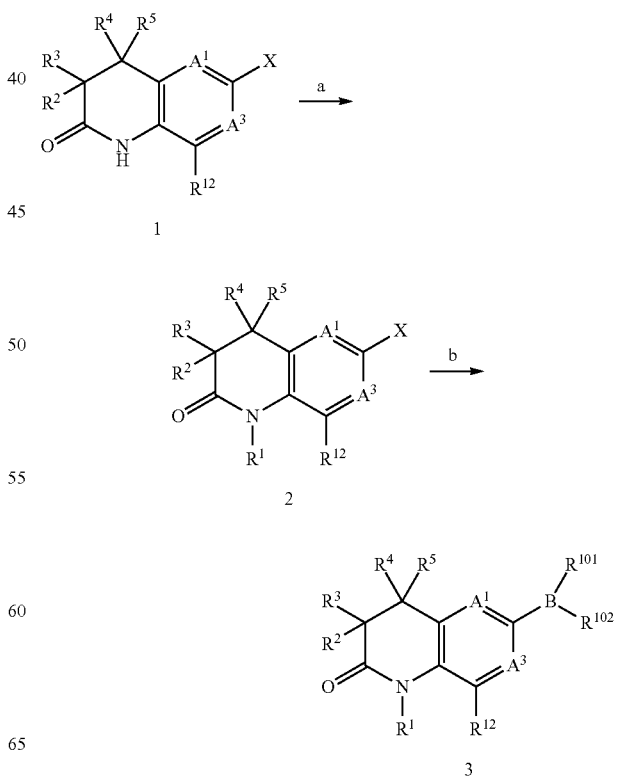

Scheme 1a

-continued

110, 115, 116, 119, 154, 157, 159 or 160

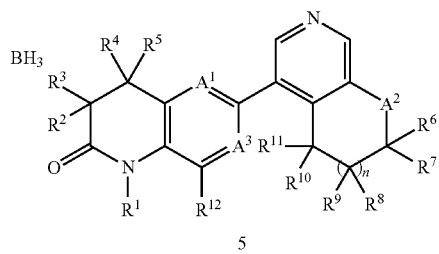

5

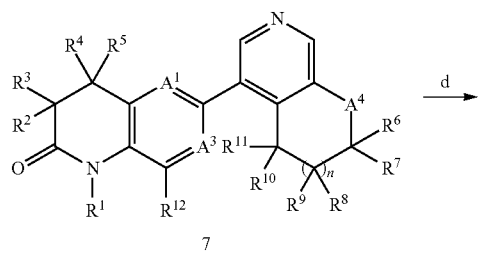

204, 208, 255, 256 or 304

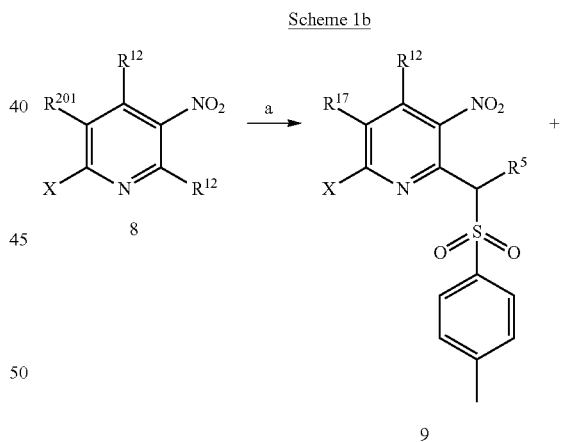

7

5

X is Halogen or OSO$_2$CF$_3$
R$^{101}$ and R$^{102}$ e.g. together with the boron atom to which they are attached form

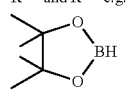

A$^4$ is C(O), NH or N-protecting group as shown is Schemes 2a, 2b, 3a, 3b and 3c.

Lactam compounds 1 (Scheme 1a) are known or can be prepared by methods described herein or known to the man skilled in the art; compounds 1 can be alkylated at nitrogen using a base like sodium hydride or sodium or potassium tert-butoxide, followed by addition of an alkylating agent like an alkyl or cycloalkyl halide, alkyl or cycloalkyl tosylate or an alkyl or cycloalkyl mesylate in a solvent like DMF or THF preferably in a temperature range between 0° C. and about 80° C. giving N-alkylated lactams 2 (step a).

Reaction of lactams 2 with e.g. 4,4,4',4',5,5,5',5'-octamethyl-2,2'-bi(1,3,2-5 dioxaborolane) in solvents like dimethylsulfoxide or dioxane in the presence of potassium acetate and catalysts like (1,1'-bis-diphenylphosphino)-ferrocene) palladium-(II)dichloride (1:1 complex with dichloromethane) at temperatures up to about 100° C. gives boronic ester compounds 3 (step b). Condensation of boronic ester compounds 3 with suitable aryl halides 110, 115, 116, 119, 152, 153, 154, 155, 156, 157, 159, 160, 204, 208, 212, 255, 256 or 304 (for possible syntheses of aryl halides 110, 115, 116, 119, 152, 153, 154, 155, 156, 157, 159, 160, 204, 208, 212, 255, 256 or 304, see Schemes 2a, 2b, 3a, 3b and 3c) can be performed using Suzuki conditions, e.g. in the presence of catalysts, such as tri-o-tolylphosphine/palladium(II)acetate, tetrakis-(triphenylphosphine)-palladium, bis(triphenylphosphine)palladium(II)chloride or dichloro[1,1'-bis(diphenylphosphino)-ferrocene]palladium(II) optionally in the form of a dichloromethane complex (1:1), and in the presence of a base, such as aqueous or non-aqueous potassium phosphate, sodium or potassium carbonate, in a solvent, such as dimethylsulfoxide, toluene, ethanol, dioxane, tetrahydrofuran or N,N-dimethylformamide, and in an inert atmosphere such as argon or nitrogen, in a temperature range preferably between room temperature and about 130° C. leading to adducts 5 or 7 (steps c). Compounds 7 can be further transformed into compounds of the general formula 5 by methods described in the following Schemes, the examples or by methods well known to persons skilled in the art (step d). See also Scheme 1b for alternative syntheses of compounds 5 and 7.

Scheme 1b

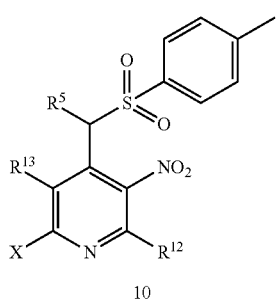

25
-continued
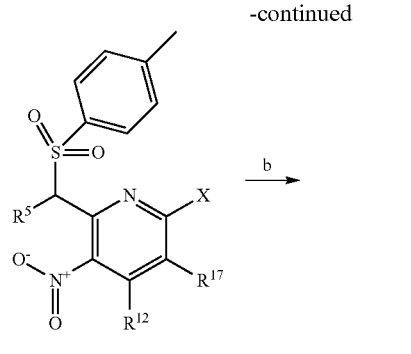
9
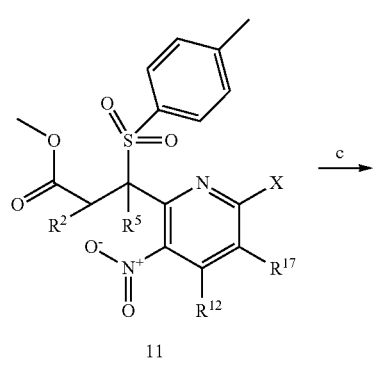
11
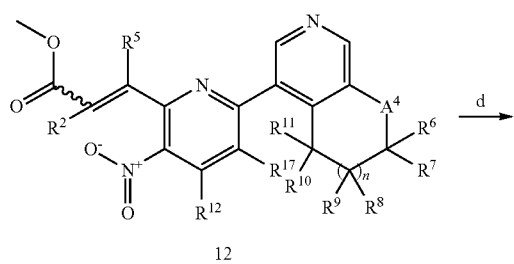
12
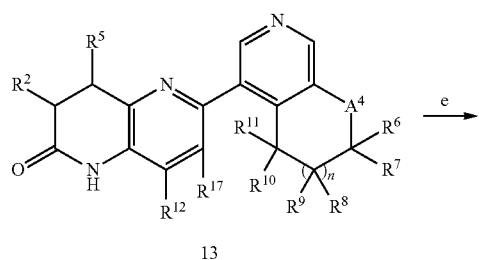
13
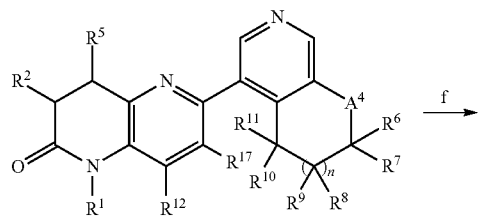
14
26
-continued
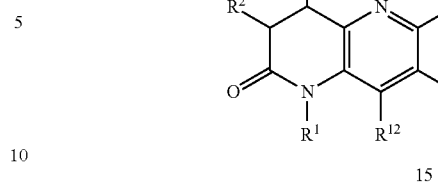
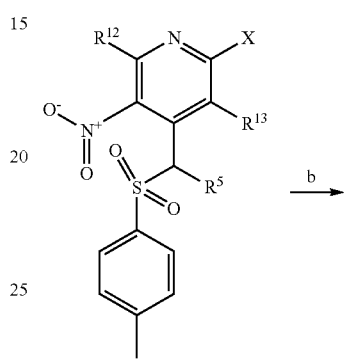
10
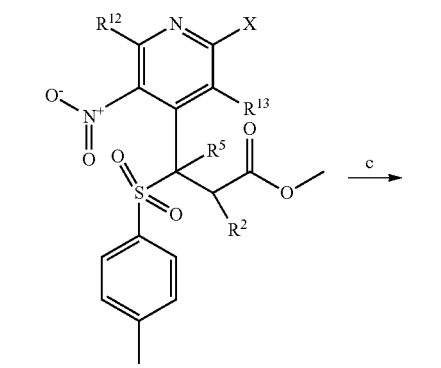
16
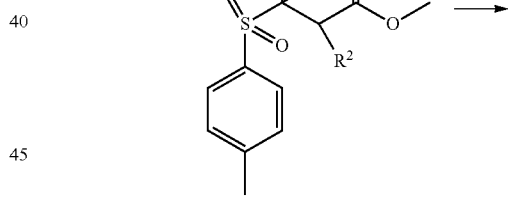
17

-continued

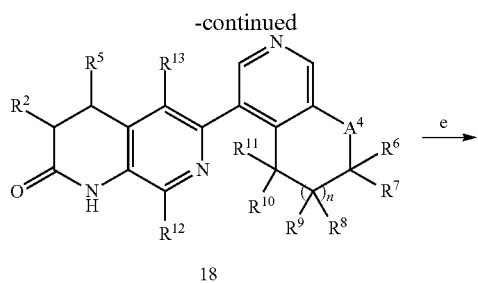

18

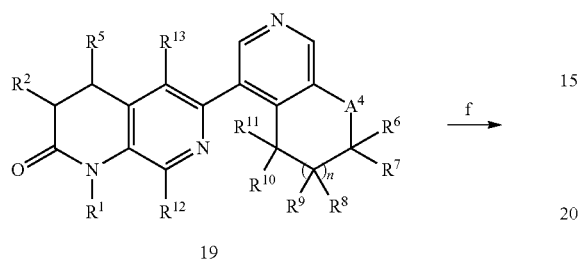

19

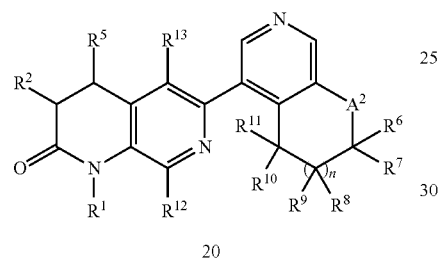

20

X is Halogen or OSO$_2$CF$_3$
A$^4$ is A$^2$, C(O), NH or N-protecting group as shown is Schemes 2a, 2b, 3a, 3b and 3c.
R$^{201}$ is H, halogen, alkyl, haloalkyl, cycloalkyl or halocycloalkyl Halo-nitro pyridine compounds 8 (Scheme 1b) with at least one hydrogen substituent R$^{12}$ ortho to the nitro group react with 1-chloro-1-R$^5$-methanesulfonyl-4-methyl-benzene in solvents like THF and in the presence of a base like tert-BuOK in a temperature range between −78° C. and room temperature to give regioisomeric sulfones 9 and 10 (step a). Treatment of sulfones 9 and 10 with a haloacetic acid ester compound in a solvent like N,N-dimethylformamide and in the presence of a weak base as e.g. sodium or potassium carbonate preferably in a temperature range between room temperature and about 80° C. gives acetic acid ester adducts 11 and 16 (step b). Suzuki reactions of adducts 11 and 16 with suitable hetero biaryl-boronic acid derivatives under conditions as described for step c (Scheme 1a) gives adducts 12 and 17 containing acrylic ester moieties by concomitant elimination of the 4-methyl-benzene-sulfonyl groups (step c). Catalytic hydrogenation e.g. using Pd/C and AcOH in methanol at elevated temperature and with H$_2$ pressure of about 50-200 psi gives lactam compounds 13 and 18 (step d). Treatment of lactam compounds 13 and 18 with an alkylating agent like an alkyl or cycloalkyl halide, alkyl or cycloalkyl tosylate or an alkyl or cycloalkyl mesylate in a solvent like THF or N,N-dimethylformamide in the presence of a base like sodium or potassium hydride preferable around 0° C. gives alkylated lactam compounds 14 and 19 (step e). Alkylated lactam compounds 14 and 19 can be further transformed into compounds of the general formula 15 or 20 by methods described in the following Schemes, the examples or by methods well known to persons skilled in the art (step f).

Scheme 1c

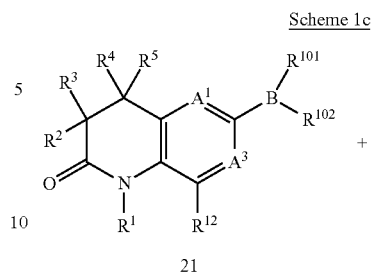

21

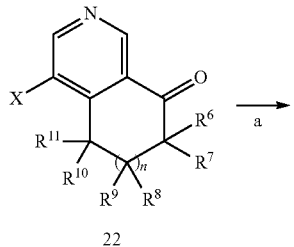

22

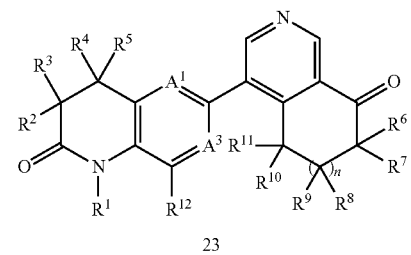

23

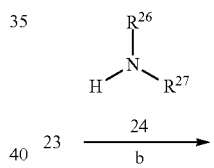

24

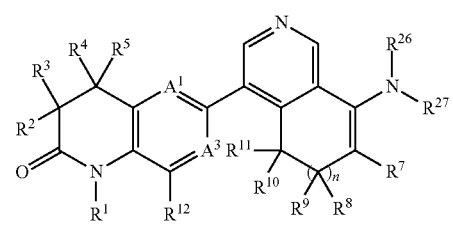

25

R$^{101}$ and R$^{102}$ e.g. together with the boron atom to which they are attached form

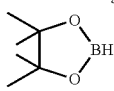

Suzuki reaction between boronic ester compounds 21 and 4-halo-6,7-dihydroisoquinolin-8(5H)-one compounds 22 (Scheme 1c) as described in Scheme 1a, step c, gives cyclic ketone compounds 23 (step a). Treatment of ketone compounds 23 with amino moieties 24 (wherein R$^{27}$ is substituted aryl, substituted heteroaryl, —S(O)$_2$R$^{31}$, —S(O)$_2$OR$^{31}$, —S(O)$_2$NR$^{31}$R$^{32}$, —C(O)R$^{31}$, —C(O)OR$^{31}$ or —C(O)NR$^{31}$R$^{32}$) in solvent like e.g. toluene, trifluorotoluene and a strong acid as e.g. trifluoromethane sulfonic acid at temperatures around 100° C. gives enamino compounds 25 (step b).

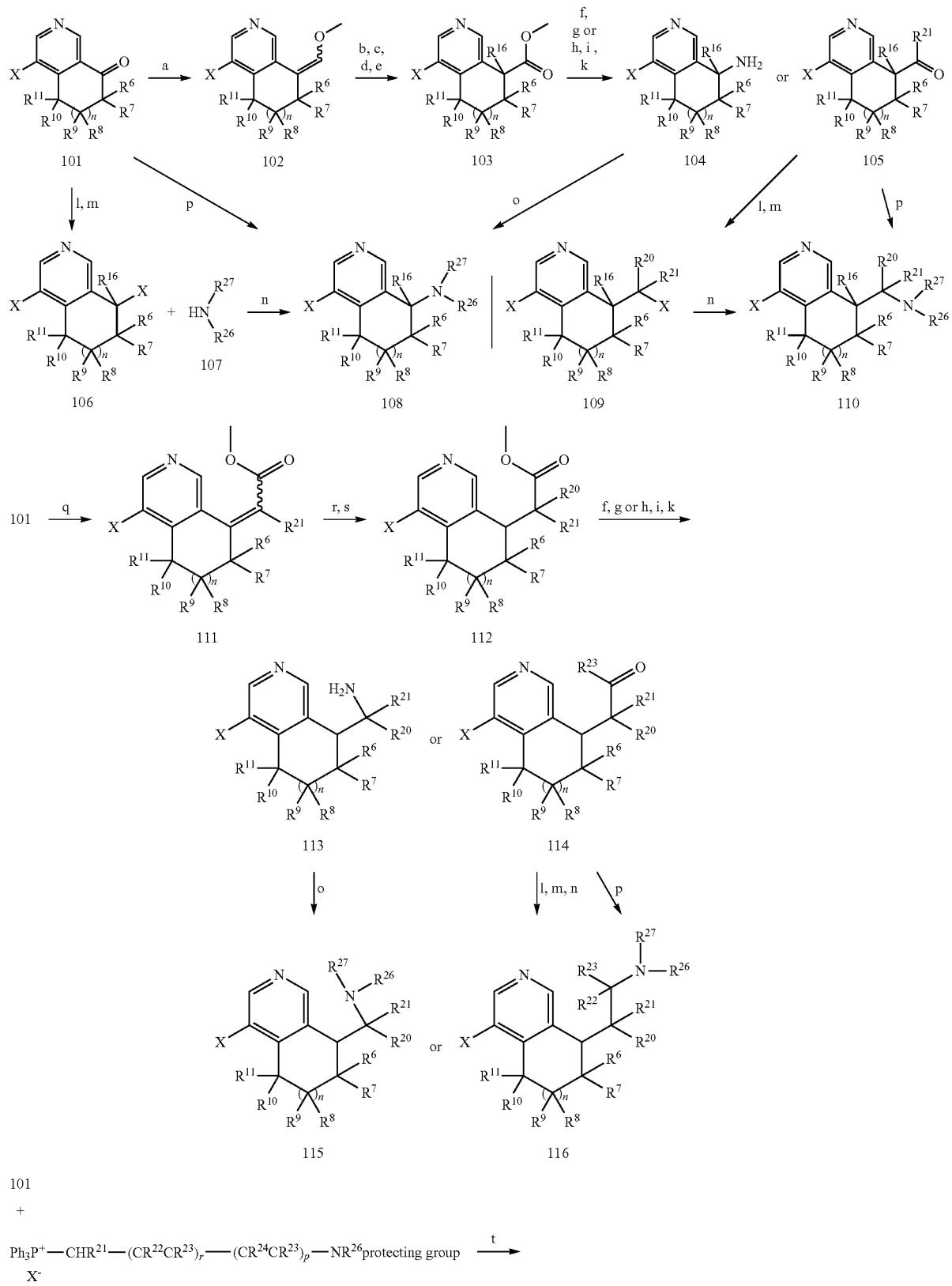

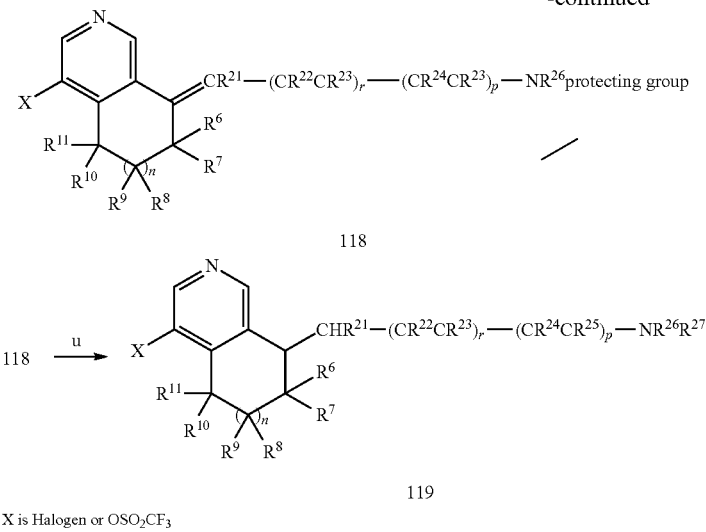

X is Halogen or OSO$_2$CF$_3$

Schemes 2a, 2b, 3a, 3b and 3c describe examples of compounds that can serve as intermediates 110, 115, 116, 119, 152-157, 159, 160, 204, 208, 212, 255, 256 or 304 (Scheme 1a).

Treatment of ketones 101 by a Wittig reaction using (methoxymethyl)-triphenylphosphonium chloride as reagent (step a), subsequent treatment of the Wittig product 102 with acid and oxidation of the aldehyde formed gives the corresponding acids (e.g. using sodium chlorate, sodium dihydrogen-phosphate in a mixture of tert-butanol and water and in the presence of 3-methyl-2-butene at temperatures around room temperature), which can be converted into suitable ester compounds 103 ($R^{16}$=H) (steps b, c, d). Such ester compounds 103 can be treated with a base like LDA or HMDS in solvents like tetrahydrofuran or 1,2-dimethoxyethane, followed by addition of an alkyl halide, mesylate or tosylate, a reaction preferably performed between −78° C. and room temperature to give ester compounds 103 carrying a substituent $R^{16}$ different from H (step e). Ester compounds 103 can be converted into amino compounds 104 via formation of the corresponding primary amides (e.g. by amide formation with ammonia in a suitable solvent as methanol, or by saponification followed by standard amide coupling with ammonia) followed by a Hofmann rearrangement: treatment with sodium hydroxide, and bromine in a solvent like ethanol preferably between about 0° C. and the reflux temperature of the solvent (steps f, g). Substituents $R^{26}$ and $R^{27}$ can then be attached to amino compounds 104 using methods well known to persons skilled in the art substituents, as e.g. described for the conversion of compounds 151 into compounds 152-157, 159 (Scheme 2b) (steps o).

Alternatively, ester compounds 103 can converted into ketones 105 via Weinreb amides: transformation into methoxy-N-methyl-amides followed by reaction with Grignard reagents $R^{21}$MgX or lithium reagents $R^{21}$Li in solvents like THF in a temperature range between −78° C. and room temperature to give ketones 105 (steps h, i, k). Ketones 101 and 105 can react with a hydride reducing agent like sodium borohydride (e.g. in methanol around room temperature) or with a Grignard reagent $R^{16}$MgX or $R^{20}$MgX or with a lithium reagent $R^{16}$Li or $R^{20}$Li n solvents like THF in a temperature range between −78° C. and room temperature to secondary or tertiary alcohol compounds, which can be converted into the corresponding halides, mesylates or tosylates 106 or 109 by methods well known in the art (steps l, m). Halides, mesylates or tosylates 106 or 109 react with amino compounds 107 either per se potentially in the presence of a base like Huenig's base or after anion formation e.g. with sodium hydride in solvents like N,N'-dimethylformamide in a temperature range between 0° C. and about 100° C. to give substituted amino compounds 108 or 110 (step n).

Treatment of ketones 101 by a Horner-Emmons reactions using e.g. reagents like dimethyl(methoxycarbonyl)methylphosphonate, optionally carrying an additional $R^{21}$ substituent at the methylene group, and a base like sodium hydride in a solvent like tetrahydrofuran preferable between about 0° C. and the reflux temperature of the solvent to give unsaturated esters 111 (step q). Reduction of the double bond in unsaturated esters 111 can be performed e.g. by using a mixture of nickel chloride and sodium borohydride as reducing agents in solvents like methanol preferably between about 0° C. and room temperature and is leading to ester compounds 112 ($R^{20}$=H) (step r). Treatment of ester compounds 112 ($R^{20}$=H) with a base like LDA or HMDS in solvents like tetrahydrofuran or 1,2-dimethoxyethane, followed by addition of one or sequentially two different alkyl halides, mesylates or tosylates, a reaction preferably performed between −78° C. and room temperature gives ester compounds 112 ($R^{20}$ not H) (step s). Amide formation and Hofmann degradation or ketone formation via Weinreb amides followed by analogous subsequent transformations as described above gives compounds 113, 114, 115 and 116.

Optionally, suitable reductive amination procedures can convert aldehydes or ketones 101, 105 or 114 into compounds 108, 110 or 116 ($R^{16}$=H, $R^{20}$=H, $R^{22}$=H), e.g. by treatment with suitable amines, e.g. NH$_4$OAc or of formula HNR$^{26}$R$^{27}$, and NaBH(OAc)$_3$ in a one-step procedure in a solvent like methanol preferably around room temperature, or between room temperature and reflux, or in a two-step procedure by first treatment with suitable amines, e.g. ammonia in methanol, and titanium (IV) isopropoxide in solvents like methanol or toluene preferably at temperatures between room temperature and the reflux temperature of the solvents followed by reaction with NaBH$_4$ preferably between 0° C. and room temperature (step p).

Compounds 101 can react with suitable phosphonium salts 117 in a Wittig reaction to olefins 118. Double bond hydrogenation and removal of the protecting group followed by introduction of substituents $R^{27}$ gives compounds 119 (steps t, u).

Compounds 151 react with carboxylic acid chlorides ClC(O)$R^{18}$, chloroformates ClC(O)O$R^{18}$, isocyanates O=C=N$R^{18}$, carbamoyl chlorides ClC(O)N$R^{18}R^{19}$, sulfonyl chlorides —S(O)$_2R^{18}$, as well as with ClS(O)$_2$O$R^{18}$ and ClS(O)$_2$N$R^{18}R^{19}$ to the corresponding acyl- or sulfonyl-com-

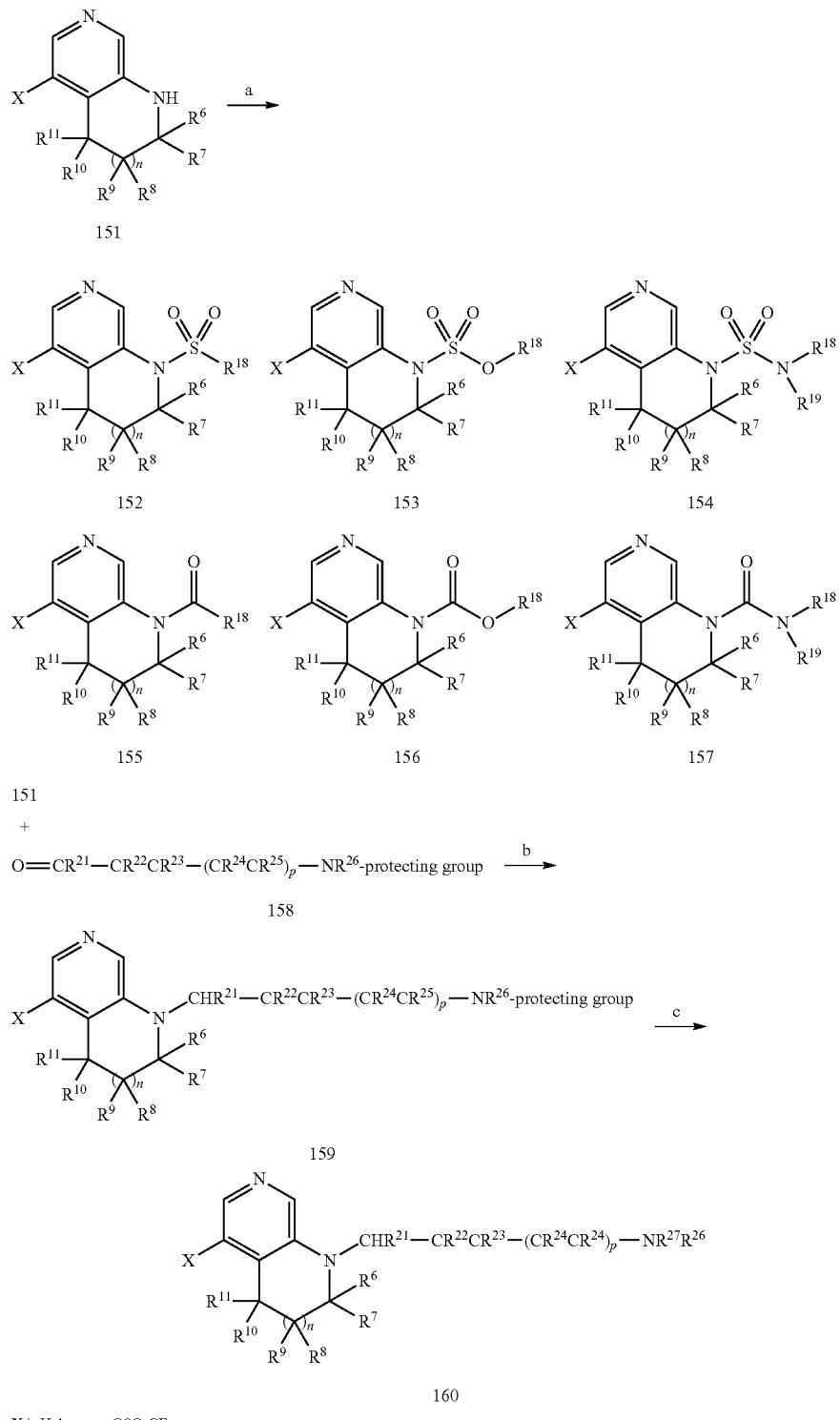

Scheme 2b

X is Halogen or OSO$_2$CF$_3$ pounds 152, 153, 154, 155, 156 and 157 in the presence of a base like triethylamine or Huenig's base (N-ethyl diisopropylamine) in solvents like THF, N,N-dimethylformamide, pyridine and optionally a catalyst like DMAP (4-dimethylaminopyridine) in a temperature range between about 0° C. and the reflux temperature of the solvents (step a). Alternatively, amide compounds 155 can be formed by amide coupling reactions between compounds 151 and acids HOC(O)$R^{18}$ by using well known coupling methods like e.g. using EDCI (N-(3-dimethylaminopropyl)-N'-ethylcarbodiimide hydrochloride), optionally in the presence of HOBT (1-hydroxybenzo-triazole) or DMAP (4-dimethylaminopyridine) and a base like Huenig's base (N-ethyl diisopropylamine) in solvents like N,N-dimethylformamide preferably between 0° C. and room temperature or by use of HATU (O-(7-azabenzotriazol-1-yl)-1,1,3,3-tetramethyluronium hexafluorophosphate), triethylamine, in N,N-dimethylformamide preferably between 0° C. and room temperature (step a).

Suitable reductive amination procedures convert amino compounds 151 and aldehydes or ketones 158 into compounds 159, e.g. by treatment with a reducing agent such as pyridine-$BH_3$ complex, $NaBH(OAc)_3$ or $NaCNBH_3$ under acidic conditions (e.g., acetic acid, formic acid), by using a Lewis acid (e.g., $Ti(iPrO)_4$, $ZnCl_2$) or under buffered conditions, e.g., in the presence of acetic acid and a tertiary amine like N-ethyl-diisopropylamine or triethylamine, in a suitable solvent such as dichloromethane (DCM), dichloroethane, ethanol or isopropanol (or mixtures thereof) at ambient or elevated temperatures using conventional heating or heating by microwave irradiation (step b). Removal of the protecting group in compounds 159 followed by introduction of substituents $R^{27}$ gives compounds 160 (steps b, c).

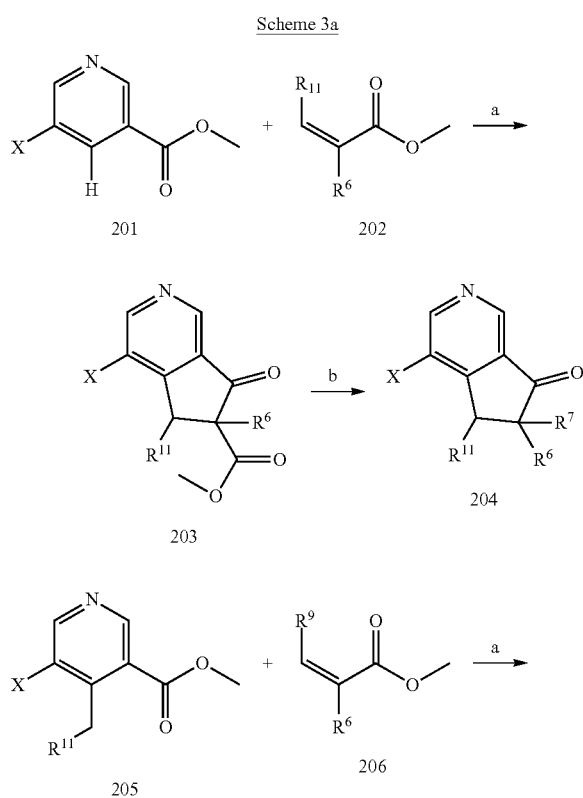

Scheme 3a

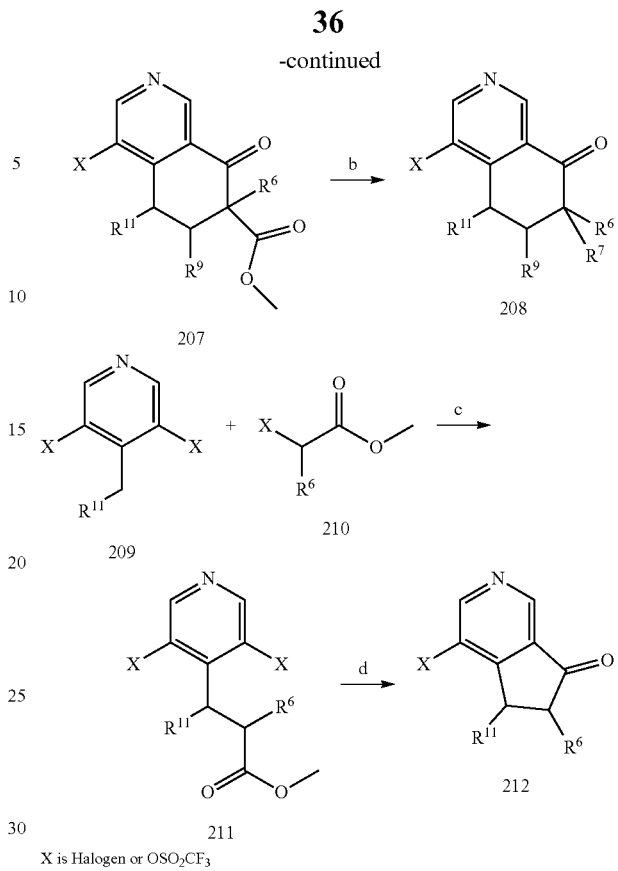

X is Halogen or $OSO_2CF_3$

5-Halo-nicotinic acid compounds 201 or 205 (Scheme 3a) react with acrylic acid ester compounds 202 or 206 after deprotonation with base like LDA or LiHMDS in solvents like THF preferably around −78° C. giving cyclic beta keto ester compounds 203 and 207 (step a). Ester compounds 203 or 207 with $R^6$=H can be treated with a base like NaH, LDA or LiHMDS in solvents like DMF, tetrahydrofuran or 1,2-dimethoxyethane, followed by addition of an alkyl or cycloalkyl halide, mesylate or tosylate, or e.g. a N-halobenzensulfonamide, a reaction preferably performed between −78° C. and room temperature, to give ester compounds 203 or 207 carrying a substituent $R^6$ different from H. Treatment of beta keto-ester compounds 203 or 207 with aqueous acid preferably at reflux induces ester hydrolysis and subsequent decarboxylation providing ketones 204 and 208 (step b). Ketones 204 and 208 with $R^6$=H and/or $R^7$=H can be treated with a base like NaH, LDA or LiHMDS in solvents like DMF, tetrahydrofuran or 1,2-dimethoxyethane, followed by addition of one or subsequently two different alkyl or cycloalkyl halides, mesylates or tosylates, or e.g. N-halobenzensulfonamides, a reaction preferably performed between −78° C. and room temperature, to give ketones 204 and 208 carrying at least one of the substituents $R^6$ or $R^7$ different from H. Optionally, ketones 204 and 208 can be converted into the corresponding imines (e.g. with N-butylamine by using a catalyst like toluene sulfonic acid or pyridinum p-toluenesulfonate in a solvent like ethanol preferably at reflux); such imines with $R^7$=H can be reacted with e.g. N-fluorobenzenesulfonimide using $K_2CO_3$ or triethylamine as base in solvents like DMF or acetonitrile or mixtures thereof, in the presence of molecular sieves preferably at room temperature to give imines carrying fluoro substituents, and after imine hydrolysis (e.g. with hydrochloric acid in acetonitrile)

ketones 204 and 208 with R⁷=F. Treatment of dihalopyridine compounds 209 with a base like LDA or LiHMDS in solvents like tetrahydrofuran or 1,2-dimethoxyethane, followed by addition a halo-acetic acid derivative 210, a reaction preferably performed between −78° C. and room temperature, gives pyridine linked ester compounds 211 (step c). Cyclisation of compounds 211 to compounds 212 can be performed by reaction with e.g. n-butyl lithium in solvents like tetrahydrofuran or 1,2-dimethoxyethane preferably performed between −78° C. and room temperature (step d).

a protecting group (step b, c). Standard BOC removal or use of tetrabutylammonium fluoride hydrate, acetonitrile preferably between room temperature and the reflux temperature of acetonitrile then gives bicyclic compounds 256 (step d).

Scheme 3b

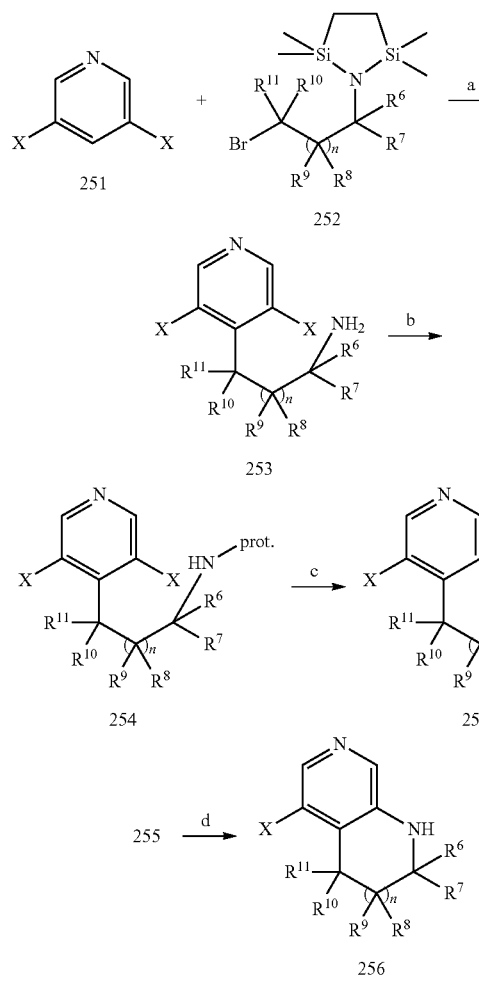

prot. = protecting group

Scheme 3c

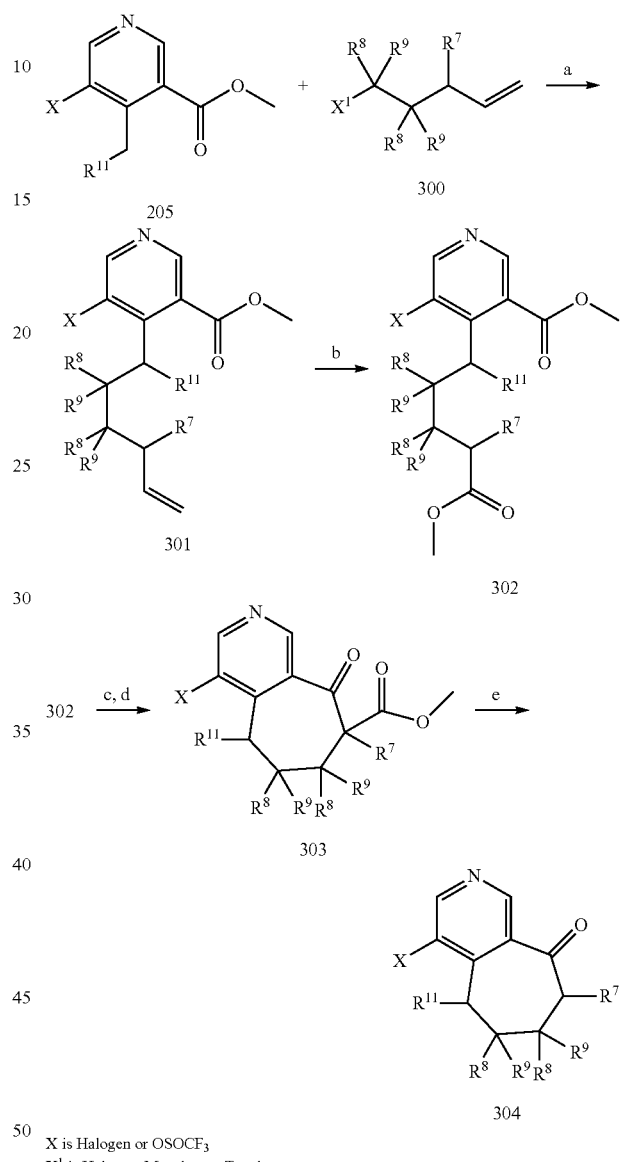

X is Halogen or OSOCF₃
X¹ is Halogen, Mesylate or Tosylate

Dihalopyridine compounds 251 (Scheme 3b) react with bromo-tetramethyl-azadisilolidine reagents 252 after deprotonation with lithium diisopropyl amide in solvents like tetrahydrofuran between −78° C. and 0° C. to give aminoalkyl substituted pyridines 253 (step a). After attachment of a protecting group onto compounds 253 (e.g. by introducing a BOC- or a SES-protecting group by reaction with BOC₂O or 2-trimethylsilanyl-ethanesulfonyl chloride, triethylamine, DMF around and 0° C.), treatment of amino protected pyridine compounds 254 with a base like potassium carbonate, in a solvent like toluene, and in the presence of a catalyst like tetrakis-(triphenylphosphine)-palladium at temperatures around 100° C. gives bicyclic compounds 255, still carrying 5-Halo-nicotinic acid compounds 205 (Scheme 3c) react with alkene compounds 300 after deprotonation with a base like LDA or LiHMDS in solvents like THF preferably around −78° C. giving alkenes 301 (step a). Diester compounds 302 can be synthesized by methods known to persons skilled in the art such as e.g. by ozonolysis of alkenes 301 in the presence of methanolic NaOH to give compounds 302 (step b) which can be cyclized using Dieckmann condensation conditions to give beta keto-ester compounds 303 (step c). Treatment of beta keto-ester compounds 303 with aqueous acid preferably at reflux temperature induces ester hydrolysis and subsequent decarboxylation providing ketones 304 (step e). Ester compounds 303 can be treated with a base like NaH, LDA or LiHMDS in solvents like DMF, tetrahydrofuran or 1,2-dimethoxyethane, followed by addition of an alkyl or cycloalkyl halide, mesylate or tosylate, or e.g. a N-halobenzensulfonamide, a reaction preferably performed between −78° C. and room temperature, to give ester compounds 303 carrying a substituent $R^7$ different from H (step d). Hydrolyses and decarboxylation as described above gives ketones 304 (step e).

Also an embodiment of the present invention is a process to prepare a compound of formula (I) as defined above comprising the reaction of a compound of formula (II) in the presence of a compound of formula (III);

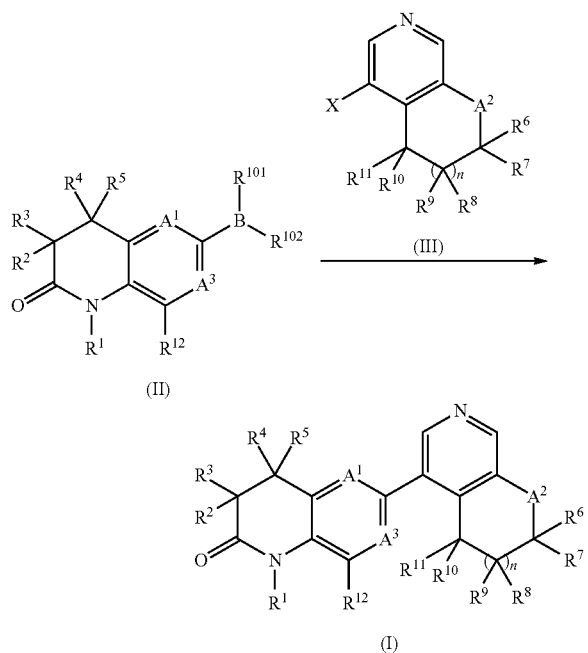

wherein $A^1$, $A^2$, $A^3$, $R^1$, $R^2$, $R^3$, $R^4$, $R^5$, $R^6$, $R^7$, $R^8$, $R^9$, $R^{10}$, $R^{11}$, $R^{12}$ and n are as defined above and wherein X is halogen or triflate, $R^{101}$ and $R^{102}$ are alkyl, cycloalkyl or together with the boron atom they are attached to form together a borolanyl.

In particular in the presence of catalysts, such as tri-o-tolylphosphine/palladium(II)acetate, tetrakis-(triphenylphosphine)-palladium, bis(triphenylphosphine)palladium(II)chloride or dichloro[1,1'-bis(diphenylphosphino)-ferrocene]palladium(II) optionally in the form of a dichloromethane complex (1:1), and in the presence of a base, such as aqueous or non-aqueous potassium phosphate, sodium or potassium carbonate, in a solvent, such as dimethylsulfoxide, toluene, ethanol, dioxane, tetrahydrofuran or N,N-dimethylformamide, and in an inert atmosphere such as argon or nitrogen, in a temperature range particularly between room temperature and about 130° C.

Also an object of the present invention is a compound according to formula (I) as described herein for use as therapeutically active substance.

Also an object of the present invention is a compound according to formula (I) as described herein for use as therapeutically active substance, wherein said compound is (+)-(R)—N-(4-(1-Methyl-2-oxo-1,2,3,4-tetrahydroquinolin-6-yl)-5,6,7,8-tetrahydroisoquinolin-8-yl)propionamide or pharmaceutically acceptable salts thereof.

Likewise an object of the present invention is a pharmaceutical composition comprising a compound according to formula (I) as described herein and a therapeutically inert carrier.

Likewise an object of the present invention is a pharmaceutical composition comprising a compound according to formula (I) as described herein and a therapeutically inert carrier, wherein said compound is (+)-(R)—N-(4-(1-Methyl-2-oxo-1,2,3,4-tetrahydroquinolin-6-yl)-5,6,7,8-tetrahydroisoquinolin-8-yl)propionamide or a pharmaceutically acceptable salt thereof.

The present invention also relates to the use of a compound according to formula (I) as described herein for the treatment or prophylaxis of chronic kidney disease, congestive heart failure, hypertension, primary aldosteronism and Cushing syndrome.

The present invention also relates to the use of a compound according to formula (I) as described herein for the treatment or prophylaxis of diabetic nephropathy.

The present invention also relates to the use of a compound according to formula (I) as described herein for the treatment or prophylaxis of kidney or heart fibrosis.

The present invention also relates to the use of a compound according to formula (I) as described herein for the treatment or prophylaxis of chronic kidney disease, congestive heart failure, primary aldosteronism and Cushing syndrome, wherein said compound is (+)-(R)—N-(4-(1-Methyl-2-oxo-1,2,3,4-tetrahydroquinolin-6-yl)-5,6,7,8-tetrahydroisoquinolin-8-yl)propionamide or pharmaceutically acceptable salts thereof.

The present invention also relates to the use of a compound according to formula (I) as described herein for the treatment or prophylaxis of diabetic nephropathy, wherein said compound is (+)-(R)—N-(4-(1-Methyl-2-oxo-1,2,3,4-tetrahydroquinolin-6-yl)-5,6,7,8-tetrahydroisoquinolin-8-yl)propionamide or pharmaceutically acceptable salts thereof.

The present invention also relates to the use of a compound according to formula (I) as described herein for the treatment or prophylaxis of kidney or heart fibrosis, wherein said compound is (+)-(R)—N-(4-(1-Methyl-2-oxo-1,2,3,4-tetrahydroquinolin-6-yl)-5,6,7,8-tetrahydroisoquinolin-8-yl)propionamide or pharmaceutically acceptable salts thereof.

The present invention also relates to the use of a compound according to formula (I) as described herein for the treatment or prophylaxis of chronic kidney disease.

The present invention also relates to the use of a compound according to formula (I) as described herein for the treatment or prophylaxis of congestive heart failure.

The present invention also relates to the use of a compound according to formula (I) as described herein for the treatment or prophylaxis of hypertension.

The present invention also relates to the use of a compound according to formula (I) as described herein for the treatment or prophylaxis of primary aldosteronism.

A particular embodiment of the present invention is a compound according to formula (I) as described herein for the treatment or prophylaxis of chronic kidney disease, congestive heart failure, hypertension, primary aldosteronism and Cushing syndrome.

Also a particular embodiment of the present invention is a compound according to formula (I) as described herein for the treatment or prophylaxis of diabetic nephropathy.

Another particular embodiment of the present invention is a compound according to formula (I) as described herein for the treatment or prophylaxis of kidney or heart fibrosis.

A particular embodiment of the present invention is a compound according to formula (I) as described herein for the treatment or prophylaxis of chronic kidney disease, congestive heart failure, hypertension, primary aldosteronism and Cushing syndrome, wherein said compound is (+)-(R)—N-

(4-(1-Methyl-2-oxo-1,2,3,4-tetrahydroquinolin-6-yl)-5,6,7,8-tetrahydroisoquinolin-8-yl)propionamide or pharmaceutically acceptable salts thereof.

A particular embodiment of the present invention is a compound according to formula (I) as described herein for the treatment or prophylaxis of diabetic nephropathy, wherein said compound is (+)-(R)—N-(4-(1-Methyl-2-oxo-1,2,3,4-tetrahydroquinolin-6-yl)-5,6,7,8-tetrahydroisoquinolin-8-yl)propionamide or pharmaceutically acceptable salts thereof.

A particular embodiment of the present invention is a compound according to formula (I) as described herein for the treatment or prophylaxis of kidney or heart fibrosis, wherein said compound is (+)-(R)—N-(4-(1-Methyl-2-oxo-1,2,3,4-tetrahydroquinolin-6-yl)-5,6,7,8-tetrahydroisoquinolin-8-yl)propionamide or pharmaceutically acceptable salts thereof. Also a particular embodiment of the present invention is a compound according to formula (I) as described herein for the treatment or prophylaxis of chronic kidney disease.

Also a particular embodiment of the present invention is a compound according to formula (I) as described herein for the treatment or prophylaxis of congestive heart failure.

Also a particular embodiment of the present invention is a compound according to formula (I) as described herein for the treatment or prophylaxis of hypertension.

Also a particular embodiment of the present invention is a compound according to formula (I) as described herein for the treatment or prophylaxis of primary aldosteronism.

The present invention also relates to the use of a compound according to formula (I) as described herein for the preparation of a medicament for the treatment or prophylaxis of chronic kidney disease, congestive heart failure, hypertension, primary aldosteronism and Cushing syndrome.

The present invention also relates to the use of a compound according to formula (I) as described herein for the preparation of a medicament for the treatment or prophylaxis of diabetic nephropathy.

The present invention also relates to the use of a compound according to formula (I) as described herein for the preparation of a medicament for the treatment or prophylaxis of kidney or heart fibrosis.

The present invention also relates to the use of a compound according to formula (I) as described herein for the preparation of a medicament for the treatment or prophylaxis of chronic kidney disease, congestive heart failure, hypertension, primary aldosteronism and Cushing syndrome, wherein said compound is (+)-(R)—N-(4-(1-Methyl-2-oxo-1,2,3,4-tetrahydroquinolin-6-yl)-5,6,7,8-tetrahydroisoquinolin-8-yl)propionamide or pharmaceutically acceptable salts thereof.

The present invention also relates to the use of a compound according to formula (I) as described herein for the preparation of a medicament for the treatment or prophylaxis of diabetic nephropathy, wherein said compound is (+)-(R)—N-(4-(1-Methyl-2-oxo-1,2,3,4-tetrahydroquinolin-6-yl)-5,6,7,8-tetrahydroisoquinolin-8-yl)propionamide or pharmaceutically acceptable salts thereof.

The present invention also relates to the use of a compound according to formula (I) as described herein for the preparation of a medicament for the treatment or prophylaxis of kidney or heart fibrosis, wherein said compound is (+)-(R)—N-(4-(1-Methyl-2-oxo-1,2,3,4-tetrahydroquinolin-6-yl)-5,6,7,8-tetrahydroisoquinolin-8-yl)propionamide or pharmaceutically acceptable salts thereof.

Also an embodiment of the present invention is the use of a compound according to formula (I) as described herein for the preparation of a medicament for the treatment or prophylaxis of chronic kidney disease.

Also an embodiment of the present invention is the use of a compound according to formula (I) as described herein for the preparation of a medicament for the treatment or prophylaxis of congestive heart failure.

Also an embodiment of the present invention is the use of a compound according to formula (I) as described herein for the preparation of a medicament for the treatment or prophylaxis of hypertension.

Also an embodiment of the present invention is the use of a compound according to formula (I) as described herein for the preparation of a medicament for the treatment or prophylaxis of primary aldosteronism.

Also an object of the invention is a method for the treatment or prophylaxis of chronic kidney disease, congestive heart failure, hypertension, primary aldosteronism and Cushing syndrome, which method comprises administering an effective amount of a compound according to formula (I) as described herein.

Also an object of the invention is a method for the treatment or prophylaxis of diabetic nephropathy, which method comprises administering an effective amount of a compound according to formula (I) as described herein.

Also an object of the invention is a method for the treatment or prophylaxis of kidney or heart fibrosis, which method comprises administering an effective amount of a compound according to formula (I) as described herein.

Also an object of the invention is a method for the treatment or prophylaxis of chronic kidney disease, congestive heart failure, hypertension, primary aldosteronism and Cushing syndrome, which method comprises administering an effective amount of a compound according to formula (I) as described herein, wherein said compound is (+)-(R)—N-(4-(1-Methyl-2-oxo-1,2,3,4-tetrahydroquinolin-6-yl)-5,6,7,8-tetrahydroisoquinolin-8-yl)propionamide or pharmaceutically acceptable salts thereof.

Also an object of the invention is a method for the treatment or prophylaxis of diabetic nephropathy, which method comprises administering an effective amount of a compound according to formula (I) as described herein, wherein said compound is (+)-(R)—N-(4-(1-Methyl-2-oxo-1,2,3,4-tetrahydroquinolin-6-yl)-5,6,7,8-tetrahydroisoquinolin-8-yl)propionamide or pharmaceutically acceptable salts thereof.

Also an object of the invention is a method for the treatment or prophylaxis of kidney or heart fibrosis, which method comprises administering an effective amount of a compound according to formula (I) as described herein, wherein said compound is (+)-(R)—N-(4-(1-Methyl-2-oxo-1,2,3,4-tetrahydroquinolin-6-yl)-5,6,7,8-tetrahydroisoquinolin-8-yl)propionamide or pharmaceutically acceptable salts thereof.

Also an embodiment of the present invention is a method for the treatment or prophylaxis of chronic kidney disease, which method comprises administering an effective amount of a compound according to formula (I) as described herein.

Also an embodiment of the present invention is a method for the treatment or prophylaxis of congestive heart failure, which method comprises administering an effective amount of a compound according to formula (I) as described herein.

Also an embodiment of the present invention is a method for the treatment or prophylaxis of hypertension, which method comprises administering an effective amount of a compound according to formula (I) as described herein.

Also an embodiment of the present invention is a method for the treatment or prophylaxis of primary aldosteronism, which method comprises administering an effective amount of a compound according to formula (I) as described herein.

Also an embodiment of the present invention is a compound of formula (I) as described herein, when manufactured according to any one of the described processes.

Assay Procedures

Herein we identified the use of the G-402 cell line as a host cell to ectopically express (transiently or stably) enzymes of the CYP11 family. Specifically we developed stable G-402 cells expressing ectopically human CYP11B1, human CYP11B2, human CYP11A1, cynomolgus CYP11B1 or cynomolgus CYP11B2 enzyme activity. Importantly the identified cell line G-402 expresses co-factors (adrenodoxin and adrenodoxin reductase) important for the activity of the CYP11 family and no relevant enzyme activity of the CYP11 family (in comparison to H295R cells) was detected in these cells. Therefore the G-402 cell line is uniquely suited as a host cell for the ectopic expression of enzymes from the CYP11 family.

G-402 cells can be obtained from ATCC(CRL-1440) and were originally derived from a renal leiomyoblastoma.

The expression plasmids contains the ORF for either human/cyno CYP11B1 or CYP11B2 under the control of a suitable promoter (CMV-promoter) and a suitable resistance marker (neomycin). Using standard techniques the expression plasmid is transfected into G-402 cells and these cells are then selected for expressing the given resistance markers. Individual cell-clones are then selected and assessed for displaying the desired enzymatic activity using 11-Deoxycorticosterone (Cyp11B2) or 11-Deoxycortisol (Cyp11B1) as a substrate.

G-402 cells expressing CYP11 constructs were established as described above and maintained in McCoy's 5a Medium Modified, ATCC Catalog No. 30-2007 containing 10% FCS and 400 μg/ml G418 (Geneticin) at 37° C. under an atmosphere of 5% CO2/95% air. Cellular enzyme assays were performed in DMEM/F12 medium containing 2.5% charcoal treated FCS and appropriate concentration of substrate (0.3-10 uM 11-Deoxycorticosterone, 11-Deoxycortisol or Corticosterone). For assaying enzymatic activity, cells were plated onto 96 well plates and incubated for 16 h. An aliquot of the supernatant is then transferred and analyzed for the concentration of the expected product (Aldosterone for CYP11B2; Cortisol for CYP11B1). The concentrations of these steroids can be determined using HTRF assays from CisBio analyzing either Aldosterone or Cortisol.

Inhibition of the release of produced steroids can be used as a measure of the respective enzyme inhibition by test compounds added during the cellular enzyme assay. The dose dependent inhibition of enzymatic activity by a compound is calculated by means of plotting added inhibitor concentrations x-axes) vs. measured steroid/product level (y-axes). The inhibition is then calculated by fitting the following 4-parameter sigmoidal function (Morgan-Mercer-Flodin (MMF) model) to the raw data points using the least squares method:

$$y = \frac{AB + Cx^D}{B + x^D}$$

wherein, A is the maximum y value, B is the EC50 factor determined using XLFit, C is the minimum y value and D is the slope value.

The maximum value A corresponds to the amount of steroid produced in the absence of an inhibitor, the value C corresponds to the amount of steroid detected when the enzyme is fully inhibited.

EC50 values for compounds claimed herein were tested with the G402-based assay system described. Cyp11B2 enzyme activity was tested in presence of 1 μM Deoxycorticosterone and variable amounts of inhibitors; Cyp11B1 enzyme activity was tested in presence of 1 μM Deoxycortisol and variable amounts of inhibitors.

| Example | EC50 human CYP11B2 μM | EC50 human CYP11B1 μM |
| --- | --- | --- |
| 1 | 0.030 | 2.37 |
| 2 | 1.020 | 12.12 |
| 3 | 0.014 | 0.98 |
| 3-1 | 0.014 | 0.98 |
| 4 | 0.097 | 4.92 |
| 5 | 1.287 | 11.85 |
| 6 | 0.048 | 1.75 |
| 7 | 0.012 | 1.11 |
| 9 | 0.013 | 0.57 |
| 10 | 0.059 | 4.17 |
| 11 | 0.023 | 0.42 |
| 12 | 0.004 | 1.88 |
| 13 | 0.014 | 1.81 |
| 14 | 0.011 | 0.21 |
| 15 | 0.0773 | 0.5738 |
| 16 | 0.0308 | 1.0524 |
| 17 | 0.0316 | 0.8851 |
| 18 | 0.0279 | 1.4893 |
| 19 | 0.493 | 13.2014 |
| 20 | 0.8234 | 25.4873 |
| 21 | 0.028 | 0.5979 |
| 22 | 0.0102 | 1.2012 |
| 23 | 1.3779 | |
| 24 | 0.0038 | 0.4663 |
| 25 | 0.0334 | 2.9822 |
| 26 | 4.5516 | |
| 27 | 0.0112 | 1.8854 |
| 28 | 0.0749 | 6.8159 |
| 29 | 1.7916 | 42.551 |
| 30 | 0.03 | 3.683 |
| 31 | 1.0353 | 14.4935 |
| 32 | 0.0782 | 4.2438 |
| 33 | 0.0798 | 11.5797 |
| 34 | 0.3859 | 34.7195 |
| 35 | 1.7737 | |
| 36 | 0.2388 | 20.7493 |
| 37 | 0.1993 | 13.4626 |
| 38 | 0.422 | 15.9147 |
| 39 | 0.1303 | |
| 40 | 0.1255 | |
| 41 | 0.0166 | 3.5316 |
| 42 | 0.0145 | 0.5236 |
| 43 | 0.4522 | 32.0002 |
| 44 | 0.5288 | 2.0486 |
| 45 | 0.0549 | 2.6176 |
| 46 | 0.4666 | 19.3261 |
| 47 | 1.824 | |
| 48 | 0.0261 | 2.8786 |
| 49 | 0.0442 | 3.9499 |
| 50 | 4.3249 | |
| 51 | 1.4652 | 32.2976 |
| 52 | 0.0258 | 1.5939 |
| 53 | 0.122 | 3.568 |
| 54 | 0.0388 | 2.3897 |
| 55 | 0.1575 | 2.7561 |
| 56 | 2.7774 | 14.9483 |
| 57 | 0.8836 | 20.3224 |
| 58 | 0.0446 | 7.6039 |
| 59 | 3.2948 | |
| 60 | 0.0088 | 1.1736 |
| 61 | 0.0056 | 0.4499 |
| 62 | 0.0053 | 0.5585 |
| 63 | 0.0048 | 1.1942 |
| 64 | 0.0462 | 2.3598 |
| 65 | 0.017 | 1.9268 |
| 66 | 0.0355 | 0.3188 |
| 67 | 0.0047 | 0.2061 |
| 68 | 0.0774 | 1.6223 |

| Example | EC50 human CYP11B2 µM | EC50 human CYP11B1 µM |
|---------|----------------------|----------------------|
| 69 | 0.002 | 0.0541 |
| 70 | 0.0157 | 7.1735 |

Compounds of formula (I) and their pharmaceutically acceptable salts or esters thereof as described herein have $EC_{50}$ (CYP11B2) values between 0.000001 uM and 1000 uM, particular compounds have $EC_{50}$ (CYP11B2) values between 0.00005 uM and 500 uM, further particular compounds have $EC_{50}$ (CYP11B2) values between 0.0005 uM and 5 uM. These results have been obtained by using the described enzymatic assay.

The compounds of formula (I) and their pharmaceutically acceptable salts can be used as medicaments (e.g. in the form of pharmaceutical preparations). The pharmaceutical preparations can be administered internally, such as orally (e.g. in the form of tablets, coated tablets, dragées, hard and soft gelatin capsules, solutions, emulsions or suspensions), nasally (e.g. in the form of nasal sprays) or rectally (e.g. in the form of suppositories). However, the administration can also be effected parentally, such as intramuscularly or intravenously (e.g. in the form of injection solutions).

The compounds of formula (I) and their pharmaceutically acceptable salts can be processed with pharmaceutically inert, inorganic or organic adjuvants for the production of tablets, coated tablets, dragées and hard gelatin capsules. Lactose, corn starch or derivatives thereof, talc, stearic acid or its salts etc. can be used, for example, as such adjuvants for tablets, dragées and hard gelatin capsules.

Suitable adjuvants for soft gelatin capsules, are, for example, vegetable oils, waxes, fats, semi-solid substances and liquid polyols, etc.

Suitable adjuvants for the production of solutions and syrups are, for example, water, polyols, saccharose, invert sugar, glucose, etc.

Suitable adjuvants for injection solutions are, for example, water, alcohols, polyols, glycerol, vegetable oils, etc.

Suitable adjuvants for suppositories are, for example, natural or hardened oils, waxes, fats, semi-solid or liquid polyols, etc.

Moreover, the pharmaceutical preparations can contain preservatives, solubilizers, viscosity-increasing substances, stabilizers, wetting agents, emulsifiers, sweeteners, colorants, flavorants, salts for varying the osmotic pressure, buffers, masking agents or antioxidants. They can also contain still other therapeutically valuable substances.

The dosage can vary in wide limits and will, of course, be fitted to the individual requirements in each particular case. In general, in the case of oral administration a daily dosage of about 0.1 mg to 20 mg per kg body weight, preferably about 0.5 mg to 4 mg per kg body weight (e.g. about 300 mg per person), divided into preferably 1-3 individual doses, which can consist, for example, of the same amounts, should be appropriate. It will, however, be clear that the upper limit given herein can be exceeded when this is shown to be indicated.

In accordance with the invention, the compounds of formula (I) or their pharmaceutically acceptable salts and esters can be used for the treatment or prophylaxis of aldosterone mediated diseases.

The compounds of formula (I) or their pharmaceutically acceptable salts and esters herein are inhibitors of CYP11B2. The compounds of formula (I) or their pharmaceutically acceptable salts and esters herein display also variable inhibition of CYP11B1. These compounds may be used for the inhibition of CYP11B2 in combination with variable inhibition of CYP11B1. Such compounds may be used for treatment or prophylaxis of conditions displaying excessive cortisol production/levels or both excessive cortisol and aldosterone levels (for ex. Cushing syndrome, burn trauma patients, depression, post-traumatic stress disorders, chronic stress, corticotrophic adenomas, Morbus Cushing).

In accordance with the invention, the compounds of formula (I) or their pharmaceutically acceptable salts and esters can be used for the treatment or prophylaxis of cardiovascular conditions (including hypertension and heart failure), vascular conditions, endothelial dysfunction, baroreceptor dysfunction, renal conditions, liver conditions, fibrotic diseases, inflammatory conditions, retinopathy, neuropathy (such as peripheral neuropathy), pain, insulinopathy, edema, edematous conditions, depression and the like.

Cardiovascular conditions include congestive heart failure, coronary heart disease, arrhythmia, arterial fibrillation, cardiac lesions, decreased ejection fraction, diastolic and systolic heart dysfunction, fibrinoid necrosis of coronary arteries, cardiac fibrosis, hypertrophic cardiomyopathy, impaired arterial compliance, impaired diastolic filling, ischemia, left ventricular hypertrophy, myocardial and vascular fibrosis, myocardial infarction, myocardial necrotic lesions, cardiac arrhythmias, prevention of sudden cardiac death, restenosis, stroke, vascular damage.

Renal conditions include acute and chronic renal failure, nephropathy, end-stage renal disease, diabetic nephropathy, decreased creatinine clearance, decreased glomerular filtration rate, expansion of reticulated mesangial matrix with or without significant hypercellularity, focal thrombosis of glomerular capillaries, global fibrinoid necrosis, glomerulosclerosis, ischemic lesions, malignant nephrosclerosis (such as ischemic retraction, microalbuminuria, proteinuria, reduced renal blood flow, renal arteriopathy, swelling and proliferation of intracapillary (endothelial and mesangial) and/or extracapillary cells (crescents).

Renal conditions also include glomerulonephritis (such as diffuse proliferative, focal proliferative, mesangial proliferative, membranoproliferative, minimal change membranous glomerulonephritis), lupus nephritis, non-immune basement membrane abnormalities (such as Alport syndrome), renal fibrosis and glomerulosclerosis (such as nodular or global and focal segmental glomerulosclerosis).

Liver conditions include, but are not limited to, liver steatosis, nonalcoholic steatohepatitis, liver cirrhosis, liver ascites, hepatic congestion and the like.

Vascular conditions include, but are not limited to, thrombotic vascular disease (such as mural fibrinoid necrosis, extravasation and fragmentation of red blood cells, and luminal and/or mural thrombosis), proliferative arteriopathy (such as swollen myointimal cells surrounded by mucinous extracellular matrix and nodular thickening), atherosclerosis, decreased vascular compliance (such as stiffness, reduced ventricular compliance and reduced vascular compliance), endothelial dysfunction, and the like.

Inflammatory conditions include, but are not limited to, arthritis (for example, osteoarthritis), inflammatory airways diseases (for example, chronic obstructive pulmonary disease (COPD)), and the like.

Pain includes, but is not limited to, acute pain, chronic pain (for example, arthralgia), and the like.

Edema includes, but is not limited to, peripheral tissue edema, hepatic congestion, liver ascites, splenic congestion, respiratory or lung congestion, and the like.

Insulinopathies include, but are not limited to, insulin resistance, Type I diabetes mellitus, Type II diabetes mellitus, glucose sensitivity, pre-diabetic state, pre-diabetes, syndrome X, and the like.

Fibrotic diseases include, but are not limited to myocardial and intrarenal fibrosis, renal interstitial fibrosis and liver fibrosis.

Furthermore, the compounds of formula (I) or their pharmaceutically acceptable salts and esters as described herein can also be used for the treatment or prophylaxis of cardiovascular condition selected from the group consisting of hypertension, heart failure (particularly heart failure post myocardial infarction), left ventricular hypertrophy, and stroke.

In another embodiment, the cardiovascular condition is hypertension.

In particular embodiment, the cardiovascular condition is treatment-resistant hypertension.

In another embodiment, the cardiovascular condition is heart failure.

In another embodiment, the cardiovascular condition is left ventricular hypertrophy.

In another embodiment, the cardiovascular condition is congestive heart failure, more particularly in patients with preserved left ventricular ejection fraction.

In another embodiment, the cardiovascular condition is stroke.

In another embodiment, the compounds of formula (I) or their pharmaceutically acceptable salts and esters can be used for the treatment or prophylaxis renal condition.

In another embodiment, the renal condition is nephropathy.

In another embodiment, the renal condition is auto-immune glomerulonephritis.

In another embodiment, the chronic kidney disease is diabetic nephropathy.

In another embodiment, the fibrotic disease is kidney or heart fibrosis.

In another embodiment, the compounds of formula (I) or their pharmaceutically acceptable salts and esters can be used for the treatment or prophylaxis Type II diabetes mellitus.

In another embodiment, the compounds of formula (I) or their pharmaceutically acceptable salts and esters can be used for the treatment or prophylaxis Type I diabetes mellitus.

In another embodiment, the compounds of formula (I) or their pharmaceutically acceptable salts and esters can be used for the treatment or prophylaxis of diabetic retinopathy.

The invention is illustrated hereinafter by Examples, which have no limiting character.

In case the preparative examples are obtained as a mixture of enantiomers, the pure enantiomers can be separated by methods described herein or by methods known to the man skilled in the art, such as e.g. chiral chromatography or crystallization.

EXAMPLES

All examples and intermediates were prepared under argon atmosphere if not specified otherwise.

Intermediate A-1

1-Methyl-6-(4,4,5,5-tetramethyl-[1,3,2]dioxaborolan-2-yl)-3,4-dihydro-1H-quinolin-2-one

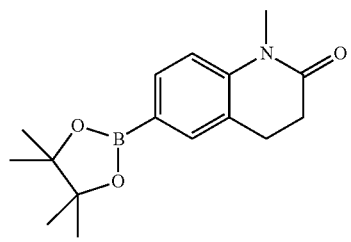 [SMILES: CN1C(=O)CCc2cc(B3OC(C)(C)C(C)(C)O3)ccc21]

[A]
6-Bromo-1-methyl-3,4-dihydro-1H-quinolin-2-one

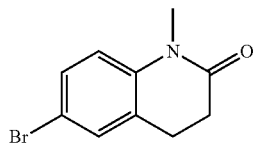

To a solution of 6-bromo-3,4-dihydroquinolin-2(1H)-one (5 g, 22.1 mmol) in DMF (100 mL) cooled to 0° C. was added potassium tert-butoxide (4.96 g, 44.2 mmol) portionwise and the reaction mixture was stirred at 0° C. for 15 min. Then, methyl iodide (4.08 g, 28.8 mmol) was added and the reaction mixture allowed to warm up to room temperature and stirring was continued over night. More MeI (1.25 g, 8.86 mmol) was added and the reaction mixture was heated to 40° C. until completion of the reaction. The mixture was diluted with EtOAc, poured into 100 mL of 1M HCl and the aqueous phase was extracted with EtOAc (2×200 mL). Combined organics were washed with brine, dried over $Na_2SO_4$, filtered and evaporated to dryness. The residue was purified by silica gel flash chromatography eluting with a 0 to 30% EtOAc-heptane gradient to give the title compound (4.23 g, 80%) as an off white solid. MS: 240.0, 242.1 ($M+H^+$).

[B] 1-Methyl-6-(4,4,5,5-tetramethyl-[1,3,2]dioxaborolan-2-yl)-3,4-dihydro-1H-quinolin-2-one

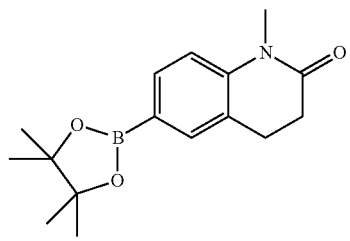 [SMILES: CN1C(=O)CCc2cc(B3OC(C)(C)C(C)(C)O3)ccc21]

A flask was charged with 6-bromo-1-methyl-3,4-dihydro-1H-quinolin-2-one (3 g, 12.5 mmol), 4,4,4',4',5,5,5',5'-octamethyl-2,2'-bi(1,3,2-dioxaborolane) (3.81 g, 15.0 mmol), potassium acetate (3.68 g, 37.5 mmol) and dioxane (48 mL). The mixture was purged with Ar, then dichloro[1,1'-bis(diphenylphosphino)-ferrocene]palladium(II) dichloromethane complex (1:1) [$PdCl_2$(DPPF)-$CH_2Cl_2$ adduct] (457 mg, 0.625 mmol) was added and the resulting mixture was heated to 80° C. over night. The reaction mixture was diluted with EtOAc, filtered through Dicalite and washed with EtOAc (2×150 mL). The resulting filtrate was washed with brine, dried over $Na_2SO_4$, filtered and evaporated to dryness. The residue was purified by silica gel flash chromatography eluting with a 0 to 40% EtOAc-heptane gradient to give the title compound (2.63 g, 73%) as an off white solid. MS: 288.0 ($M+H^+$).

Intermediate A-2

(rac)-6-(8-Amino-5,6,7,8-tetrahydroisoquinolin-4-yl)-1-methyl-3,4-dihydroquinolin-2(1H)-one

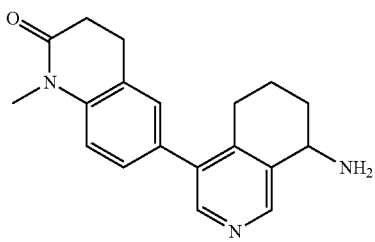 [SMILES: CN1C(=O)CCc2cc(-c3cncc4c3CCCC4N)ccc21]

[A] Ethyl 5-bromo-4-methylnicotinate

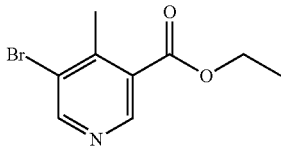

To a stirred light brown suspension of 5-bromo-4-methylnicotinic acid (10.00 g, 46.3 mmol) and ethanol (2.35 g, 2.97 mL, 50.9 mmol) in CH$_2$Cl$_2$ (231 mL) at 0° C. under Argon was added EDCI (10.9 g, 55.5 mmol) and DMAP (566 mg, 4.63 mmol), stirring was continued over night and the reaction mixture was allowed to warm up to RT. The reaction mixture was poured on aq. 10% KH$_2$PO$_4$ solution followed by extraction with AcOEt (3×). The organic phases were washed once with aq. 10% KH$_2$PO$_4$, aq. sat. NaHCO$_3$ and with aq. sat. NaCl solution. The combined organic phases were dried (Na$_2$SO$_4$), filtered and evaporated to afford the title compound (9.49 g, 84%) as brown solid. MS: 244.0 (M+H$^+$, 1Br).

[B] Methyl 4-bromo-8-oxo-5,6,7,8-tetrahydroisoquinoline-7-carboxylate

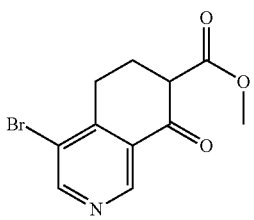

Ethyl 5-bromo-4-methylnicotinate (7.04 g, 28.8 mmol) in THF (28.8 mL) was added over a period of 20 min to a solution of LDA (31.7 mmol) [generated from N,N-diisopropylamine (4.52 mL, 31.7 mmol) and n-butyllithium (19.8 mL, 31.7 mmol, 1.6M in hexane) in THF (144 mL)] at −78° C. The resulting dark red solution was stirred for 20 min, then methyl acrylate (6.5 mL, 72.1 mmol) in THF (28.8 mL) was added over 15 min. The reaction was stirred an additional 1.5 h, then aq. 10% AcOH (57.8 mL, 101 mmol) was added (pH 4-5) and the reaction was allowed to warm to room temperature. After evaporation, the residue was partitioned between aq. sat. NaHCO$_3$ and EtOAc and extracted with EtOAc (3×). The combined organic layers were dried (Na$_2$SO$_4$) and concentrated to afford the title compound (7.80 g, 95% in 70% purity with 30% starting material) as brown solid. MS: 280.0 (M+H$^+$, 1Br).

[C] 4-Bromo-6,7-dihydroisoquinolin-8(5H)-one

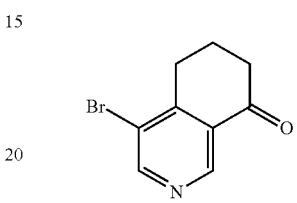

The crude methyl 4-bromo-8-oxo-5,6,7,8-tetrahydroisoquinoline-7-carboxylate (7.79 g, 27.4 mmol) was dissolved (small amount of not dissolved material) in aq. 6M HCl (84.1 mL, 505 mmol) and heated at reflux for 2.5 h (dark brown solution, no more SM visible on TLC). The acidic solution was concentrated in vacuo, suspended in water (ca. 25 mL), cooled in ice, and basified with 6.0 M KOH. The aqueous solution was washed with Et$_2$O (2×) and CH$_2$Cl$_2$ (3×), the combined organic layers were dried over Na$_2$SO$_4$, filtered and concentrated to afford after high vacuum drying the title compound (4.30 g, 69%) as brown solid. MS: 226.0 (M+H$^+$, 1Br).

[D] (rac)-4-Bromo-5,6,7,8-tetrahydroisoquinolin-8-amine

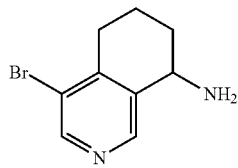 [SMILES: NC1CCCc2c(Br)cncc21]

4-Bromo-6,7-dihydroisoquinolin-8(5H)-one (4.81 g, 21.3 mmol), titanium (IV) isopropoxide (12.5 mL, 42.6 mmol) and ammonia, 2.0 M solution in MeOH (53.2 mL, 106 mmol) were stirred at RT for 5 h. The reaction was cooled to 0° C. and NaBH$_4$ (1.21 g, 31.9 mmol) was added portionwise over 10 min; the resulting mixture was stirred at RT for an additional 2 h. The reaction was quenched by pouring it into aq. ammonium hydroxide (25%), the precipitate was filtered and washed with EtOAc (3×, each time suspended in AcOEt and stirred for 5 min). The organic layer was separated and the remaining aqueous layer was extracted with EtOAc. The combined organic extracts were extracted with 1 M HCl. The acidic aqueous extracts were washed with ethyl acetate (1×), then treated with aqueous sodium hydroxide (2 M) to give pH 10-12, and extracted with EtOAc (3×). The combined organic extracts were washed with brine, dried (Na$_2$SO$_4$), and concentrated in vacuo to afford the title compound (4.11 g, 85%) as brown solid. MS: 225 (M+−H, 1Br).

[E] (rac)-6-(8-Amino-5,6,7,8-tetrahydroisoquinolin-4-yl)-1-methyl-3,4-dihydroquinolin-2(1H)-one

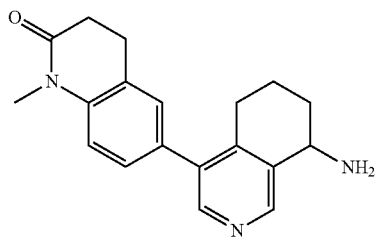 [SMILES: CN1C(=O)CCc2cc(-c3cncc4c3CCCC4N)ccc21]

In a 100 mL round-bottomed flask, (rac)-4-bromo-5,6,7,8-tetrahydroisoquinolin-8-amine (745 mg, 3.28 mmol) and 1-methyl-6-(4,4,5,5-tetramethyl-1,3,2-dioxaborolan-2-yl)-3,4-dihydroquinolin-2(1H)-one (intermediate A-1) (1.13 g, 3.94 mmol) were dissolved in ethanol (60 mL) to give a light brown solution. $Na_2CO_3$ (382 mg, 3.61 mmol), dissolved in water (10 mL) was added followed by tetrakis(triphenylphosphine)palladium (0) (114 mg, 98.4 µmol) after evacuation and replacing 5 times with Argon. The solution was then heated at 85° C. overnight. The reaction was treated with an aq. 10% NaCl solution and extracted with AcOEt (3×). The organic phases were washed again with an aq. 10% NaCl solution, dried over $Na_2SO_4$, filtered and evaporated under reduced pressure to give 1.39 g brown foam which was purified by flash chromatography (50 g $SiO_2$, Telos-cartridge, $CH_2Cl_2$/MeOH (3, 5, 7.5, 10 and 15%)) and precipitated from $CH_2Cl_2$ with n-pentane to give the title compound (690 mg, 68%) as a light brown foam. MS: 308.2 (M+H+).

Intermediate A-3

(rac)-N-(4-Bromo-6,7-dihydro-5H-cyclopenta[c]pyridin-7-yl)propionamide

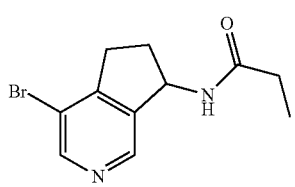

[A] Lithium 4-bromo-6-(methoxycarbonyl)-5H-cyclopenta[c]pyridin-7-olate

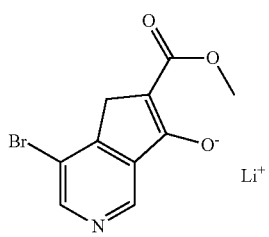

Ethyl 5-bromonicotinate (5 g, 21.7 mmol) in THF (22 mL) was added over a period of 20 min to a solution of LDA (23.9 mmol) [generated from N,N-diisopropylamine (3.41 mL, 23.9 mmol) and n-butyllithium (14.9 mL, 23.9 mmol, 1.6M in hexane) in THF (95 mL)] at −78° C. The resulting dark red solution was stirred for 30 min, then methyl acrylate (4.9 mL, 54.3 mmol) in THF (22 mL) was added over 15 min. The reaction was stirred an additional 1.5 h, then aq. 10% AcOH (43.5 mL, 76.1 mmol) was added (giving a pH of 4-5) and the reaction was allowed to warm to room temperature. Evaporation under reduced pressure afforded the title compound (in 50% purity, determined by $^1$H-NMR) as dark green amorphous solid. MS: 270.0 (M+H+, 1Br).

[B] 4-Bromo-5H-cyclopenta[c]pyridin-7(6H)-one

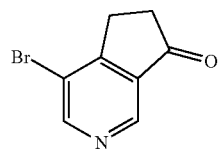 [SMILES: O=C1CCc2c(Br)cncc21]

The crude sodium 4-bromo-6-(methoxycarbonyl)-5H-cyclopenta[c]pyridin-7-olate (20.0 mmol) was dissolved in aq. 6 M HCl, (54 mL) and heated at reflux for 1.5 h.

The acidic solution was cooled in ice, poured into $Et_2O$, basified with aq. 6 M KOH (to give a pH of ~9) and extracted with $Et_2O$ (2×). The $Et_2O$ phases were collected, dried over $Na_2SO_4$, concentrated and purified by flash chromatography (20 g $SiO_2$, i-PrOH (1%)/$CH_2Cl_2$) to afford after trituration with a small amount of $Et_2O$ the title compound (0.69 g, 16% over 2 steps) as pink solid. MS: 212.0 (M+H+, 1Br).

[C] (rac)-4-Bromo-6,7-dihydro-5H-cyclopenta[c]pyridin-7-amine

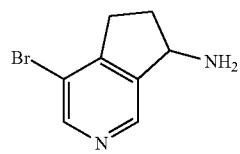 [SMILES: NC1CCc2c(Br)cncc21]

4-Bromo-5H-cyclopenta[c]pyridin-7(6H)-one (1.01 g, 4.76 mmol), titanium (IV) isopropoxide (2.79 mL, 9.53 mmol) and ammonia, 2M in MeOH (11.9 mL, 23.8 mmol) were stirred at RT for 5 h. The reaction mixture was cooled to 0° C. and $NaBH_4$ (270 mg, 7.14 mmol) was added in three portions over 20 min; the resulting mixture was stirred at RT for an additional 1.5 h. The reaction was quenched by pouring it into ammonium hydroxide (25%) (24.8 mL, pH 9-10), the precipitate was filtered and washed with AcOEt (3×, each time suspended in AcOEt and stirred for 5 min). The organic layer was separated and the remaining aqueous layer was extracted with EtOAc. The combined organic extracts were extracted with aq. 1 M HCl. The acidic aqueous extracts were washed with EtOAc (1×), then treated with aq. sodium hydroxide (2 M) to give a pH of 10-12, and extracted with EtOAc (3×). The combined organic extracts were washed with brine, dried (Na$_2$SO$_4$) and concentrated in vacuo to afford the title compound (530 mg, 52% yield in 70% purity, determined by $^1$H-NMR) as dark green amorphous solid. MS: 213.0 (M+H$^+$, 1Br).

[D] (rac)-N-(4-Bromo-6,7-dihydro-5H-cyclopenta[c]pyridin-7-yl)propionamide

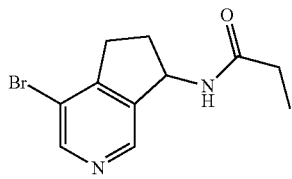

To a stirred black solution of (rac)-4-bromo-6,7-dihydro-5H-cyclopenta[c]pyridin-7-amine (213 mg, 1 mmol) and propionic acid (82.1 µL, 1.1 mmol) in CH$_2$Cl$_2$ (5.0 mL) at 0° C. was added EDCI (230 mg, 1.2 mmol), stirring was continued over night and the reaction mixture was allowed to warm up to RT. The reaction mixture was poured on aq. 10% KH$_2$PO$_4$ solution followed by extraction with AcOEt (3×). The organic phases were washed once with aq. 10% KH$_2$PO$_4$, sat. NaHCO$_3$ and with aq. sat. NaCl solution, the combined organic phases were dried over Na$_2$SO$_4$, filtered, evaporated and purified by flash chromatography (75 g SiO$_2$, Telos-cartridge, DCM/MeOH (2%)) to afford the title compound (105 mg, 39%) as a dark grey solid. MS: 269.0 (M+H$^+$, 1Br).

Intermediate A-4

(rac)-6-(7-Amino-6,7-dihydro-5H-cyclopenta[c]pyridin-4-yl)-1-methyl-3,4-dihydroquinolin-2(1H)-one

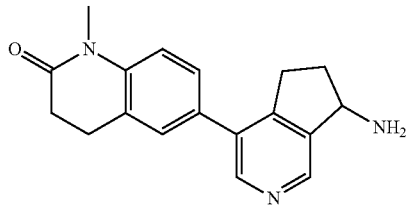 [SMILES: CN1C(=O)CCc2cc(-c3cncc4c3CCC4N)ccc21]

In a 50 ml round-bottomed flask, (rac)-4-bromo-6,7-dihydro-5H-cyclopenta[c]pyridin-7-amine (intermediate A-3[C]) (107 mg, 500 µmol) and 1-methyl-6-(4,4,5,5-tetramethyl-1,3,2-dioxaborolan-2-yl)-3,4-dihydroquinolin-2(1H)-one (intermediate A-1) (172 mg, 600 µmol) were dissolved in EtOH (9 mL) to give a brown solution. Na$_2$CO$_3$ (58.3 mg, 550 µmol), dissolved in water (1.5 mL) was added followed by tetrakis(triphenylphosphine)palladium (0) (17.3 mg, 15.0 mmol) after evacuation and replacing 5 times with Argon. The suspension was then heated at 85° C. overnight. A aq. 10% NaCl solution was added at RT, and the mixture was extracted with AcOEt (3×). The organic fractions were washed again with aq. 10% NaCl solution, dried over Na$_2$SO$_4$, filtered, evaporated and purified by flash chromatography (50 g SiO$_2$, Telos-cartridge, CH$_2$Cl$_2$/MeOH (2%)) to afford the title compound (21 mg, 14%) as a dark green powder. MS: 294.2 (M+H$^+$)

Intermediate A-5

1-Methyl-6-(1,2,3,4-tetrahydro-1,7-naphthyridin-5-yl)-3,4-dihydroquinolin-2(1H)-one

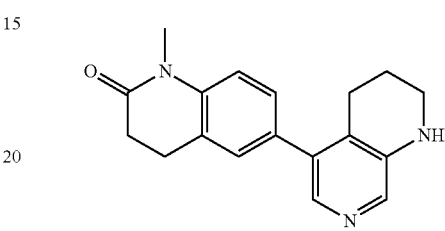

A microwave vial was charged with 5-bromo-1,2,3,4-tetrahydro-1,7-naphthyridine hydrochloride (0.1 g, 0.401 mmol), 1-methyl-6-(4,4,5,5-tetramethyl-[1,3,2]dioxaborolan-2-yl)-3,4-dihydro-1H-quinolin-2-one (intermediate A-1, 0.127 g, 0.441 mmol) and DMF (2.5 mL). The reaction mixture was purged with Argon. Then, bis(triphenylphosphine)palladium(II)chloride (0.028 g, 0.040 mmol), followed by a 1N aqueous Na$_2$CO$_3$ solution (1.6 mL, 1.6 mmol) were added and the reaction mixture was heated in the microwave at 120° C. for 30 min. The reaction mixture was diluted with EtOAc, filtered through Dicalite and washed with EtOAc (2×20 mL). The resulting filtrate was washed with brine, dried over Na$_2$SO$_4$, filtered and evaporated to dryness. The residue was purified by silica gel flash chromatography eluting with a 0 to 5% MeOH-DCM gradient to give the title compound (0.085 g, 72%) as a white solid. MS: 294.2 (M+H$^+$).

Intermediate A-6

(rac)-N-(4-Bromo-6,7-dihydro-5H-cyclopenta[c]pyridin-7-yl)ethanesulfonamide

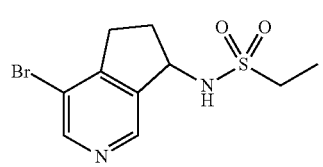 [SMILES: CCS(=O)(=O)NC1CCc2c(Br)cncc21]

In analogy to the procedure described for the preparation of example 4, (rac)-4-bromo-6,7-dihydro-5H-cyclopenta[c]pyridin-7-amine (intermediate A-3 [C]) and ethanesulfonyl chloride gave the title compound as a grey solid in 94% yield. MS: 304.99 (M+H$^+$, 1Br).

Intermediate A-7

8-Fluoro-1-methyl-6-(4,4,5,5-tetramethyl-[1,3,2]dioxaborolan-2-yl)-3,4-dihydro-1H-quinolin-2-one

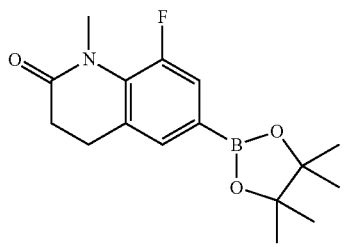 [SMILES: CN1C(=O)CCc2cc(B3OC(C)(C)C(C)(C)O3)cc(F)c21]

[A] 3-Chloro-N-(2-fluoro-phenyl)-propionamide

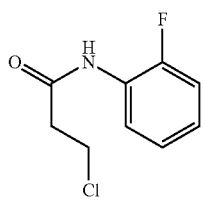 [SMILES: O=C(CCCl)Nc1ccccc1F]

To a solution of 2-fluoroaniline (6.67 g, 60 mmol) and pyridine (5.21 g, 66 mmol) in 1,2-dichloroethane (50 mL) was added 3-chloropropionyl chloride (8.38 g, 66 mmol) dropwise at 15° C. After stirring at room temperature for 2 hr, the mixture was washed with water and then 2N aq. hydrochloric acid. The organic layer was dried over anhy. Na$_2$SO$_4$, filtered, and concentrated in vacuo to afford title compound (10.9 g, 90% yield) as an oil. MS: 202.1 (M+H)$^+$.

[B] 8-Fluoro-3,4-dihydro-1H-quinolin-2-one

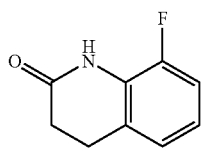 [SMILES: O=C1CCc2cccc(F)c2N1]

A flame-dried 50-mL flask equipped with a magnetic stirring bar was charged with 3-chloro-N-(2-fluoro-phenyl)-propionamide (5.33 g, 26.5 mmol) and aluminium chloride (5.30 g, 39.7 mmol). In a pre-heated oil bath, the flask was heated at 160° C. for 1.5 hr. After cooling to room temperature, the mixture was treated with ice-water slowly and extracted with EtOAc. The organic layer was washed with water and brine in sequence, dried over anhy. Na$_2$SO$_4$, filtered, and concentrated in vacuo. The resulting residue was then purified by flash chromatography (silica gel, 30% ethyl acetate in hexane) to afford title compound (3.1 g, 70% yield) as a solid. MS: 166.0 (M+H)$^+$.

[C] 6-Bromo-8-fluoro-3,4-dihydro-1H-quinolin-2-one

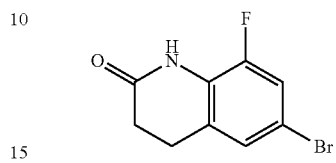

NBS (0.62 g, 3.5 mmol) dissolved in DMF (5 mL) was added to a solution of 8-fluoro-3,4-dihydro-1H-quinolin-2-one (0.52 g, 3.2 mmol) in DMF (5 mL) dropwise at 0° C. The resulting reaction mixture was stirred at room temperature for 12 hr before it was treated with water. The precipitated solid was collected through filtration, washed with ether, and dried over vacuum to afford title compound (0.65 g, 85% yield) as a white solid. MS: 244.1 (M+H)$^+$.

[D] 6-Bromo-8-fluoro-1-methyl-3,4-dihydro-1H-quinolin-2-one

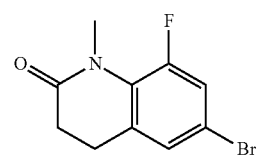

A solution of 6-bromo-8-fluoro-3,4-dihydro-1H-quinolin-2-one (0.21 g, 0.86 mmol) in DMF (2 mL) was treated with potassium tert-butoxide (0.19 g, 1.72 mmol) at 0° C. The resulting mixture was stirred at 0° C. for 30 min before methyl iodide (0.18 g, 1.29 mmol) was added. After stirring for 2 h, the reaction mixture was treated with water, extracted with EtOAc, washed with water and brine in sequence, and dried over anhy. Na$_2$SO$_4$. After removal of the solvents under reduced pressure, the crude product (0.18 g, 80% yield) was obtained as a white solid. MS: 258.0 (M+H)$^+$.

[E] 8-Fluoro-1-methyl-6-(4,4,5,5-tetramethyl-[1,3,2]dioxaborolan-2-yl)-3,4-dihydro-1H-quinolin-2-one

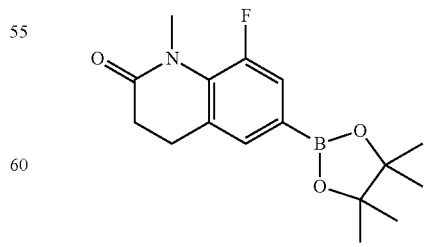

A mixture of 6-bromo-8-fluoro-1-methyl-3,4-dihydro-1H-quinolin-2-one (0.18 g, 0.36 mmol), bis(pinacolato)diboron (0.25 g, 1.05 mmol), 1,1'-bis(diphenylphosphino)ferrocene-dichloropalladium (II) (28.6 mg, 0.035 mmol), and potassium acetate (0.21 g, 2.1 mmol) in dioxane (3 mL) was heated in a microwave at 100° C. for 3 hr. After dilution with EtOAc, the organic layer was washed with water, dried over anhy. $Na_2SO_4$ and concentrated in vacuo. The residue was then purified by flash chromatography (silica gel, 30% ethyl acetate in hexane) to afford the title product (0.15 g, 70% yield) as a white solid. MS: 306.2 $(M+H)^+$.

Intermediate A-8

8-Chloro-1-methyl-6-(4,4,5,5-tetramethyl-[1,3,2]dioxaborolan-2-yl)-3,4-dihydro-1H-quinolin-2-one

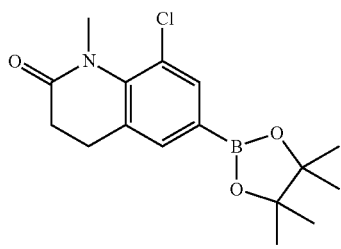 [SMILES: CN1C(=O)CCc2cc(B3OC(C)(C)C(C)(C)O3)cc(Cl)c21]

[A]
N-(4-Bromo-2-chloro-phenyl)-3-chloro-propionamide

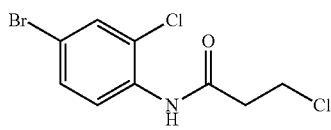 [SMILES: O=C(CCCl)Nc1ccc(Br)cc1Cl]

To a solution of 4-bromo-2-chloro-phenylamine (32 g, 0.15 mol) and pyridine (13.45 g, 0.17 mol) in DCM (200 mL) was added 3-chloropropionyl chloride (21.65 g, 0.17 mol) dropwise at 15° C. After stirring at room temperature for 1 hr, the mixture was washed with water and then 2 N aq. hydrochloric acid. The organic layer was dried over anhy. $Na_2SO_4$, filtered, and concentrated in vacuo to afford the title compound (10.9 g, 90% yield) as a white solid.

[B]
6-Bromo-8-chloro-3,4-dihydro-1H-quinolin-2-one

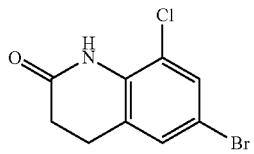

A flame-dried 500-mL flask equipped with a magnetic stirring bar was charged with N-(4-bromo-2-chloro-phenyl)-3-chloro-propionamide (29.7 g, 0.1 mol) and aluminium chloride (53.3 g, 0.4 mol). In a pre-heated oil bath, the flask was heated at 140° C. for 1 hr. After cooling to room temperature, the mixture was treated with ice-water slowly and extracted with EtOAc. The organic layer was washed with water and brine in sequence, dried over anhy. $Na_2SO_4$, filtered, and concentrated in vacuo. The resulting residue was then purified by flash chromatography (silica gel, 30% ethyl acetate in hexane) to afford the title compound (7.0 g, 27% yield) as a white solid.

[C] 6-Bromo-8-chloro-1-methyl-3,4-dihydro-1H-quinolin-2-one

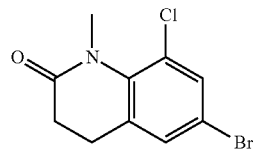

A solution of 6-bromo-8-chloro-3,4-dihydro-1H-quinolin-2-one (7.0 g, 26.9 mmol) in DMF (100 mL) was treated with potassium tert-butoxide (6.0 g, 53.8 mmol) at 0° C. in portions. The resulting mixture was stirred at 0° C. for 30 min before methyl iodide (5.0 g, 35.0 mmol) was added. After stirring for 12 h, the reaction mixture was treated with water, extracted with EtOAc, washed with water and brine in sequence, and dried over anhy. $Na_2SO_4$. After removal of solvents under reduced pressure, the crude product (3.3 g, 45% yield) was obtained as a white solid.

[D] 8-Chloro-1-methyl-6-(4,4,5,5-tetramethyl-[1,3,2]dioxaborolan-2-yl)-3,4-dihydro-1H-quinolin-2-one

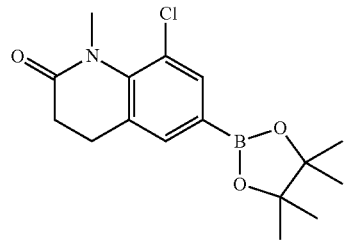 [SMILES: CN1C(=O)CCc2cc(B3OC(C)(C)C(C)(C)O3)cc(Cl)c21]

A mixture of 6-bromo-8-chloro-1-methyl-3,4-dihydro-1H-quinolin-2-one (0.23 g, 0.84 mmol), bis(pinacolato)diboron (0.255 g, 1.01 mmol), 1,1'-bis(diphenylphosphino)-ferrocene-dichloropalladium (II) (30.7 mg, 0.04 mmol), and potassium acetate (0.247 g, 2.52 mmol) in dioxane (5 mL) was heated in a microwave at 80° C. over night. After dilution with EtOAc, the organic layer was washed with water, dried over anhy. $Na_2SO_4$ and concentrated in vacuo. The residue was then purified by flash chromatography (silica gel, 30% ethyl acetate in hexane) to afford the title product (0.17 g, 63% yield) as a white solid.

Intermediate A-9

7-Fluoro-1-methyl-6-(4,4,5,5-tetramethyl-[1,3,2]dioxaborolan-2-yl)-3,4-dihydro-1H-quinolin-2-one

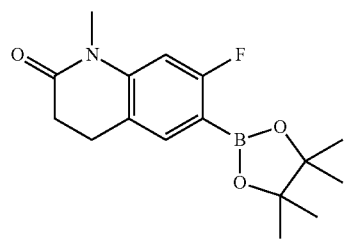 [SMILES: CN1C(=O)CCc2cc(B3OC(C)(C)C(C)(C)O3)c(F)cc21]

[A] 3-Chloro-N-(3-fluoro-phenyl)-propionamide

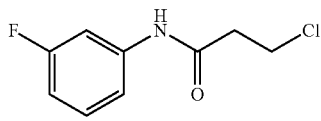 [SMILES: O=C(CCCl)Nc1cccc(F)c1]

To a solution of 3-fluoroaniline (10 mL, 104.02 mmol) in DCM (100 mL) was added pyridine (21 mL, 260.2 mmol) and 3-chloropropionyl chloride (12 mL, 124.4 mmol). The reaction mixture was stirred for 3 hr at room temperature until the starting material had disappeared as shown by LC-MS analysis. The reaction mixture was then diluted with $H_2O$ and extracted with EtOAc. The organic layer was dried over anhy. $Na_2SO_4$ and concentrated in vacuo to afford the title compound as a solid. It was used in the next step without further purification.

[B] 7-Fluoro-3,4-dihydro-1H-quinolin-2-one

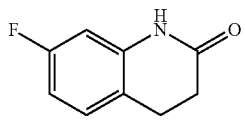

A flame-dried 50-mL flask equipped with a magnetic stirring bar was charged with 3-chloro-N-(3-fluoro-phenyl)-propionamide (10 g, 49.6 mmol) and $AlCl_3$ (23.1 g, 173.6 mmol). On a pre-heated oil bath, the flask was heated at 120~125° C. for 2 hr until a LC-MS analysis indicated the reaction was complete. After cooling to room temperature, the mixture was treated with ice-water slowly. After extraction with EtOAc, the combined organic layers were washed with water and brine in sequence. The organic layer was dried over anhy. $Na_2SO_4$, filtered, and concentrated in vacuo to afford a white solid (7.63 g) as a crude mixture of two regioisomeric products (7-fluoro-3,4-dihydro-1H-quinolin-2-one and 5-fluoro-3,4-dihydro-1H-quinolin-2-one) in a ratio of 5.3:1. This mixture was then refluxed in EtOAc (70 mL) for 30 min before it was cooled to room temperature and concentrated to ~35 mL. The precipitated solid (5.83 g) was collected by vacuum filtration affording the desired 7-fluoro-3,4-dihydro-1H-quinolin-2-one enriched to 95.8%. After repeating three more times the above recrystallization procedure, 4.12 g of the title compound was obtained as a white solid in >99.5% purity.

[C] 7-Fluoro-1-methyl-3,4-dihydro-1H-quinolin-2-one

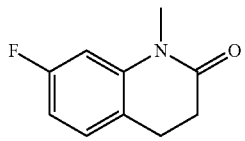

To an ice cold solution of 7-fluoro-3,4-dihydro-1H-quinolin-2-one (16.5 g, 0.1 mol) in DMF (200 mL) was added potassium tert-butoxide (22.4 g, 0.2 mol) in 2 portions. The reaction mixture was stirred at 0° C. for 30 min before MeI (25.4 g, 0.18 mol) was added. After the addition, the reaction mixture was allowed to warm up to room temperature slowly and stirred at room temperature over night. The reaction mixture was diluted with EtOAc (500 mL), then poured into 200 mL of 1 N aq. HCl. After extraction with EtOAc (200 mL, 3×), the combined organic layers were washed with brine, dried over anhy. $Na_2SO_4$, filtered and concentrated in vacuo to give crude title compounds as oil (16.0 g, 89% yield). It was used in the next step without further purification.

[D] 6-Bromo-7-fluoro-1-methyl-3,4-dihydro-1H-quinolin-2-one

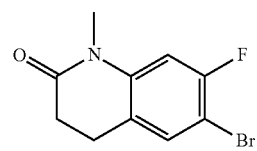

To an ice cold solution of 7-fluoro-1-methyl-3,4-dihydro-1H-quinolin-2-one (16.0 g, 89.4 mmol) in DMF (200 mL) was added NBS (16.0 g, 89.4 mmol). After the addition, the reaction mixture was warmed up to room temperature and stirred for 3 hr. After LC-MS analysis indicated the completion of reaction, the mixture was diluted with EtOAc (500 mL) and poured into water (500 mL). The aqueous layer was then extracted with EtOAc (200 mL, 3×) and the combined organic layers were washed with brine, dried over anhy. $Na_2SO_4$, filtered and concentrated in vacuo to give crude title compound as oil (18.0 g, 78% yield). It was used in the next step without further purification.

[E] 7-Fluoro-1-methyl-6-(4,4,5,5-tetramethyl-[1,3,2]dioxaborolan-2-yl)-3,4-dihydro-1H-quinolin-2-one

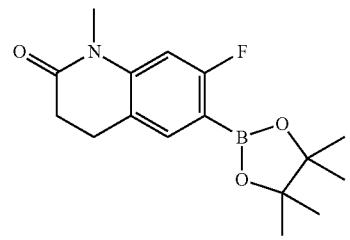 [SMILES: CN1C(=O)CCc2cc(B3OC(C)(C)C(C)(C)O3)c(F)cc21]

To a mixture of 6-bromo-7-fluoro-1-methyl-3,4-dihydro-1H-quinolin-2-one (18.0 g, 69.8 mmol) in dry dioxane (400 mL) was added 4,4,4',4',5,5,5',5'-octamethyl-2,2'-bi(1,3,2-dioxaborolane) (20.0 g, 83.8 mmol), potassium acetate (20.5 g, 209.4 mmol) and dichloro[1,1'-bis(diphenylphosphino)-ferrocene]palladium(II) dichloromethane complex (1:1) [$PdCl_2$(DPPF)-$CH_2Cl_2$ adduct] (2.55 g, 3.49 mmol). Under argon protection, the reaction mixture was heated at 85° C. over night. After dilution with EtOAc, the mixture was filtrated through a Celite pad and the filter cake was washed with additional EtOAc several times. The combined filtrate was then washed with brine, dried over anhy. $Na_2SO_4$, filtered and concentrated in vacuo. Silica gel column chromatography separation (0 to 30% EtOAc in hexane) afforded the crude title compound as white sticky material. Trituration with hexane several times gave the crude product as a white solid (10.0 g, 47% yield).

Intermediate A-10

7-Chloro-1-methyl-6-(4,4,5,5-tetramethyl-[1,3,2]dioxaborolan-2-yl)-3,4-dihydro-1H-quinolin-2-one

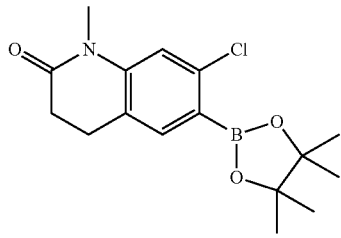 [SMILES: CN1C(=O)CCc2cc(B3OC(C)(C)C(C)(C)O3)c(Cl)cc21]

[A]
N-(4-Bromo-3-chloro-phenyl)-3-chloro-propionamide

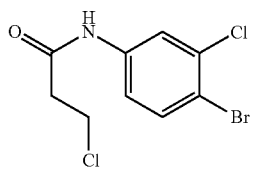 [SMILES: O=C(CCCl)Nc1ccc(Br)c(Cl)c1]

To a solution of 4-bromo-3-chloroaniline (6.0 g, 29.1 mmol) and pyridine (3.45 g, 43.6 mmol) in 1,2-dichloroethane (50 mL) was added 3-chloropropionyl chloride (5.53 g, 43.6 mmol) drop wise at 15° C. After stirring for 2 hr at room temperature, the mixture was washed with water and then 2 N aq. hydrochloric acid. The organic layer was dried over anhy. Na$_2$SO$_4$, and after filtration, the solvent was removed under reduced pressure. The product N-(4-bromo-3-chloro-phenyl)-3-chloro-propionamide (8.20 g, 95% yield) was obtained as oil. MS: 298.0 (M+H)$^+$.

[B]
6-Bromo-7-chloro-3,4-dihydro-1H-quinolin-2-one

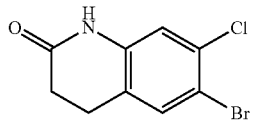

A flame-dried 50-mL flask equipped with a magnetic stirring bar was charged with N-(4-bromo-3-chloro-phenyl)-3-chloro-propionamide (1.0 g, 3.36 mmol) and aluminium chloride (0.67 g, 5.04 mmol). In a pre-heated oil bath, the flask was heated at 135~140° C. for 2 hr. After cooling to room temperature, the reaction mixture was treated with ice-water slowly, and extracted with EtOAc. The organic layer was washed with water and brine in sequence, dried over anhy. Na$_2$SO$_4$. After evaporation of the solvent, the residue was purified by recrystallization in EtOAc (2 mL) and gave title compound (0.44 g, 50% yield) as a solid. MS: 260.0 (M+H)$^+$.

[C] 6-Bromo-7-chloro-1-methyl-3,4-dihydro-1H-quinolin-2-one

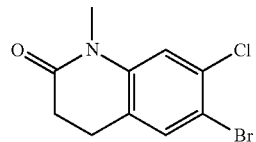

Potassium tert-butoxide (0.45 g, 4.0 mmol) was added at 0° C. to a solution of 6-bromo-7-chloro-3,4-dihydro-1H-quinolin-2-one (0.52 g, 2.0 mmol) in DMF (5 mL). Then, the reaction mixture was stirred at 0° C. for 30 min and methyl iodide (0.18 g, 1.29 mmol) was added. The resulting mixture was then stirred for 2 h before water was added. After extraction of the reaction mixture with EtOAc, the organic layer was washed with water and brine in sequence. Then, the organic layer was dried over anhy. Na$_2$SO$_4$ and the solvent was removed under reduced pressure to give a crude product (0.49 g, 90% yield) as a white solid. MS: 274.0 (M+H)$^+$.

[D] 7-Chloro-1-methyl-6-(4,4,5,5-tetramethyl-[1,3,2]dioxaborolan-2-yl)-3,4-dihydro-1H-quinolin-2-one

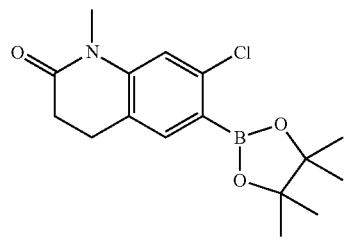

A mixture of 6-bromo-7-chloro-1-methyl-3,4-dihydro-1H-quinolin-2-one (0.1 g, 0.36 mmol), bis(pinacolato)diboron (0.13 g, 0.55 mmol), 1,1'-bis(diphenylphosphino) ferrocenedichloro-palladium (II) (14.7 mg, 0.018 mmol), and potassium acetate (0.11 g, 1.08 mmol) in dioxane (3 mL) was heated in a microwave at 100° C. for 3 hr. The mixture was then diluted with EtOAc, washed with water, dried over anhy. Na$_2$SO$_4$, and concentrated in vacuo. The residue was purified by flash chromatography (silica gel, 30% ethyl acetate in hexane) to afford the title product (82 mg, 70% yield) as a white solid. MS: 322.1 (M+H)$^+$.

Intermediate B-1

(rac)-N-(4-Bromo-5,6,7,8-tetrahydro-isoquinolin-8-yl)-propionamide

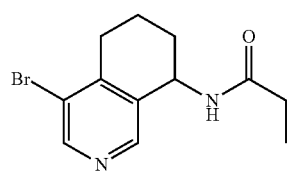 [SMILES: CCC(=O)NC1CCCc2c(Br)cncc21]

To a solution of (rac)-4-bromo-5,6,7,8-tetrahydro-isoquinolin-8-ylamine (intermediate A-2 [D]) (3.7 g, 16.3 mmol) and Et$_3$N (3.3 g, 32.6 mmol) in DCM (50 mL) was added propionyl chloride (2.25 g, 24.4 mmol) at 0° C. The resulting reaction mixture was stirred for 3 hr before it was warmed up to room temperature and poured into water (50 mL) and extracted with DCM (2×50 mL). The combined organic layers were then dried over anhy. Na$_2$SO$_4$, filtered, and concentrated in vacuo. The residue was purified by silica gel column chromatography and afforded the title compound (4.29 g, 93% yield) as a white solid. MS: 283.0 (M+H$^+$).

Intermediate B-2a and B-2b (+)-N—((R or S)-4-Bromo-5,6,7,8-tetrahydro-isoquinolin-8-yl)-propionamide and (−)-N—((S or R)-4-Bromo-5,6,7,8-tetrahydro-isoquinolin-8-yl)-propionamide Intermediate B-2a

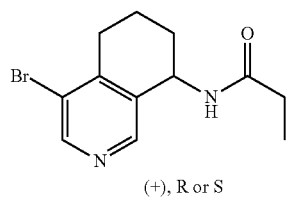

(+), R or S

Intermediate B-2b

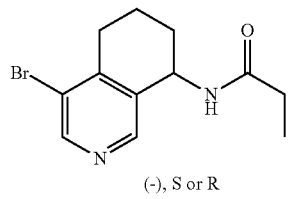

(−), S or R

The racemic mixture of (rac)-N-(4-bromo-5,6,7,8-tetrahydro-isoquinolin-8-yl)-propionamide (intermediate B-1) was subjected to SFC separation (column: IC 250 mm×50 mm, 5 μm; mobile phase: A) supercritical CO$_2$, B) IPA (0.05% NH$_3$ aq.), A:B=60:40, at 140 mL/min) and afforded the two enantiomeric title compounds, (+)-N—((R or S)-4-bromo-5,6,7,8-tetrahydro-isoquinolin-8-yl)-propionamide, intermediate B-2a, $[\alpha]^D_{(20\ deg)}$=+93.33°, (0.33% in MeOH) (1.02 g) and (−)-N—((S or R)-4-bromo-5,6,7,8-tetrahydro-isoquinolin-8-yl)-propionamide, intermediate B-2b, $[\alpha]^D_{(20\ deg)}$=−87.27°, (0.33% in MeOH) (1.07 g), respectively. MS: 283.0 (M+H$^+$).

Intermediate B-3a and B-3b (−)-(S)-4-Bromo-5,6,7,8-tetrahydroisoquinolin-8-amine and (+)-(R)-4-Bromo-5,6,7,8-tetrahydroisoquinolin-8-amine Intermediate B-3a

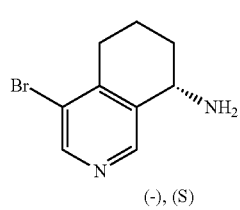

(−), (S)

Intermediate B-3b

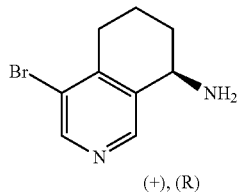

(+), (R)

The title compounds were prepared by chiral separation of (rac)-4-bromo-5,6,7,8-tetrahydroisoquinolin-8-amine (intermediate A-2 [D]) on a Chiralpak AD column (40% 2-propanol in n-heptane) to give after precipitation from CH$_2$Cl$_2$ with n-pentane 37% of (−)-(S)-4-bromo-5,6,7,8-tetrahydroisoquinolin-8-amine (intermediate B-3a) as light brown crystals; MS: 227.0 (M+H$^+$, 1Br), $[\alpha]^D_{(20\ deg)}$=−8.72, (c=0.41 in MeOH). and 36% of (+)-(R)-4-bromo-5,6,7,8-tetrahydroisoquinolin-8-amine (intermediate B-3b) as light brown crystals. MS: 227.0 (M+H$^+$, 1Br), $[\alpha]^D_{(20\ deg)}$=+7.998, (c=1.0 in MeOH).

Crystallization of (−)-(S)-4-bromo-5,6,7,8-tetrahydroisoquinolin-8-amine (intermediate B-3a) from n-pentane gave single crystals; X-ray crystallographic analysis allowed to assign the absolute configuration (S).

Intermediate B-4

(rac)-Ethanesulfonic acid (4-bromo-5,6,7,8-tetrahydro-isoquinolin-8-yl)-amide

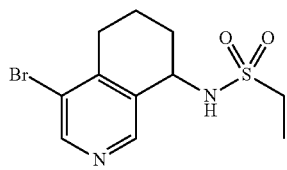 [SMILES: CCS(=O)(=O)NC1CCCc2c(Br)cncc21]

To a solution of (rac)-4-bromo-5,6,7,8-tetrahydro-isoquinolin-8-ylamine (intermediate A-2 [D]) (227 mg, 1 mmol) and Et$_3$N (152 mg, 1.5 mmol) in DCM (5 mL) was added ethanesulfonyl chloride (193 mg, 1.5 mmol) at 0° C. The reaction mixture was stirred at room temperature for 1 hr before it was concentrated in vacuo. The residue was dissolved in ethyl acetate and washed with water and the organic layer was dried over anhy. Na$_2$SO$_4$, filtered, and concentrated in vacuo to give a crude product (302 mg, 95% yield). MS: 319.0 (M+H)$^+$.

Intermediate B-5

(all rac)-N-(4-Bromo-7-methyl-5,6,7,8-tetrahydro-isoquinolin-8-yl)-propionamide

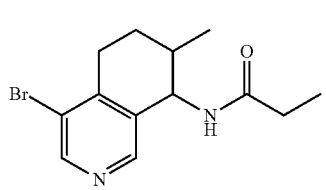 [SMILES: CCC(=O)NC1c2cncc(Br)c2CCC1C]

[A] (rac)-4-Bromo-7-methyl-8-oxo-5,6,7,8-tetrahydro-isoquinoline-7-carboxylic acid methyl ester

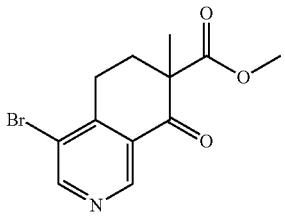 [SMILES: COC(=O)C1(C)CCc2c(Br)cncc2C1=O]

To a stirred solution of (rac)-methyl 4-bromo-8-oxo-5,6,7,8-tetrahydroisoquinoline-7-carboxylate (3.5 g, 12.3 mmol) (intermediate A-2 [B]) in DMF (10 mL) and THF (50 mL) was added 60% NaH (750 mg, 18.5 mmol) in portions at 0° C. The reaction mixture was stirred at 0° C. for 15 min before methyl iodide (1.6 mL, 24.6 mmol) was added and the resulting reaction mixture was allowed to warm up to room temperature and stirred over night. The reaction mixture was then diluted with water (10 mL) and extracted with EtOAc (2×100 mL). Combined organics were washed with brine, dried over Na$_2$SO$_4$, filtered and evaporated to dryness. The residue was purified by silica gel flash chromatography eluting with a 0 to 30% EtOAc-heptane gradient to give the title compound (3.3 g, 90% yield) as a light yellow solid. MS: 297.9 & 299.9 (M+H)$^+$.

[B] (rac)-4-Bromo-7-methyl-6,7-dihydro-5H-isoquinolin-8-one

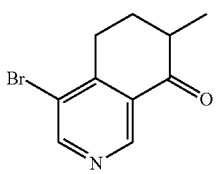

(rac)-4-Bromo-7-methyl-8-oxo-5,6,7,8-tetrahydro-isoquinoline-7-carboxylic acid methyl ester (3.3 g, 11.0 mmol) was dissolved in aq. 6 N HCl (28.0 mL, 168 mmol) and heated at reflux for 2.5 h. The acidic solution was concentrated in vacuo, re-suspended in water (ca. 25 mL), cooled in an ice-water bath, and basified with 6 N aq. KOH solution. The aqueous solution was then washed with Et$_2$O (2×) and DCM (3×). The combined organic layers were dried over anhy. Na$_2$SO$_4$, filtered and concentrated in vacuo to afford the title compound (2.38 g, 90% yield) as a brown solid. MS: 240.1 & 242.1 (M+H)$^+$.

[C] (all rac)-4-Bromo-7-methyl-5,6,7,8-tetrahydro-isoquinolin-8-ylamine

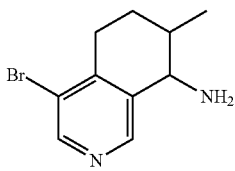

A mixture of (rac)-4-bromo-7-methyl-6,7-dihydro-5H-isoquinolin-8-one (2.2 g, 9.2 mmol), NaBH$_3$CN (864 mg, 13.8 mmol) and CH$_3$COONH$_4$ (7.1 g, 92 mmol) in isopropanol (20 mL) was refluxed for 3 hr. Afterwards, the solution was cooled to room temperature; it was then concentrated in vacuo to afford a yellow oil, which was extracted with EtOAc (2×100 mL). Combined organics were washed with brine, dried over anhy. Na$_2$SO$_4$, filtered and concentrated in vacuo to afford the title compound (1.77 g, 80% yield) as a brown solid. MS: 241.1 & 243.1 (M+H)$^+$.

[D] (all rac)-N-(4-Bromo-7-methyl-5,6,7,8-tetrahydro-isoquinolin-8-yl)-propionamide

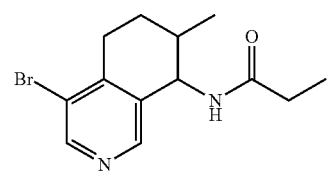 [SMILES: CCC(=O)NC1c2cncc(Br)c2CCC1C]

To a stirred solution of (all rac)-4-bromo-7-methyl-5,6,7,8-tetrahydro-isoquinolin-8-ylamine (1.7 g, 7.1 mmol) and Et$_3$N (1.0 mL) in DCM (20 mL) was added propionyl chloride (0.74 mL, 8.52 mmol) at 0° C. and the mixture was stirred for 1 h. It was then extracted with EtOAc (2×100 mL) and combined organics were washed with brine, dried over anhy. Na$_2$SO$_4$, filtered and concentrated in vacuo. The residue was then purified by silica gel flash chromatography eluting with a 0 to 30% EtOAc-heptane gradient to give the title compound (1.2 g, 57% yield) as a light yellow solid. MS: 297.1 & 299.1 (M+H)$^+$.

Intermediate B-6a (−)-N-((7R,8S or 7S,8R)-4-Bromo-7-methyl-5,6,7,8-tetrahydro-isoquinolin-8-yl)-propionamide Intermediate B-6a

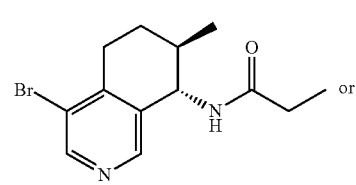

or

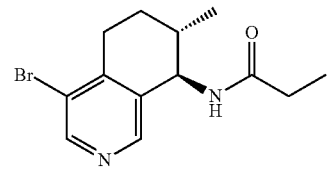

Intermediate B-6b (−)-N-((7S,8S or 7R,8R)-4-Bromo-7-methyl-5,6,7,8-tetrahydro-isoquinolin-8-yl)-propionamide

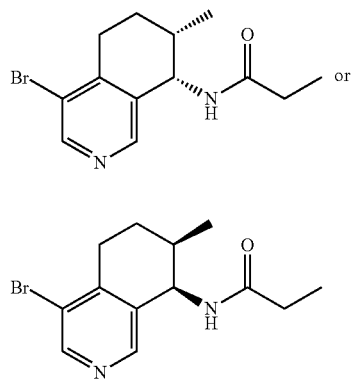

Intermediate B-6b

Intermediate B-6c (+)-N-((7S,8R or 7R,8S)-4-Bromo-7-methyl-5,6,7,8-tetrahydro-isoquinolin-8-yl)-propionamide

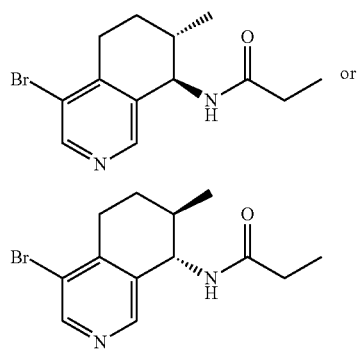

Intermediate B-6c

Intermediate B-6d (+)-N-((7R,8R or 7S,8S)-4-Bromo-7-methyl-5,6,7,8-tetrahydro-isoquinolin-8-yl)-propionamide

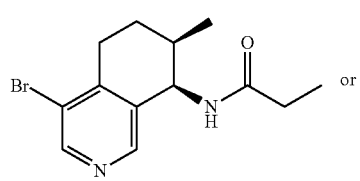

Intermediate B-6d

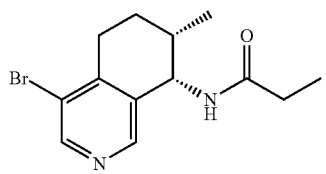

The title intermediates were prepared by chiral separation of (all rac)-N-(4-bromo-7-methyl-5,6,7,8-tetrahydro-isoquinolin-8-yl)-propionamide (intermediate B-5, 1.2 g) on a Chiralpak AD column (40% ethanol in n-hexane) to give (−)-N-((7R,8S or 7S,8R)-4-bromo-7-methyl-5,6,7,8-tetrahydro-isoquinolin-8-yl)-propionamide (intermediate B-6a) as light yellow oil, MS: 297.1 & 299.1 (M+H$^+$) and (−)-N-((7S, 8S or 7R,8R)-4-bromo-7-methyl-5,6,7,8-tetrahydro-isoquinolin-8-yl)-propionamide (intermediate B-6b) as off-white solid, MS: 297.1 & 299.1 (M+H$^+$) and (+)-N-((7S,8R or 7R,8S)-4-bromo-7-methyl-5,6,7,8-tetrahydro-isoquinolin-8-yl)-propionamide (intermediate B-6c) as light yellow oil, MS: 297.1 & 299.1 (M+H$^+$) and (+)-N-((7R,8R or 7S,8S)-4-bromo-7-methyl-5,6,7,8-tetrahydro-isoquinolin-8-yl)-propionamide (intermediate B-6d) as off-white solid, MS: 297.1 & 299.1 (M+H)$^+$.

Intermediate B-7

(all rac)-N-(4-Bromo-7-fluoro-5,6,7,8-tetrahydro-isoquinolin-8-yl)-propionamide

[A][4-Bromo-6,7-dihydro-5H-isoquinolin-(8E)-ylidene]-butyl-amine

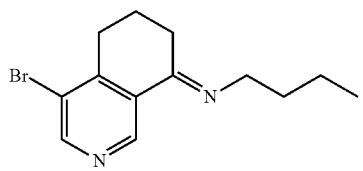 [SMILES: CCCC/N=C1\CCCc2c(Br)cncc21]

A solution of 4-bromo-6,7-dihydro-5H-isoquinolin-8-one (2.2 g, 9.7 mmol) (intermediate A-2 [C]), butylamine (1.02 g, 13.8 mmol) and PPTS (200 mg, 1.05 mmol) in ethanol (90 mL) was refluxed for 3 hr before it was cooled to room temperature and concentrated in vacuo to afford a yellow oil, which was extracted with EtOAc (2×100 mL). The combined organics were washed with brine, dried over anhy. Na$_2$SO$_4$, filtered and concentrated in vacuo to afford the title compound (2.45 g, 90% yield) as a brown solid, MS: 281.1 & 283.1 (M+H)⁺.

[B] [4-Bromo-7-fluoro-6,7-dihydro-5H-isoquinolin-(8Z)-ylidene]-butyl-amine

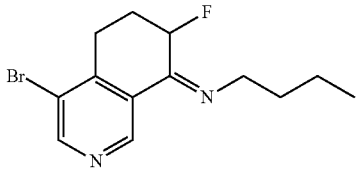 [SMILES: CCCC/N=C1/c2cncc(Br)c2CCC1F]

A mixture solution of NFSi (N-fluorodibenzenesulfonimide) (3.2 g, 10.2 mmol), $K_2CO_3$ (3.6 g, 25.6 mmol) and molecular sieves (10.0 g) in $CH_3CN$ (100 mL) and DMF (20 mL) was stirred at room temperature for 30 min before [4-bromo-6,7-dihydro-5H-isoquinolin-(8E)-ylidene]-butyl-amine (1.8 g, 6.4 mmol) was added. The resulting mixture was stirred at room temperature for 12 hr before $Et_3N$ was added at 0° C. and stirring was continued for 10 min. The mixture was filtered and extracted with EtOAc (2×100 mL). Combined organics were washed with brine, dried over anhy. $Na_2SO_4$, filtered and concentrated in vacuo to afford the title compound (1.8 g, 93% yield) as a brown solid. MS: 299.1 & 301.1 (M+H)⁺.

[C] (rac)-4-Bromo-7-fluoro-6,7-dihydro-5H-isoquinolin-8-one

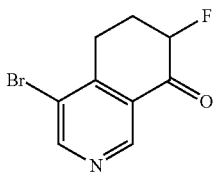

A solution of [4-bromo-7-fluoro-6,7-dihydro-5H-isoquinolin-(8Z)-ylidene]-butyl-amine (1.8 g, 6.02 mmol), 37% HCl (1.5 mL) in $CH_3CN$ (10 mL) was stirred at room temperature for 30 min, then it was concentrated in vacuo to afford a yellow oil, which was extracted with EtOAc (2×80 mL). The combined organics were washed with brine, dried over anhy. $Na_2SO_4$, filtered and concentrated in vacuo to afford the title compound (1.41 g, 96% yield) as a brown solid. MS: 244.1 & 246.1 (M+H)⁺.

[D] (all rac)-4-Bromo-7-fluoro-5,6,7,8-tetrahydro-isoquinolin-8-ylamine

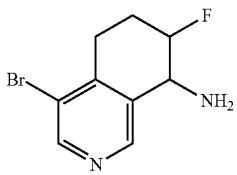 [SMILES: NC1c2cncc(Br)c2CCC1F]

A mixture solution of (rac)-4-bromo-7-fluoro-6,7-dihydro-5H-isoquinolin-8-one (890 mg, 3.6 mmol), $NaBH_3CN$ (226 mg, 3.6 mmol) and $CH_3COONH_4$ (2.8 g, 36 mmol) in isopropanol (20 mL) was refluxed for 3 hr. It was then cooled to room temperature and concentrated in vacuo to afford a yellow oil, which was extracted with EtOAc (2×100 mL). Combined organics were washed with brine, dried over anhy. $Na_2SO_4$, filtered and concentrated in vacuo to afford the title compound (705 mg, 80% yield) as a brown solid. MS: 245.1 & 247.1 (M+H)⁺.

[E] (all rac)-N-(4-Bromo-7-fluoro-5,6,7,8-tetrahydro-isoquinolin-8-yl)-propionamide

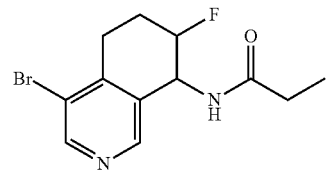 [SMILES: CCC(=O)NC1c2cncc(Br)c2CCC1F]

To a stirred solution of (all rac)-4-bromo-7-fluoro-5,6,7,8-tetrahydro-isoquinolin-8-ylamine (670 mg, 2.73 mmol) and $Et_3N$ (1.0 mL) in DCM (20 mL) was added propionyl chloride (0.26 mL, 3.01 mmol) at 0° C. and the mixture was stirred for 1 hr. It was then extracted with EtOAc (2×100 mL) and combined organics were washed with brine, dried over anhy. $Na_2SO_4$, filtered and concentrated in vacuo. The residue was purified by silica gel flash chromatography eluting with a 0 to 50% EtOAc-heptane gradient to give the title compound (600 mg, 73% yield) as a light yellow solid. MS: 301.1 & 303.1 (M+H)⁺.

Example 1

(rac)-N-(4-(1-Methyl-2-oxo-1,2,3,4-tetrahydroquinolin-6-yl)-5,6,7,8-tetrahydroisoquinolin-8-yl)propionamide

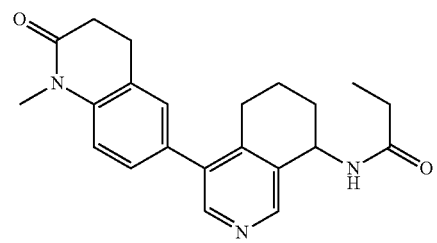 [SMILES: CCC(=O)NC1CCCc2c(-c3ccc4c(c3)CCC(=O)N4C)cncc21]

To a stirred brown solution of (rac)-6-(8-amino-5,6,7,8-tetrahydroisoquinolin-4-yl)-1-methyl-3,4-dihydroquinolin-2(1H)-one (intermediate A-2) (92.2 mg, 0.30 mmol) and propionic acid (24.4 mg, 0.33 mmol) in $CH_2Cl_2$ (1.5 mL) at 0° C. under Argon was added EDCI (63.3 mg, 0.33 mmol). Stirring was continued over night and the reaction mixture was allowed to warm up to room temperature. The reaction mixture was poured into aq. 10% $KH_2PO_4$ solution followed by extraction with AcOEt (3×). The organic phases were washed once with aq. 10% $KH_2PO_4$, aq. sat. $NaHCO_3$ and with aq. sat. NaCl solution; the combined organic phases were dried over Na$_2$SO$_4$, filtered and evaporated to afford the title compound (111 mg, quantitative) as light yellow foam. MS: 364.2 (M+H$^+$).

Example 2 and Example 3

(−)-(R or S)—N-(4-(1-Methyl-2-oxo-1,2,3,4-tetrahydroquinolin-6-yl)-5,6,7,8-tetrahydroisoquinolin-8-yl)propionamide and (+)-(S or R)—N-(4-(1-Methyl-2-oxo-1,2,3,4-tetrahydroquinolin-6-yl)-5,6,7,8-tetrahydroisoquinolin-8-yl)propionamide Example 2

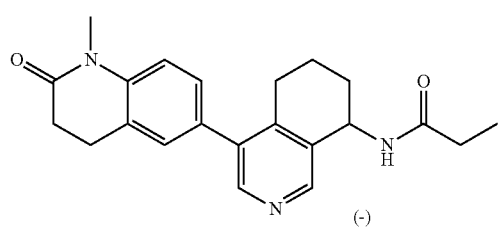

(−)

Example 3

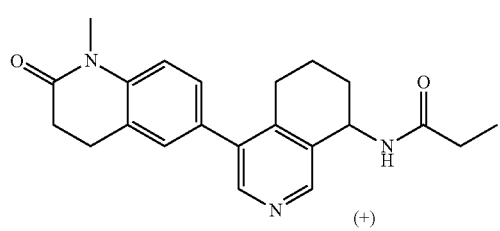

(+)

The title compounds were prepared by chiral separation of (rac)-N-(4-(1-methyl-2-oxo-1,2,3,4-tetrahydroquinolin-6-yl)-5,6,7,8-tetrahydroisoquinolin-8-yl)propionamide (example 1) on a Chiralpak AD (40% 2-propanol in n-heptane) to give after precipitation from CH$_2$Cl$_2$ with n-pentane 28% of (−)-(R or S)—N-(4-(1-methyl-2-oxo-1,2,3,4-tetrahydroquinolin-6-yl)-5,6,7,8-tetrahydroisoquinolin-8-yl)propionamide (example 2) as off-white powder, MS: 364.2 (M+H$^+$) and 26% of (+)-(S or R)—N-(4-(1-methyl-2-oxo-1,2,3,4-tetrahydroquinolin-6-yl)-5,6,7,8-tetrahydroisoquinolin-8-yl)propionamide (example 3) as off-white powder. MS: 364.2 (M+H$^+$).

Example 3-1

(+)-(R)—N-(4-(1-Methyl-2-oxo-1,2,3,4-tetrahydroquinolin-6-yl)-5,6,7,8-tetrahydroisoquinolin-8-yl)propionamide Example 3-1

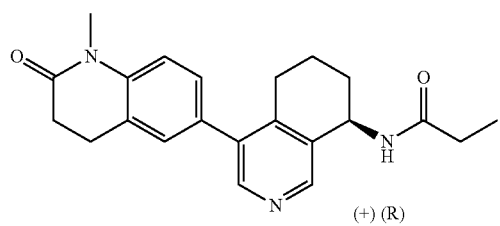

(+) (R)

In analogy to the procedures described for the preparation of intermediate A-2 [E] and for the preparation of intermediate B-1, Suzuki reaction of (+)-(R)-4-bromo-5,6,7,8-tetrahydroisoquinolin-8-amine (intermediate B-3b) with 1-methyl-6-(4,4,5,5-tetramethyl-[1,3,2]dioxaborolan-2-yl)-3,4-dihydro-1H-quinolin-2-one (intermediate A-1) gave (R)-6-(8-amino-5,6,7,8-tetrahydroisoquinolin-4-yl)-1-methyl-3,4-dihydroquinolin-2(1H)-one and after subsequent reaction with propionyl chloride the title compound as colorless solid. MS: 364.2 (M+H$^+$).

Example 4

(rac)-N-(4-(1-Methyl-2-oxo-1,2,3,4-tetrahydroquinolin-6-yl)-5,6,7,8-tetrahydroisoquinolin-8-yl)ethanesulfonamide

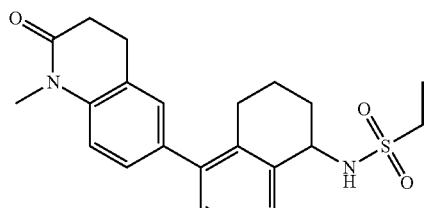

A cooled (0° C.) brown solution of (rac)-6-(8-amino-5,6,7,8-tetrahydroisoquinolin-4-yl)-1-methyl-3,4-dihydroquinolin-2(1H)-one (intermediate A-2) (61.5 mg, 200 μmol) in CH$_2$Cl$_2$ (3.0 ml) was treated with ethanesulfonyl chloride (65.6 mg, 48.3 μL, 500 μmol) and Et$_3$N (40.5 mg, 55.8 μL, 400 μmol). After ½ h the mixture was concentrated in vacuo and purified by flash chromatography (20 g SiO$_2$, Telos-cartridge, CH$_2$Cl$_2$/MeOH (1 to 5%)) to give 100 mg of the title compound together with Et$_3$N×HCl as impurity. Extraction with H$_2$O/EtOAc (3×), and precipitation CH$_2$Cl$_2$/n-pentane gave the pure title compound (46 mg, 58%) as a yellow powder. MS: 400.2 (M+H$^+$).

Example 5 and Example 6

(−)-(R or S)—N-(4-(1-Methyl-2-oxo-1,2,3,4-tetrahydroquinolin-6-yl)-5,6,7,8-tetrahydroisoquinolin-8-yl)ethanesulfonamide and (+)-(S or R)—N-(4-(1-Methyl-2-oxo-1,2,3,4-tetrahydroquinolin-6-yl)-5,6,7,8-tetrahydroisoquinolin-8-yl)ethanesulfonamide Example 5

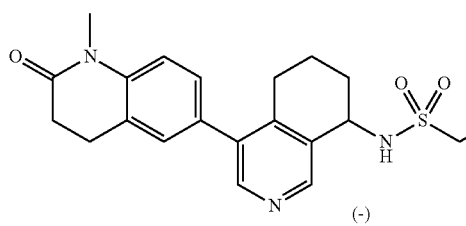

(−)

Example 6

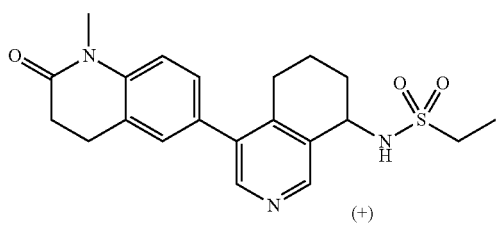

The title compounds were prepared by chiral separation of (rac)-N-(4-(1-methyl-2-oxo-1,2,3,4-tetrahydroquinolin-6-yl)-5,6,7,8-tetrahydroisoquinolin-8-yl)ethanesulfonamide (example 4) on a Chiralpak AD (40% 2-propanol in n-heptane) to give after precipitation from $CH_2Cl_2$ with n-pentane 26% of (−)-(R or S)—N-(4-(1-methyl-2-oxo-1,2,3,4-tetrahydroquinolin-6-yl)-5,6,7,8-tetrahydroisoquinolin-8-yl)ethanesulfonamide (example 5) as off-white powder, MS: 400.2 (M+H$^+$) and 25% of (+)-(S or R)—N-(4-(1-methyl-2-oxo-1,2,3,4-tetrahydroquinolin-6-yl)-5,6,7,8-tetrahydroisoquinolin-8-yl)ethanesulfonamide (example 6) as off-white powder. MS: 400.2 (M+H$^+$).

Example 7

(rac)-N-(4-(1-Methyl-2-oxo-1,2,3,4-tetrahydroquinolin-6-yl)-6,7-dihydro-5H-cyclopenta[c]pyridin-7-yl)propionamide

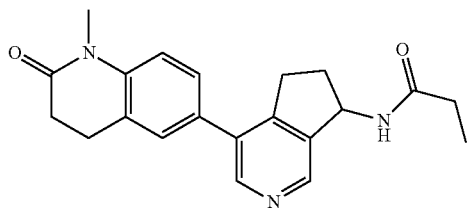 [SMILES: CCC(=O)NC1CCc2c(-c3ccc4c(c3)CCC(=O)N4C)cncc21]

In analogy to the procedure described for the preparation of intermediate A-2 [E], (rac)-N-(4-bromo-6,7-dihydro-5H-cyclopenta[c]pyridin-7-yl)propionamide (intermediate A-3) was reacted with 1-methyl-6-(4,4,5,5-tetramethyl-1,3,2-dioxaborolan-2-yl)-3,4-dihydroquinolin-2(1H)-one (intermediate A-1) to give the title compound as an off-white powder in 87% yield. MS: 350.2 (M+H$^+$).

Example 8 and Example 9

(−)-(R or S)—N-(4-(1-Methyl-2-oxo-1,2,3,4-tetrahydroquinolin-6-yl)-6,7-dihydro-5H-cyclopenta[c]pyridin-7-yl)propionamide and (+)-(S or R)—N-(4-(1-Methyl-2-oxo-1,2,3,4-tetrahydroquinolin-6-yl)-6,7-dihydro-5H-cyclopenta[c]pyridin-7-yl)propionamide Example 8

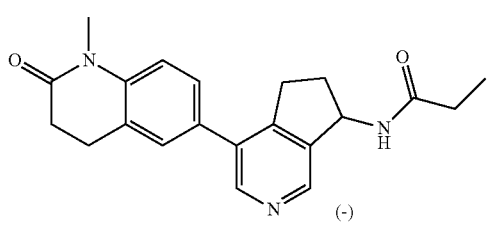

Example 9

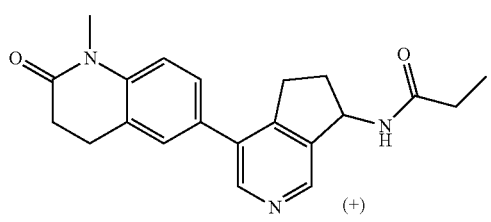

The title compounds were prepared by chiral separation of (rac)-N-(4-(1-methyl-2-oxo-1,2,3,4-tetrahydroquinolin-6-yl)-6,7-dihydro-5H-cyclopenta[c]pyridin-7-yl)propionamide (example 7) on a Chiralpak AD (30% 2-propanol in n-heptane) to give after precipitation from $CH_2Cl_2$ with n-pentane 32% of (−)-(R or S)—N-(4-(1-methyl-2-oxo-1,2,3,4-tetrahydroquinolin-6-yl)-6,7-dihydro-5H-cyclopenta[c]pyridin-7-yl)propionamide (example 8) as off-white powder, MS: 350.2 (M+H$^+$) and 30% of (+)-(S or R)—N-(4-(1-methyl-2-oxo-1,2,3,4-tetrahydroquinolin-6-yl)-6,7-dihydro-5H-cyclopenta[c]pyridin-7-yl)propionamide (example 9) as off-white powder. MS: 350.2 (M+H$^+$).

Example 10

(rac)-N-(4-(1-Methyl-2-oxo-1,2,3,4-tetrahydroquinolin-6-yl)-6,7-dihydro-5H-cyclopenta[c]pyridin-7-yl)ethanesulfonamide

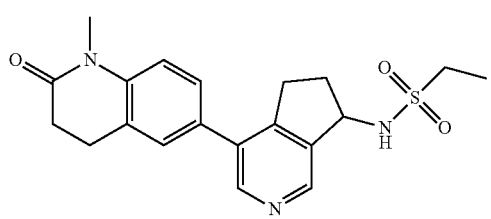 [SMILES: CCS(=O)(=O)NC1CCc2c(-c3ccc4c(c3)CCC(=O)N4C)cncc21]

In analogy to the procedure described for the preparation of example 4, (rac)-6-(7-amino-6,7-dihydro-5H-cyclopenta[c]pyridin-4-yl)-1-methyl-3,4-dihydroquinolin-2(1H)-one (intermediate A-4) and ethanesulfonyl chloride gave the title compound as an off-white powder in 39% yield. MS: 386.2 (M+H$^+$).

Example 11

{2-[5-(1-Methyl-2-oxo-1,2,3,4-tetrahydro-quinolin-6-yl)-3,4-dihydro-2H-[1,7]naphthyridin-1-yl]-ethyl}-carbamic acid tert-butyl ester

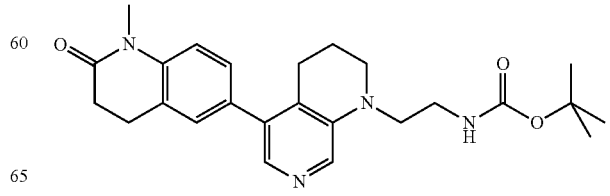

To a solution of 1-methyl-6-(1,2,3,4-tetrahydro-1,7-naphthyridin-5-yl)-3,4-dihydroquinolin-2(1H)-one (intermediate A-5, 0.1 g, 0.341 mmol) in DCE (3 mL)/THF (1.5 mL) were added tert-butyl 2-oxoethylcarbamate (0.081 g, 0.511 mmol), acetic acid (0.02 g, 0.341 mmol) and the reaction mixture was stirred at room temperature for 10 min. Then, sodium triacetoxyborohydride (0.144 g, 0.682 mmol) was added and stirring was continued at room temperature over night. Then, the mixture was diluted with DCM, poured into aq NaHCO3 and extracted with DCM (2×25 mL). Combined organics were washed with brine, dried over $Na_2SO_4$, filtered and evaporated to dryness. The residue was purified by reverse phase HPLC on a Gemini-NX column, eluting with a 20 to 98% MeOH—$H_2O$ (0.05% TEA) gradient to give the title compound (0.036 g, 24%) as a white foam. MS: 437.2 (M+H$^+$).

Example 12

6-[1-(2-Amino-ethyl)-1,2,3,4-tetrahydro-[1,7]naphthyridin-5-yl]-1-methyl-3,4-dihydro-1H-quinolin-2-one hydrochloride

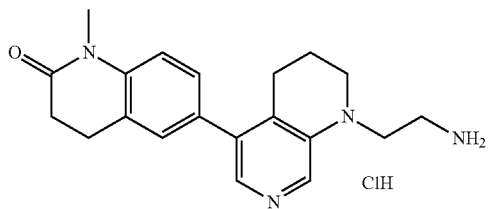 [SMILES: CN1C(=O)CCc2cc(-c3cncc4c3CCCN4CCN)ccc21 ; Cl]

To a solution of {2-[5-(1-methyl-2-oxo-1,2,3,4-tetrahydro-quinolin-6-yl)-3,4-dihydro-2H-[1,7]naphthyridin-1-yl]-ethyl}-carbamic acid tert-butyl ester (example 11, 0.06 g, 0.137 mmol) in MeOH (1 mL) was added 4M HCl in dioxane (0.137 mL, 0.550 mmol) and the reaction mixture was stirred at room temperature over night. Then, the reaction mixture was evaporated to dryness and the solid residue was triturated in diethyl ether, filtered off and further dried on the high vacuum to give the title compound (0.040 g, 70%) as an orange solid. MS: 337.3 (M+H$^+$).

Example 13

N-{2-[5-(1-Methyl-2-oxo-1,2,3,4-tetrahydro-quinolin-6-yl)-3,4-dihydro-2H-[1,7]naphthyridin-1-yl]-ethyl}-propionamide

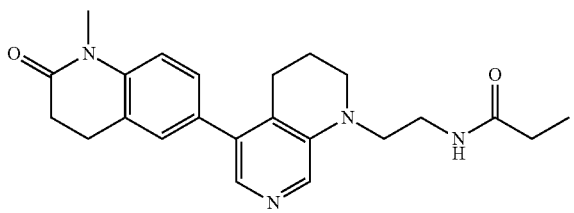 [SMILES: CCC(=O)NCCN1CCCc2c(-c3ccc4c(c3)CCC(=O)N4C)cncc21]

To a solution of 6-[1-(2-amino-ethyl)-1,2,3,4-tetrahydro-[1,7]naphthyridin-5-yl]-1-methyl-3,4-dihydro-1H-quinolin-2-one hydrochloride (example 12, 0.037 g, 0.099 mmol) in dry DMF (1.5 mL) were added TBTU ((O-(benzotriazol-1-yl)-N,N,N',N'-tetramethyluronium tetrafluoroborate) 0.038 g, 0.119 mmol), Hünig's base (0.032 g, 0.248 mmol) and propionic acid (0.015 g, 0.198 mmol) and the reaction mixture was stirred at room temperature over night. Then, the reaction mixture was diluted with EtOAc, poured into sat. $NaHCO_3$ solution (5 mL) and extracted with EtOAc (2×10 mL). Combined organics were dried over $Na_2SO_4$, filtered and evaporated to dryness. The residue was purified by silica gel flash chromatography eluting with a 0 to 10% MeOH (1% $NH_4OH$)-DCM gradient to give the title compound (0.023 g, 59%) as a yellow solid. MS: 393.2 (M+H$^+$).

Example 14

N-(2-(5-(1-Methyl-2-oxo-1,2,3,4-tetrahydroquinolin-6-yl)-3,4-dihydro-1,7-naphthyridin-1(2H)-yl)ethyl)ethanesulfonamide

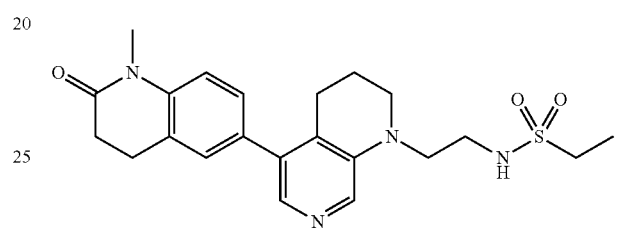

To a solution of 6-[1-(2-amino-ethyl)-1,2,3,4-tetrahydro-[1,7]naphthyridin-5-yl]-1-methyl-3,4-dihydro-1H-quinolin-2-one hydrochloride (example 12, 0.03 g, 0.081 mmol) in DCM (1 mL) were added triethylamine (0.020 g, 0.201 mmol) and ethanesulfonylchloride (0.011 g, 0.089 mmol) and the reaction mixture was stirred at room temperature for 1.5 h. The mixture was diluted with DCM, poured into $H_2O$ (5 mL) and extracted with DCM (2×10 mL). Combined organics were dried over $Na_2SO_4$, filtered and evaporated to dryness. The residue was purified by silica gel flash chromatography eluting with a 0 to 5% MeOH-DCM gradient to give the title compound (0.01 g, 29%) as a yellow oil. MS: 429.2 (M+H$^+$).

Example 15

(2R,S)-2-Hydroxy-N-[(4R,S)-4-(1-methyl-2-oxo-1,2,3,4-tetrahydroquinolin-6-yl)-5,6,7,8-tetrahydroisoquinolin-8-yl]propanamide

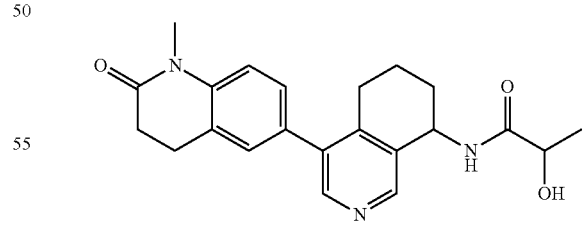

To a stirred yellow solution of (rac)-6-(8-amino-5,6,7,8-tetrahydroisoquinolin-4-yl)-1-methyl-3,4-dihydroquinolin-2(1H)-one (intermediate A-2) (80.0 mg, 0.26 mmol), 1-hydroxylbenzotriazole monohydrate (39.5 mg, 0.29 mmol) and DL-lactic acid (0.027 mL, 0.36 mmol) in $CH_2Cl_2$ (2.6 mL) at 0° C. under Argon was added EDCI (59.9 mg, 0.31 mmol). Stirring was continued over night and the reaction mixture was allowed to warm up to room temperature. Again, 1-hydroxylbenzotriazole monohydrate (39.5 mg, 0.29 mmol), N,N-diisopropylethylamine (0.046 mL, 0.26 mmol), DL-lactic acid (0.023 mL, 0.31 mmol) and at 0° C. EDCI (49.9 mg, 0.26 mmol) was added. Stirring was continued for ½ h at 0° C. and 2.5 h at room temperature. The reaction mixture was then poured into aq. 10% KH$_2$PO$_4$ solution followed by extraction with AcOEt (3×). The organic phases were washed once with aq. 10% KH$_2$PO$_4$, aq. sat. NaHCO$_3$ and with aq. sat. NaCl solution; the combined organic phases were dried over Na$_2$SO$_4$, filtered and evaporated to dryness. The residue was purified by silica gel flash chromatography eluting with a 5 to 10% 2-propanol-CH$_2$Cl$_2$ gradient to give the title compound (0.042 mg, 43%) as an off white powder. MS: 380.2 (M+H$^+$).

Example 16

(2R)-2-Hydroxy-N-((4R,S)-4-(1-methyl-2-oxo-1,2,3,4-tetrahydroquinolin-6-yl)-5,6,7,8-tetrahydroisoquinolin-8-yl)propanamide

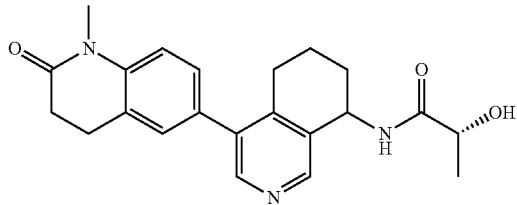 [SMILES: C[C@@H](O)C(=O)NC1CCCc2c(-c3ccc4c(c3)CCC(=O)N4C)cncc21]

To a stirred yellow solution of (rac)-6-(8-amino-5,6,7,8-tetrahydroisoquinolin-4-yl)-1-methyl-3,4-dihydroquinolin-2(1H)-one (intermediate A-2) (100.0 mg, 0.33 mmol), 1-hydroxylbenzotriazole monohydrate (49.3 mg, 0.36 mmol), (R)-2-hydroxypropanoic acid (0.035 mg, 0.39 mmol) and N,N-diisopropylethylamine (0.068 mL, 0.39 mmol) in CH$_2$Cl$_2$ (2.6 mL) at 0° C. under Argon was added EDCI (74.8 mg, 0.39 mmol). Stirring was continued over night and the reaction mixture was allowed to warm up to room temperature. The reaction mixture was poured into aq. 10% KH$_2$PO$_4$ solution followed by extraction with AcOEt (3×). The organic phases were washed once with aq. 10% KH$_2$PO$_4$, aq. sat. NaHCO$_3$ and with aq. sat. NaCl solution; the combined organic phases were dried over Na$_2$SO$_4$, filtered, evaporated and precipitated from CH$_2$Cl$_2$/Et2O to give the title compound (0.093 mg, 75%) as a light yellow powder. MS: 380.2 (M+H$^+$).

Example 17

(2S)-2-Hydroxy-N-((4R,S)-4-(1-methyl-2-oxo-1,2,3,4-tetrahydroquinolin-6-yl)-5,6,7,8-tetrahydroisoquinolin-8-yl)propanamide

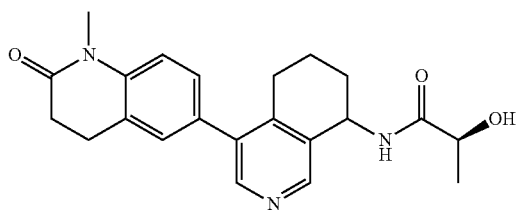 [SMILES: C[C@H](O)C(=O)NC1CCCc2c(-c3ccc4c(c3)CCC(=O)N4C)cncc21]

In analogy to the procedure described for the preparation of example 16, (rac)-6-(8-amino-5,6,7,8-tetrahydroisoquinolin-4-yl)-1-methyl-3,4-dihydroquinolin-2(1H)-one (intermediate A-2) and (S)-2-hydroxypropanoic acid gave the title compound as a light yellow powder in 78% yield. MS: 380.2 (M+H$^+$).

Example 18 and Example 19

(+)-(2R)-2-Hydroxy-N-((4R or 4S)-4-(1-methyl-2-oxo-1,2,3,4-tetrahydroquinolin-6-yl)-5,6,7,8-tetrahydroisoquinolin-8-yl)propanamide and (−)-(2R)-2-Hydroxy-N-((4S or 4R)-4-(1-methyl-2-oxo-1,2,3,4-tetrahydroquinolin-6-yl)-5,6,7,8-tetrahydroisoquinolin-8-yl)propanamide Example 18

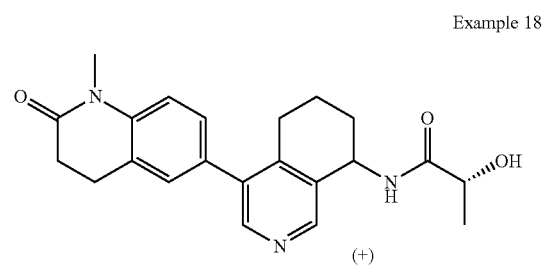 [SMILES: C[C@@H](O)C(=O)NC1CCCc2c(-c3ccc4c(c3)CCC(=O)N4C)cncc21]

Example 19

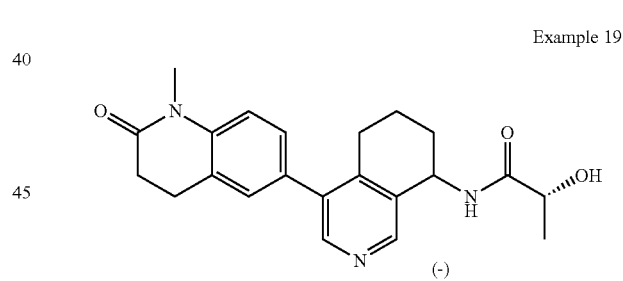

The title compounds were prepared by chiral separation of (2R)-2-hydroxy-N-((4R,S)-4-(1-methyl-2-oxo-1,2,3,4-tetrahydroquinolin-6-yl)-5,6,7,8-tetrahydroisoquinolin-8-yl)propanamide (example 16) on a Lux 5u Amylose-2 column (40% ethanol in n-heptane) to give after precipitation from CH$_2$Cl$_2$ with n-pentane 41% of (+)-(2R)-2-hydroxy-N-((4R or 4S)-4-(1-methyl-2-oxo-1,2,3,4-tetrahydroquinolin-6-yl)-5,6,7,8-tetrahydroisoquinolin-8-yl)propanamide (example 18) as off-white powder, MS: 380.2 (M+H$^+$) and 41% of (−)-(2R)-2-hydroxy-N-((4S or 4R)-4-(1-methyl-2-oxo-1,2,3,4-tetrahydroquinolin-6-yl)-5,6,7,8-tetrahydroisoquinolin-8-yl)propanamide (example 19) as light yellow powder. MS: 380.2 (M+H$^+$).

Example 20 and Example 21

(−)-(2S)-2-Hydroxy-N-((4S or 4R)-4-(1-methyl-2-oxo-1,2,3,4-tetrahydroquinolin-6-yl)-5,6,7,8-tetrahydroisoquinolin-8-yl)propanamide and (+)-(2S)-2-Hydroxy-N-((4R or 4S)-4-(1-methyl-2-oxo-1,2,3,4-tetrahydroquinolin-6-yl)-5,6,7,8-tetrahydroisoquinolin-8-yl)propanamide

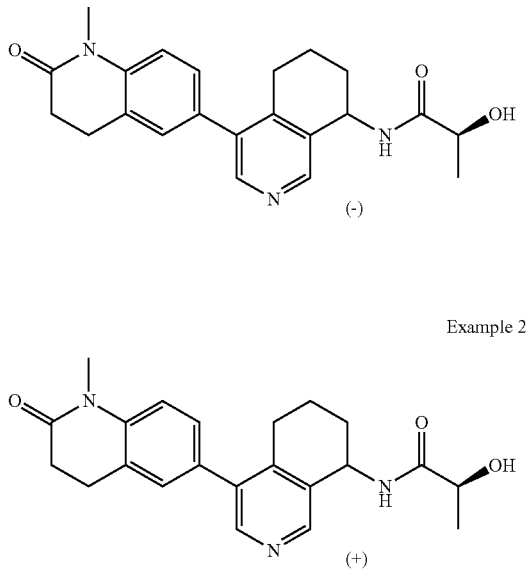

The title compounds were prepared by chiral separation of (2S)-2-hydroxy-N-((4R,S)-4-(1-methyl-2-oxo-1,2,3,4-tetrahydroquinolin-6-yl)-5,6,7,8-tetrahydroisoquinolin-8-yl)propanamide (example 17) on a Reprosil Chiral NR column (40% ethanol in n-heptane) to give after precipitation from $CH_2Cl_2$ with n-pentane 39% of (−)-(2S)-2-hydroxy-N-((4S or 4R)-4-(1-methyl-2-oxo-1,2,3,4-tetrahydroquinolin-6-yl)-5,6,7,8-tetrahydroisoquinolin-8-yl)propanamide (example 20) as off-white powder, MS: 380.2 (M+H$^+$) and 41% of (+)-(2S)-2-hydroxy-N-((4R or 4S)-4-(1-methyl-2-oxo-1,2,3,4-tetrahydroquinolin-6-yl)-5,6,7,8-tetrahydroisoquinolin-8-yl)propanamide (example 21) as off-white powder. MS: 380.2 (M+H$^+$).

Example 22

(rac)-N-(4-(7-Fluoro-1-methyl-2-oxo-1,2,3,4-tetrahydroquinolin-6-yl)-6,7-dihydro-5H-cyclopenta[c]pyridin-7-yl)propionamide

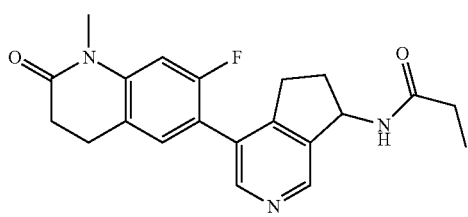 [SMILES: CCC(=O)NC1CCc2c(-c3cc4c(cc3F)N(C)C(=O)CC4)cncc21]

In analogy to the procedure described for the preparation of intermediate A-2 [E], (rac)-N-(4-bromo-6,7-dihydro-5H-cyclopenta[c]pyridin-7-yl)propanamide (intermediate A-3) was reacted with 7-fluoro-1-methyl-6-(4,4,5,5-tetramethyl-[1,3,2]dioxaborolan-2-yl)-3,4-dihydro-1H-quinolin-2-one (intermediate A-9) to give the title compound as a light brown solid in 72% yield. MS: 368.2 (M+H$^+$).

Example 23 and Example 24

(−)-(S or R)—N-(4-(7-Fluoro-1-methyl-2-oxo-1,2,3,4-tetrahydroquinolin-6-yl)-6,7-dihydro-5H-cyclopenta[c]pyridin-7-yl)propionamide and (+)-(R or S)—N-(4-(7-Fluoro-1-methyl-2-oxo-1,2,3,4-tetrahydroquinolin-6-yl)-6,7-dihydro-5H-cyclopenta[c]pyridin-7-yl)propionamide

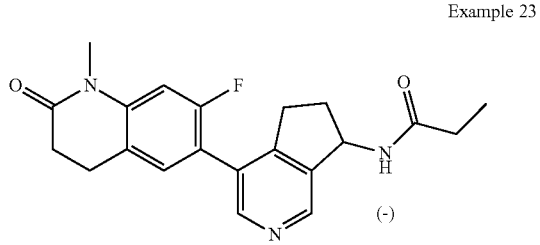

The title compounds were prepared by chiral separation of (rac)-N-(4-(7-fluoro-1-methyl-2-oxo-1,2,3,4-tetrahydroquinolin-6-yl)-6,7-dihydro-5H-cyclopenta[c]pyridin-7-yl)propionamide (example 22) on a Chiralpak AD column (40% ethanol in n-heptane) to give after precipitation from $CH_2Cl_2$ with n-pentane 43% of (−)-(S or R)—N-(4-(7-fluoro-1-methyl-2-oxo-1,2,3,4-tetrahydroquinolin-6-yl)-6,7-dihydro-5H-cyclopenta[c]pyridin-7-yl)propionamide (example 23) as off-white solid, MS: 368.2 (M+H$^+$) and 41% of (+)-(R or S)—N-(4-(7-fluoro-1-methyl-2-oxo-1,2,3,4-tetrahydroquinolin-6-yl)-6,7-dihydro-5H-cyclopenta[c]pyridin-7-yl)propionamide (example 24) as off-white solid. MS: 368.2 (M+H$^+$).

Example 25

(rac)-N-(4-(7-Fluoro-1-methyl-2-oxo-1,2,3,4-tetrahydroquinolin-6-yl)-6,7-dihydro-5H-cyclopenta[c]pyridin-7-yl)ethanesulfonamide

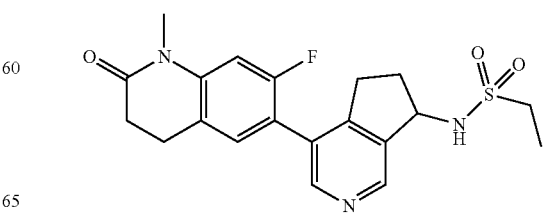

In analogy to the procedure described for the preparation of intermediate A-2 [E], (rac)-N-(4-bromo-6,7-dihydro-5H-cyclopenta[c]pyridin-7-yl)ethanesulfonamide (intermediate A-6) was reacted with 7-fluoro-1-methyl-6-(4,4,5,5-tetramethyl-[1,3,2]dioxaborolan-2-yl)-3,4-dihydro-1H-quinolin-2-one (intermediate A-9). The Suzuki coupling had to be repeated three times to give the to give the title compound as off-white solid in 70% yield. MS: 404.1 (M+H$^+$).

Example 26 and Example 27

(−)-(S or R)—N-(4-(7-Fluoro-1-methyl-2-oxo-1,2,3,4-tetrahydroquinolin-6-yl)-6,7-dihydro-5H-cyclopenta[c]pyridin-7-yl)ethanesulfonamide and (+)-(R or S)—N-(4-(7-Fluoro-1-methyl-2-oxo-1,2,3,4-tetrahydroquinolin-6-yl)-6,7-dihydro-5H-cyclopenta[c]pyridin-7-yl)ethanesulfonamide Example 26

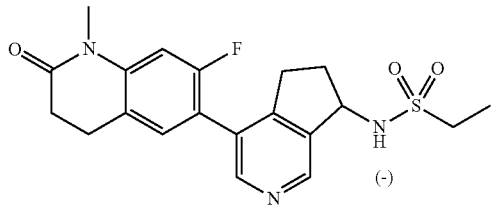

(−)

Example 27

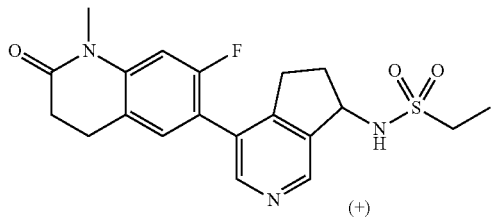

(+)

The title compounds were prepared by chiral separation of (rac)-N-(4-(7-fluoro-1-methyl-2-oxo-1,2,3,4-tetrahydroquinolin-6-yl)-6,7-dihydro-5H-cyclopenta[c]pyridin-7-yl)ethanesulfonamide (example 25) on a Chiralpak AD column (40% 2-propanol in n-heptane) to give after precipitation from CH$_2$Cl$_2$ with n-pentane 38% of (−)-(S or R)—N-(4-(7-fluoro-1-methyl-2-oxo-1,2,3,4-tetrahydroquinolin-6-yl)-6,7-dihydro-5H-cyclopenta[c]pyridin-7-yl)ethanesulfonamide (example 26) as off-white solid, MS: 404.1 (M+H$^+$) and 38% of (+)-(R or S)—N-(4-(7-fluoro-1-methyl-2-oxo-1,2,3,4-tetrahydroquinolin-6-yl)-6,7-dihydro-5H-cyclopenta[c]pyridin-7-yl)ethanesulfonamide (example 27) as off-white solid. MS: 404.1 (M+H$^+$).

Example 28

(rac)-N-[4-(7-Fluoro-1-methyl-2-oxo-1,2,3,4-tetrahydro-quinolin-6-yl)-5,6,7,8-tetrahydro isoquinolin-8-yl]-propionamide

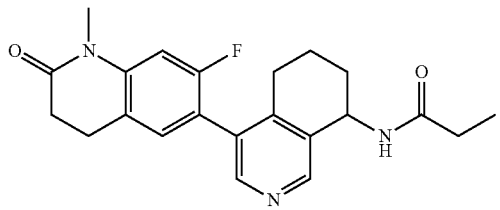 [SMILES: CCC(=O)NC1CCCc2c(-c3cc4c(cc3F)N(C)C(=O)CC4)cncc21]

A mixture of 7-fluoro-1-methyl-6-(4,4,5,5-tetramethyl-[1,3,2]dioxaborolan-2-yl)-3,4-dihydro-1H-quinolin-2-one (intermediate A-9, 168 mg, 0.55 mmol) and (rac)-N-(4-bromo-5,6,7,8-tetrahydro-isoquinolin-8-yl)-propionamide (intermediate B-1) (142 mg, 0.5 mmol) in DMF (3 mL) was purged with argon for 1 min before bis(triphenylphosphine)palladium (II)chloride (38 mg, 0.054 mmol) and 1 N aq. Na$_2$CO$_3$ (2.5 mL) were added. The resulting reaction mixture was purged with argon for 2 min, and heated at 100° C. for 45 min in a microwave. After cooling to room temperature, the reaction mixture was diluted with EtOAc (5 mL) before it was poured into a satd. aq. solution of NaHCO$_3$ (10 mL). The aqueous layer was extracted with EtOAc (3×5 mL) and the combined organic layers were washed with water and brine, dried over anhy. Na$_2$SO$_4$, filtered and concentrated in vacuo. The residue was purified by prep-HPLC to give the title compound (120 mg, 63% yield) as a white solid. MS: 382.3 (M+H)+

Example 29 and Example 30

(−)-(S or R)—N-[4-(7-Fluoro-1-methyl-2-oxo-1,2,3,4-tetrahydro-quinolin-6-yl)-5,6,7,8-tetrahydro-isoquinolin-8-yl]-propionamide and (+)-(R or S)—N-[4-(7-fluoro-1-methyl-2-oxo-1,2,3,4-tetrahydro-quinolin-6-yl)-5,6,7,8-tetrahydro-isoquinolin-8-yl]-propionamide Example 29

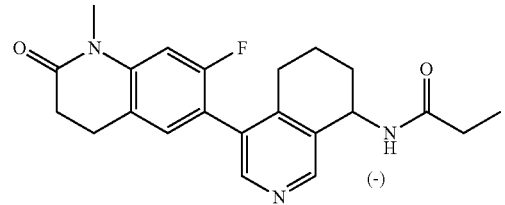

(−)

Example 30

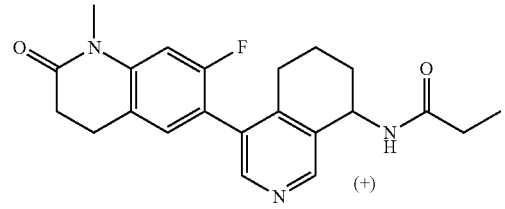

(+)

The title compounds were prepared by chiral separation of (rac)-N-[4-(7-fluoro-1-methyl-2-oxo-1,2,3,4-tetrahydro-quinolin-6-yl)-5,6,7,8-tetrahydro-isoquinolin-8-yl]-propionamide (example 28) to give (−)-(S or R)—N-[4-(7-fluoro-1-methyl-2-oxo-1,2,3,4-tetrahydro-quinolin-6-yl)-5,6,7,8-tetrahydro-isoquinolin-8-yl]-propionamide (example 29) as a white solid, MS: 382.3 (M+H)$^+$ and (+)-(R or S)—N-[4-(7-fluoro-1-methyl-2-oxo-1,2,3,4-tetrahydro-quinolin-6-yl)-5,6,7,8-tetrahydro-isoquinolin-8-yl]-propionamide (example 30) as a white solid. MS: 382.3 (M+H)$^+$.

Example 31 and Example 32

(−)-(S or R)-Ethanesulfonic acid [4-(7-fluoro-1-methyl-2-oxo-1,2,3,4-tetrahydro-quinolin-6-yl)-5,6,7,8-tetrahydro-isoquinolin-8-yl]-amide and (+)-(R or S)-Ethanesulfonic acid [4-(7-fluoro-1-methyl-2-oxo-1,2,3,4-tetrahydro-quinolin-6-yl)-5,6,7,8-tetrahydro-isoquinolin-8-yl]-amide Example 31

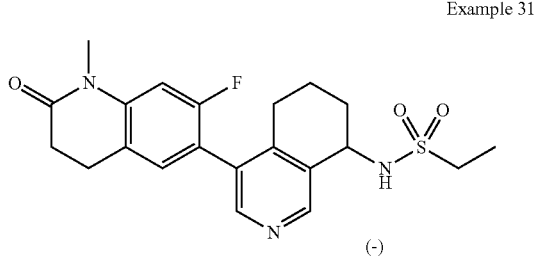

(−)

Example 32

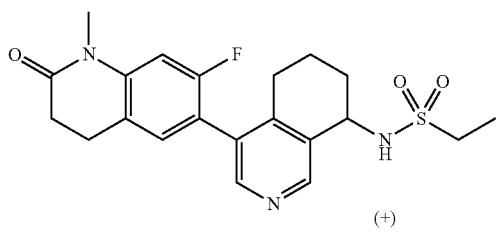

(+)

A mixture of 7-fluoro-1-methyl-6-(4,4,5,5-tetramethyl-[1,3,2]dioxaborolan-2-yl)-3,4-dihydro-1H-quinolin-2-one (intermediate A-9) (168 mg, 0.55 mmol) and (rac)-ethanesulfonic acid (4-bromo-5,6,7,8-tetrahydro-isoquinolin-8-yl)-amide (intermediate B-4) (160 mg, 0.5 mmol) in DMF (3 mL) was purged with argon for 1 min before bis(triphenylphosphine)palladium (II)chloride (38 mg, 0.054 mmol) and 1 N aq. Na$_2$CO$_3$ (2.5 mL) were added. The resulting reaction mixture was purged with argon for 2 min and then heated at 100° C. for 45 min in a microwave. After cooling to room temperature, the reaction mixture was diluted with EtOAc (5 mL) before it was poured into a satd. aq. solution of NaHCO$_3$ (10 mL). The aqueous layer was extracted with EtOAc (3×5 mL) and combined organics were washed with water and brine (20 mL), dried over anhy. Na$_2$SO$_4$, filtered and concentrated in vacuo. The residue was then purified by Prep-HPLC to give a racemic mixture of the title compound (150 mg, 68% yield). This racemic mixture was then separated by chiral HPLC to afford (−)-(S or R)-ethanesulfonic acid [4-(7-fluoro-1-methyl-2-oxo-1,2,3,4-tetrahydro-quinolin-6-yl)-5,6,7,8-tetrahydro-isoquinolin-8-yl]-amide (example 31), MS: 418.3 (M+H)$^+$ and (+)-(R or S)-ethanesulfonic acid [4-(7-fluoro-1-methyl-2-oxo-1,2,3,4-tetrahydro-quinolin-6-yl)-5,6,7,8-tetrahydro-isoquinolin-8-yl]-amide (example 32). MS: 418.3 (M+H)$^+$.

Example 33

(rac)-N-[4-(8-Chloro-1-methyl-2-oxo-1,2,3,4-tetrahydro-quinolin-6-yl)-5,6,7,8-tetrahydro-isoquinolin-8-yl]-propionamide

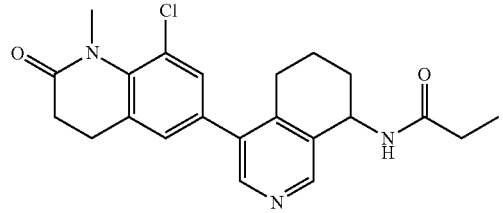 [SMILES: CCC(=O)NC1CCCc2c(-c3cc(Cl)c4c(c3)CCC(=O)N4C)cncc21]

In analogy to the procedure described for the preparation of example 28, 8-chloro-1-methyl-6-(4,4,5,5-tetramethyl-[1,3,2]dioxaborolan-2-yl)-3,4-dihydro-1H-quinolin-2-one (intermediate A-8) and (rac)-N-(4-bromo-5,6,7,8-tetrahydro-isoquinolin-8-yl)-propionamide (intermediate B-1) were used to give the title compound as a white solid in 63% yield. MS: 398.3 (M+H)$^+$.

Example 34

(rac)-Ethanesulfonic acid [4-(7-chloro-1-methyl-2-oxo-1,2,3,4-tetrahydro-quinolin-6-yl)-5,6,7,8-tetrahydro-isoquinolin-8-yl]-amide

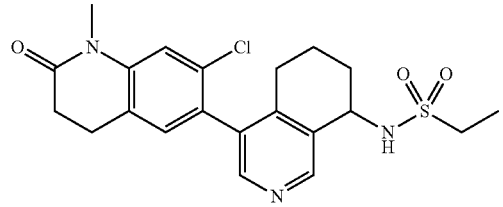 [SMILES: CCS(=O)(=O)NC1CCCc2c(-c3cc4c(cc3Cl)N(C)C(=O)CC4)cncc21]

In analogy to the procedure described for the preparation of example 28, 7-chloro-1-methyl-6-(4,4,5,5-tetramethyl-[1,3,2]dioxaborolan-2-yl)-3,4-dihydro-1H-quinolin-2-one (intermediate A-10) and (rac)-ethanesulfonic acid (4-bromo-5,6,7,8-tetrahydro-isoquinolin-8-yl)-amide (intermediate B-4) were used to give the title compound as a white solid in 40% yield. MS: 434.2 (M+H)$^+$.

Example 35

N—[(R or S)-4-(7-Chloro-1-methyl-2-oxo-1,2,3,4-tetrahydro-quinolin-6-yl)-5,6,7,8-tetrahydro-isoquinolin-8-yl]-propionamide

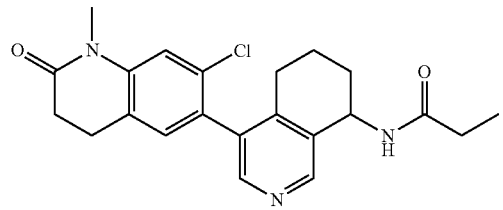 [SMILES: CCC(=O)NC1CCCc2c(-c3cc4c(cc3Cl)N(C)C(=O)CC4)cncc21]

In analogy to the procedure described for the preparation of example 28, 7-chloro-1-methyl-6-(4,4,5,5-tetramethyl-[1,3,2]dioxaborolan-2-yl)-3,4-dihydro-1H-quinolin-2-one (intermediate A-10) and (+)-N—((R or S)-4-bromo-5,6,7,8-tetrahydro-isoquinolin-8-yl)-propionamide (intermediate B-2a) were used to give the title compound as a white solid in 30% yield. MS: 398.1 (M+H)$^+$.

Example 36

(rac)-Ethanesulfonic acid [4-(8-fluoro-1-methyl-2-oxo-1,2,3,4-tetrahydro-quinolin-6-yl)-5,6,7,8-tetrahydro-isoquinolin-8-yl]-amide

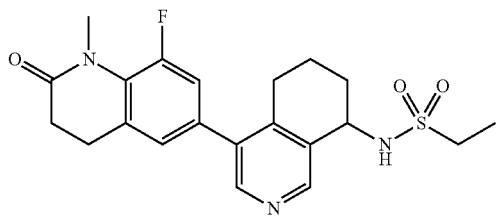 [SMILES: CCS(=O)(=O)NC1CCCc2c(-c3cc(F)c4c(c3)CCC(=O)N4C)cncc21]

In analogy to the procedure described for the preparation of example 28, 8-fluoro-1-methyl-6-(4,4,5,5-tetramethyl-[1,3,2]dioxaborolan-2-yl)-3,4-dihydro-1H-quinolin-2-one (intermediate A-7) and (rac)-ethanesulfonic acid (4-bromo-5,6,7,8-tetrahydro-isoquinolin-8-yl)-amide (intermediate B-4) were used to give the title compound (10.3 mg, 25%) as a white solid. MS: 418.2 (M+H)$^+$.

Example 37

(rac)-Ethanesulfonic acid [4-(8-chloro-1-methyl-2-oxo-1,2,3,4-tetrahydro-quinolin-6-yl)-5,6,7,8-tetrahydro-isoquinolin-8-yl]-amide

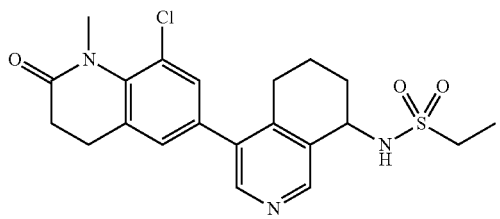

In analogy to the procedure described for the preparation of example 28, 8-chloro-1-methyl-6-(4,4,5,5-tetramethyl-[1,3,2]dioxaborolan-2-yl)-3,4-dihydro-1H-quinolin-2-one (intermediate A-8) and (rac)-ethanesulfonic acid (4-bromo-5,6,7,8-tetrahydro-isoquinolin-8-yl)-amide (intermediate B-4) were used to give the title compound (47.2 mg, 35%) as a white solid. MS: 434.2 (M+H)$^+$.

Example 38 and Example 39

(+)-Ethanesulfonic acid [(R or S)-4-(8-chloro-1-methyl-2-oxo-1,2,3,4-tetrahydro-quinolin-6-yl)-5,6,7,8-tetrahydro-isoquinolin-8-yl]-amide and (−)-Ethanesulfonic acid [(S or R)-4-(8-chloro-1-methyl-2-oxo-1,2,3,4-tetrahydro-quinolin-6-yl)-5,6,7,8-tetrahydro-isoquinolin-8-yl]-amide Example 38

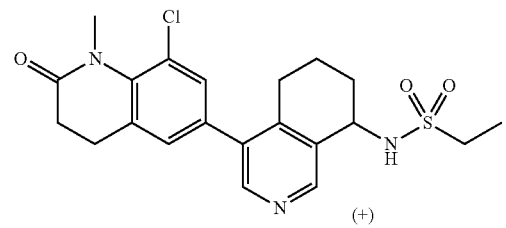

(+)

Example 39

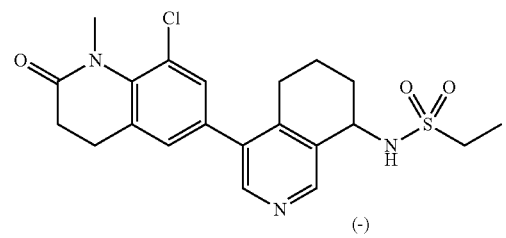

(−)

The title compounds were prepared by chiral separation of (rac)-ethanesulfonic acid [4-(8-chloro-1-methyl-2-oxo-1,2,3,4-tetrahydro-quinolin-6-yl)-5,6,7,8-tetrahydro-isoquinolin-8-yl]-amide (example 37) on a Chiralpak AD column (40% 2-propanol in n-heptane) to give (+)-ethanesulfonic acid [(R or S)-4-(8-chloro-1-methyl-2-oxo-1,2,3,4-tetrahydro-quinolin-6-yl)-5,6,7,8-tetrahydro-isoquinolin-8-yl]-amide (example 38) as off-white powder, MS: 434.1 (M+H$^+$) and (−)-ethanesulfonic acid [(S or R)-4-(8-chloro-1-methyl-2-oxo-1,2,3,4-tetrahydro-quinolin-6-yl)-5,6,7,8-tetrahydro-isoquinolin-8-yl]-amide (example 39) as off-white powder. MS: 434.1 (M+H)$^+$.

Example 40 and Example 41

(−)-N—[(S or R)-4-(8-Chloro-1-methyl-2-oxo-1,2,3,4-tetrahydro-quinolin-6-yl)-5,6,7,8-tetrahydro-isoquinolin-8-yl]-propionamide and (+)-N—[(R or S)-4-(8-Chloro-1-methyl-2-oxo-1,2,3,4-tetrahydro-quinolin-6-yl)-5,6,7,8-tetrahydro-isoquinolin-8-yl]-propionamide Example 40

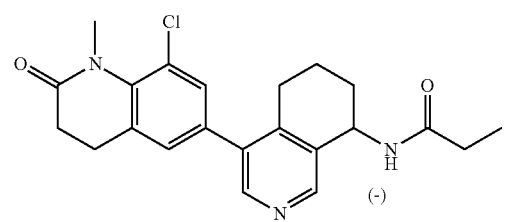

(−)

Example 41

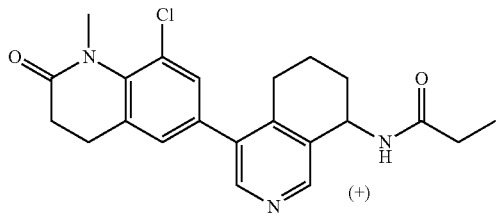

(+)

The title compounds were prepared by chiral separation of (rac)-N-[4-(8-chloro-1-methyl-2-oxo-1,2,3,4-tetrahydro-quinolin-6-yl)-5,6,7,8-tetrahydro-isoquinolin-8-yl]-propionamide (example 33) on a Chiralpak AD column (40% 2-propanol in n-heptane) to give (−)—N—[(S or R)-4-(8-chloro-1-methyl-2-oxo-1,2,3,4-tetrahydro-quinolin-6-yl)-5,6,7,8-tetrahydro-isoquinolin-8-yl]-propionamide (example 40) as off-white powder, MS: 398.1 (M+H$^+$) and (+)—N—[(R or S)-4-(8-chloro-1-methyl-2-oxo-1,2,3,4-tetrahydro-quinolin-6-yl)-5,6,7,8-tetrahydro-isoquinolin-8-yl]-propionamide (example 41) as off-white powder. MS: 398.1 (M+H)$^+$.

Example 42

(+)-N-[(7S,8R or 7R,8S)-7-Methyl-4-(1-methyl-2-oxo-1,2,3,4-tetrahydro-quinolin-6-yl)-5,6,7,8-tetrahydro-isoquinolin-8-yl]-propionamide

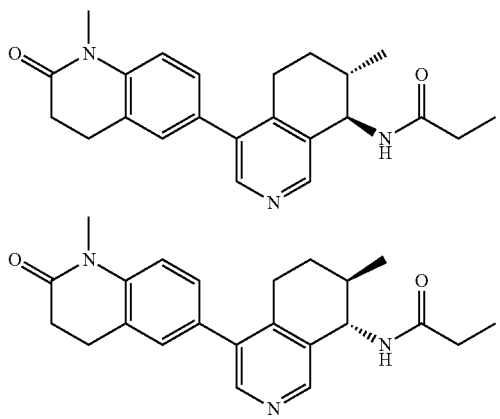

or

A mixture of (+)-N-((7S,8R or 7R,8S)-4-bromo-7-methyl-5,6,7,8-tetrahydro-isoquinolin-8-yl)-propionamide (50 mg, 0.168 mmol) (intermediate B-6c) and 1-methyl-6-(4,4,5,5-tetramethyl-[1,3,2]-dioxaborolan-2-yl)-3,4-dihydro-1H-quinolin-2-one (53 mg, 0.185 mmol) (intermediate A-1) in DMF (1.5 mL) was purged with argon for 1 min before bis(triphenylphosphine)palladium (II)chloride (12 mg, 0.017 mmol) and 2 N aq. Na$_2$CO$_3$ solution (0.168 mL, 0.336 mmol) were added. The resulting reaction mixture was purged with argon for 2 min and then heated at 100° C. for 30 min in a microwave. After cooling to room temperature, the reaction mixture was diluted with EtOAc (5 mL), filtered through Dicalite and washed with EtOAc (2×20 mL). The resulting filtrate was washed with brine, dried over anhy. Na$_2$SO$_4$, filtered and evaporated to dryness. The crude product was then purified by Prep-HPLC to give title compound (15 mg, 23.8%) as a white foam. MS: 378.1 (M+H)$^+$.

Example 43

(−)-N-[(7S,8S or 7R,8R)-4-(7-Fluoro-1-methyl-2-oxo-1,2,3,4-tetrahydro-quinolin-6-yl)-7-methyl-5,6,7,8-tetrahydro-isoquinolin-8-yl]-propionamide

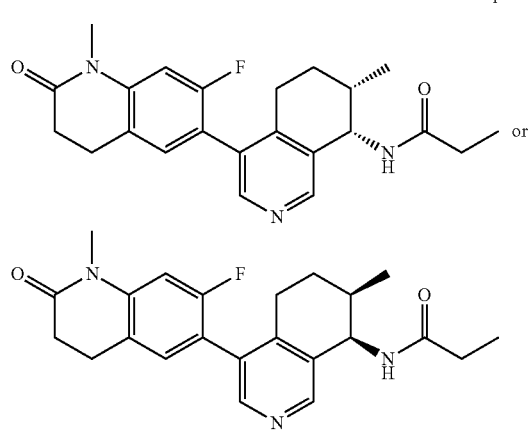

or

In analogy to the procedure described for the preparation of example 42, (−)-N-((7S,8S or 7R,8R)-4-bromo-7-methyl-5,6,7,8-tetrahydro-isoquinolin-8-yl)-propionamide (intermediate B-6b) and 7-fluoro-1-methyl-6-(4,4,5,5-tetramethyl-[1,3,2]dioxaborolan-2-yl)-3,4-dihydro-1H-quinolin-2-one (intermediate A-9) gave the title compound as a white foam in 25% yield. MS: 396.1 (M+H)$^+$.

Example 44

(−)-N-[(7R,8S or 7S,8R)-4-(7-Fluoro-1-methyl-2-oxo-1,2,3,4-tetrahydro-quinolin-6-yl)-7-methyl-5,6,7,8-tetrahydro-isoquinolin-8-yl]-propionamide

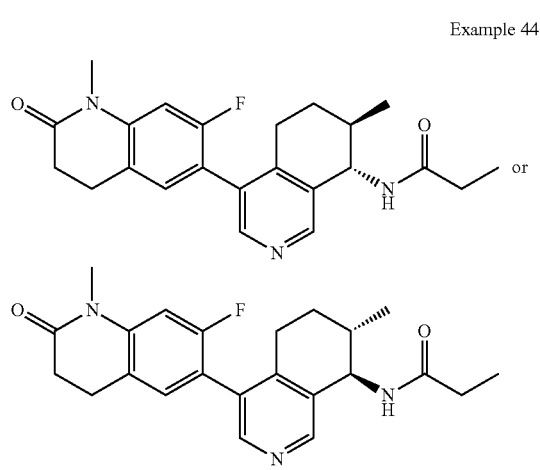

or

In analogy to the procedure described for the preparation of example 42, (−)-N-((7R,8S or 7S,8R)-4-bromo-7-methyl-5,6,7,8-tetrahydro-isoquinolin-8-yl)-propionamide (intermediate B-6a) and 7-fluoro-1-methyl-6-(4,4,5,5-tetramethyl-[1,3,2]dioxaborolan-2-yl)-3,4-dihydro-1H-quinolin-2-one (intermediate A-9) gave the title compound as a white foam in 30% yield. MS: 396.1 (M+H)+.

Example 45

(+)-N-[(7S,8R or 7R,8S)-4-(7-Fluoro-1-methyl-2-oxo-1,2,3,4-tetrahydro-quinolin-6-yl)-7-methyl-5,6,7,8-tetrahydro-isoquinolin-8-yl]-propionamide

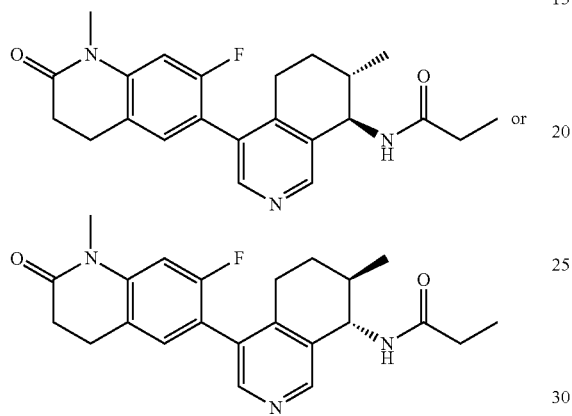

Example 45

In analogy to the procedure described for the preparation of example 42, (+)-N-((7S,8R or 7R,8S)-4-bromo-7-methyl-5,6,7,8-tetrahydro-isoquinolin-8-yl)-propionamide (intermediate B-6c) and 7-fluoro-1-methyl-6-(4,4,5,5-tetramethyl-[1,3,2]dioxaborolan-2-yl)-3,4-dihydro-1H-quinolin-2-one (intermediate A-9) gave the title compound as a white foam in 28% yield. MS: 396.1 (M+H)+.

Example 46

(−)-N-[(7S,8S or 7R,8R)-7-Methyl-4-(1-methyl-2-oxo-1,2,3,4-tetrahydro-quinolin-6-yl)-5,6,7,8-tetrahydro-isoquinolin-8-yl]-propionamide

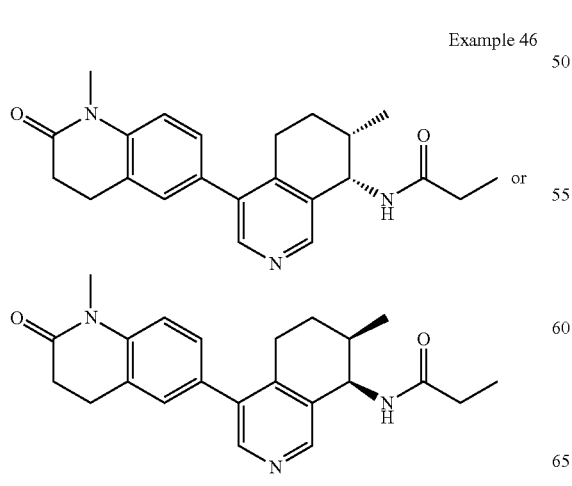

Example 46

In analogy to the procedure described for the preparation of example 42, (−)-N-((7S,8S or 7R,8R)-4-bromo-7-methyl-5,6,7,8-tetrahydro-isoquinolin-8-yl)-propionamide (intermediate B-6b) and 1-methyl-6-(4,4,5,5-tetramethyl-[1,3,2]dioxaborolan-2-yl)-3,4-dihydro-1H-quinolin-2-one (intermediate A-1) gave the title compound as a white foam in 24% yield. MS: 378.1 (M+H)+.

Example 47

(−)-N-[(7R,8S or 7S,8R)-7-Methyl-4-(1-methyl-2-oxo-1,2,3,4-tetrahydro-quinolin-6-yl)-5,6,7,8-tetrahydro-isoquinolin-8-yl]-propionamide

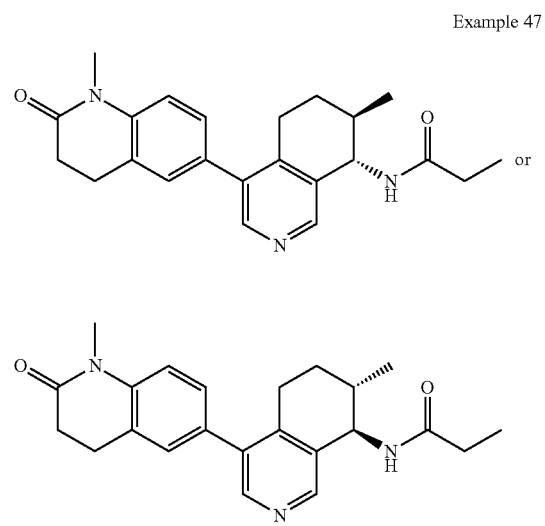

Example 47

In analogy to the procedure described for the preparation of example 42, (−)-N-((7R,8S or 7S,8R)-4-bromo-7-methyl-5,6,7,8-tetrahydro-isoquinolin-8-yl)-propionamide (intermediate B-6a) and 1-methyl-6-(4,4,5,5-tetramethyl-[1,3,2]dioxaborolan-2-yl)-3,4-dihydro-1H-quinolin-2-one (intermediate A-1) gave the title compound as a white foam in 24% yield. MS: 378.1 (M+H)+.

Example 48

(+)-N-[(7R,8R or 7S,8S)-4-(7-Fluoro-1-methyl-2-oxo-1,2,3,4-tetrahydro-quinolin-6-yl)-7-methyl-5,6,7,8-tetrahydro-isoquinolin-8-yl]-propionamide

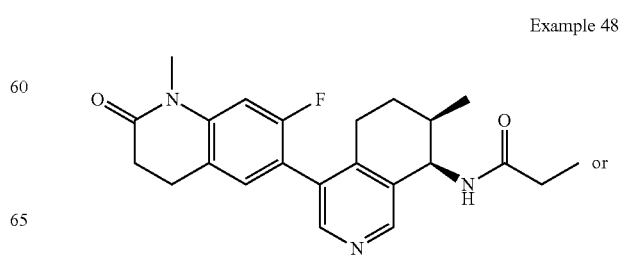

Example 48

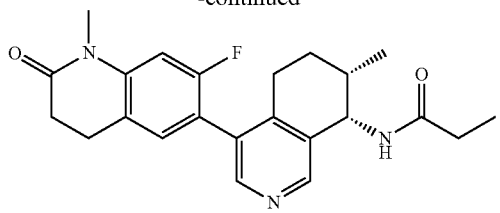

In analogy to the procedure described for the preparation of example 42, (+)-N-((7R,8R or 7S,8S)-4-bromo-7-methyl-5,6,7,8-tetrahydro-isoquinolin-8-yl)-propionamide (intermediate B-6d) and 7-fluoro-1-methyl-6-(4,4,5,5-tetramethyl-[1,3,2]dioxaborolan-2-yl)-3,4-dihydro-1H-quinolin-2-one (intermediate A-9) gave the title compound as a white foam in 28% yield. MS: 396.1 (M+H)$^+$.

Example 49

(+)-N-[(7R,8R or 7S,8S)-7-Methyl-4-(1-methyl-2-oxo-1,2,3,4-tetrahydro-quinolin-6-yl)-5,6,7,8-tetrahydro-isoquinolin-8-yl]-propionamide Example 49

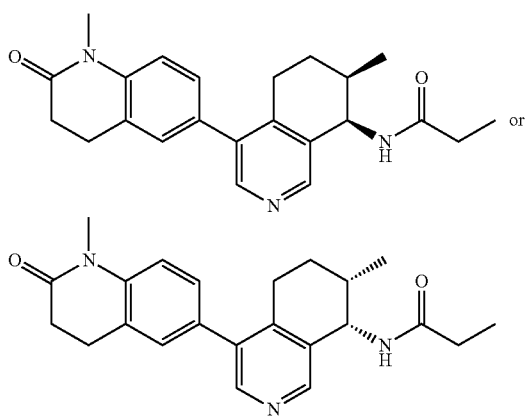

In analogy to the procedure described for the preparation of example 42, (+)-N-((7R,8R or 7S,8S)-4-bromo-7-methyl-5,6,7,8-tetrahydro-isoquinolin-8-yl)-propionamide (intermediate B-6d) and 1-methyl-6-(4,4,5,5-tetramethyl-[1,3,2]dioxaborolan-2-yl)-3,4-dihydro-1H-quinolin-2-one (intermediate A-1) gave the title compound as a white foam in 24% yield. MS: 378.1 (M+H)$^+$.

Example 50-53

(all rac)-N-[7-Fluoro-4-(1-methyl-2-oxo-1,2,3,4-tetrahydro-quinolin-6-yl)-5,6,7,8-tetrahydro-isoquinolin-8-yl]-propionamide

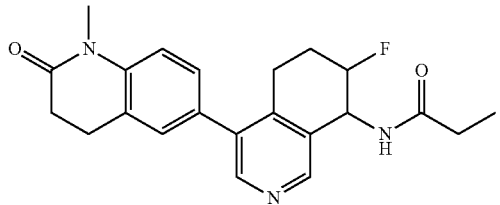 [SMILES: CCC(=O)NC1c2cncc(-c3ccc4c(c3)CCC(=O)N4C)c2CCC1F]

In analogy to the procedure described for the preparation of example 42, (all rac)-N-(4-bromo-7-fluoro-5,6,7,8-tetrahydro-isoquinolin-8-yl)-propionamide (intermediate B-7) and 1-methyl-6-(4,4,5,5-tetramethyl-[1,3,2]dioxaborolan-2-yl)-3,4-dihydro-1H-quinolin-2-one (intermediate A-1) gave the title compound as a light yellow foam in 40% yield. MS: 382.1 (M+H)$^+$.

Example 50

(−)-N-[(7R,8R or 7S,8S)-7-Fluoro-4-(1-methyl-2-oxo-1,2,3,4-tetrahydro-quinolin-6-yl)-5,6,7,8-tetrahydro-isoquinolin-8-yl]-propionamide Example 50

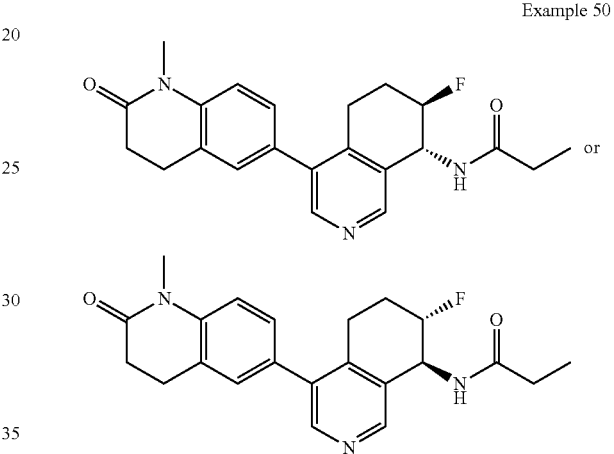

Example 51

(−)-N-[(7S,8R or 7R,8S)-7-Fluoro-4-(1-methyl-2-oxo-1,2,3,4-tetrahydro-quinolin-6-yl)-5,6,7,8-tetrahydro-isoquinolin-8-yl]-propionamide Example 51

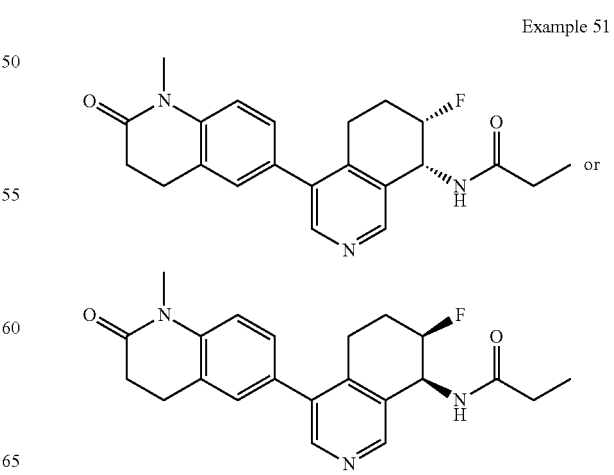

Example 52

(+)-N-[(7S,8S or 7R,8R)-7-Fluoro-4-(1-methyl-2-oxo-1,2,3,4-tetrahydro-quinolin-6-yl)-5,6,7,8-tetrahydro-isoquinolin-8-yl]-propionamide

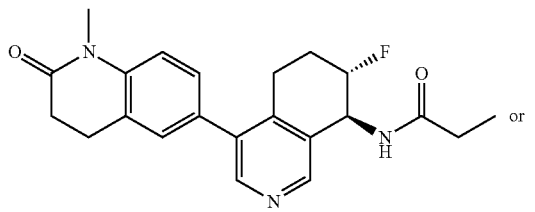

Example 52

Example 53

(+)-N-[(7R,8S or 7S,8R)-7-Fluoro-4-(1-methyl-2-oxo-1,2,3,4-tetrahydro-quinolin-6-yl)-5,6,7,8-tetrahydro-isoquinolin-8-yl]-propionamide

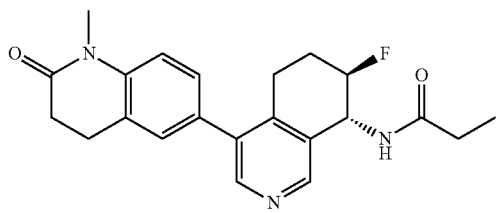

Example 53

The title compounds were prepared by chiral separation of (all rac)-N-[7-fluoro-4-(1-methyl-2-oxo-1,2,3,4-tetrahydro-quinolin-6-yl)-5,6,7,8-tetrahydro-isoquinolin-8-yl]-propionamide (60 mg) on a Chiralpak IA column (50% ethanol in n-hexane) to give (−)-N-[(7R,8R or 7S,8S)-7-fluoro-4-(1-methyl-2-oxo-1,2,3,4-tetrahydro-quinolin-6-yl)-5,6,7,8-tetrahydro-isoquinolin-8-yl]-propionamide (example 50) as light yellow oil, MS: 382.1 (M+H)⁺ and (−)-N-[(7S,8R or 7R,8S)-7-fluoro-4-(1-methyl-2-oxo-1,2,3,4-tetrahydro-quinolin-6-yl)-5,6,7,8-tetrahydro-isoquinolin-8-yl]-propionamide (example 51) as off-white solid, MS: 382.1 (M+H)⁺ and (+)-N-[(7S,8S or 7R,8R)-7-fluoro-4-(1-methyl-2-oxo-1,2,3,4-tetrahydro-quinolin-6-yl)-5,6,7,8-tetrahydro-isoquinolin-8-yl]-propionamide (example 52) as light yellow oil, MS: 382.1 (M+H)⁺ and of (+)-N-[(7R,8S or 7S,8R)-7-fluoro-4-(1-methyl-2-oxo-1,2,3,4-tetrahydro-quinolin-6-yl)-5,6,7,8-tetrahydro-isoquinolin-8-yl]-propionamide (example 53) as off-white solid, MS: 382.1 (M+H)⁺.

Example 54-57

(all rac)-N-[7-Fluoro-4-(7-fluoro-1-methyl-2-oxo-1,2,3,4-tetrahydro-quinolin-6-yl)-5,6,7,8-tetrahydro-isoquinolin-8-yl]-propionamide

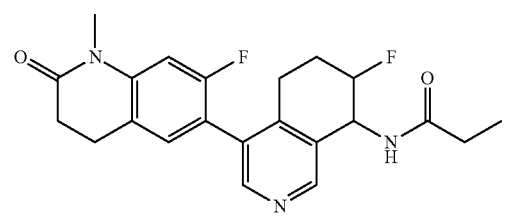 [SMILES: CCC(=O)NC1c2cncc(-c3cc4c(cc3F)N(C)C(=O)CC4)c2CCC1F]

In analogy to the procedure described for the preparation of example 42, (rac)-N-(4-bromo-7-fluoro-5,6,7,8-tetrahydro-isoquinolin-8-yl)-propionamide (intermediate B-7) and 7-fluoro-1-methyl-6-(4,4,5,5-tetramethyl-[1,3,2]dioxaborolan-2-yl)-3,4-dihydro-1H-quinolin-2-one (intermediate A-9) gave the title compound as a light yellow foam in 46% yield. MS: 400.1 (M+H)⁺.

Example 54

(+)-N-[(7S,8S or 7R,8R)-7-Fluoro-4-(7-fluoro-1-methyl-2-oxo-1,2,3,4-tetrahydro-quinolin-6-yl)-5,6,7,8-tetrahydro-isoquinolin-8-yl]-propionamide

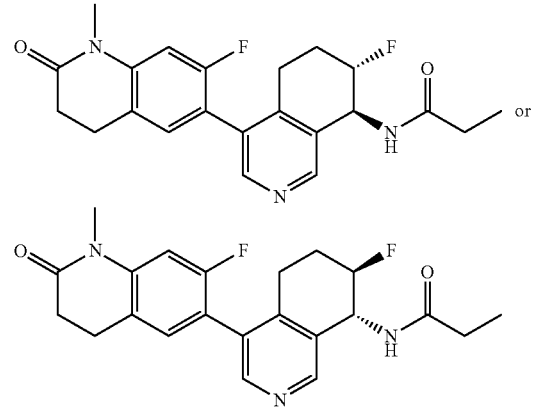

Example 54

Example 55

(+)-N-[(7R,8S or 7S,8R)-7-Fluoro-4-(7-fluoro-1-methyl-2-oxo-1,2,3,4-tetrahydro-quinolin-6-yl)-5,6,7,8-tetrahydro-isoquinolin-8-yl]-propionamide

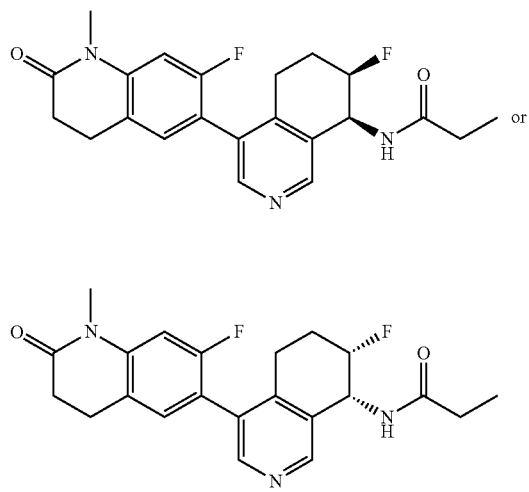

Example 56

(−)-N-[(7R,8R or 7S,8S)-7-Fluoro-4-(7-fluoro-1-methyl-2-oxo-1,2,3,4-tetrahydro-quinolin-6-yl)-5,6,7,8-tetrahydro-isoquinolin-8-yl]-propionamide

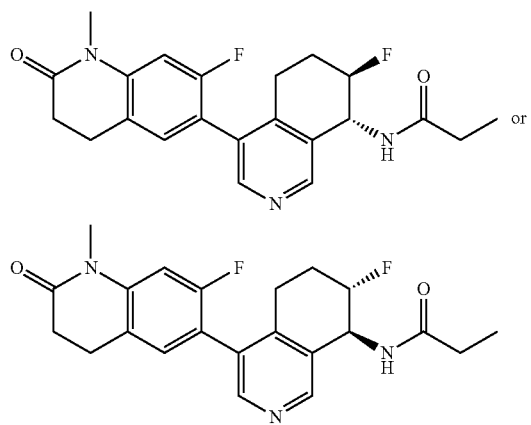

Example 57

(−)-N-[(7S,8R or 7R,8S)-7-Fluoro-4-(7-fluoro-1-methyl-2-oxo-1,2,3,4-tetrahydro-quinolin-6-yl)-5,6,7,8-tetrahydro-isoquinolin-8-yl]-propionamide

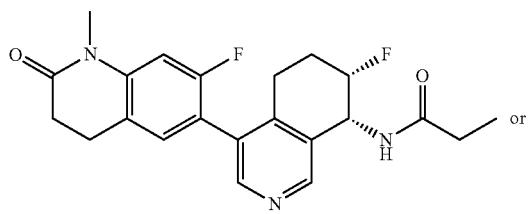

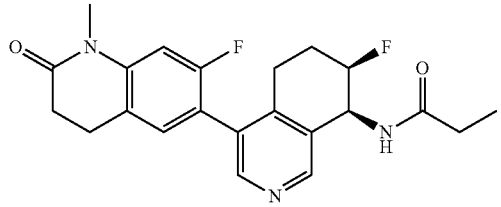

The title compounds were prepared by chiral separation of (all rac)-N-[7-fluoro-4-(7-fluoro-1-methyl-2-oxo-1,2,3,4-tetrahydro-quinolin-6-yl)-5,6,7,8-tetrahydro-isoquinolin-8-yl]-propionamide (120 mg) on a Chiralpak IA column (50% ethanol in n-hexane) to give (+)-N-[(7S,8S or 7R,8R)-7-fluoro-4-(7-fluoro-1-methyl-2-oxo-1,2,3,4-tetrahydro-quinolin-6-yl)-5,6,7,8-tetrahydro-isoquinolin-8-yl]-propionamide (example 54) as light yellow oil, MS: 400.1 (M+H$^+$) and (+)-N-[(7R,8S or 7S,8R)-7-fluoro-4-(7-fluoro-1-methyl-2-oxo-1,2,3,4-tetrahydro-quinolin-6-yl)-5,6,7,8-tetrahydro-isoquinolin-8-yl]-propionamide (example 55) as off-white solid, MS: 400.1 (M+H)$^+$ and (−)-N-[(7R,8R or 7S,8S)-7-fluoro-4-(7-fluoro-1-methyl-2-oxo-1,2,3,4-tetrahydro-quinolin-6-yl)-5,6,7,8-tetrahydro-isoquinolin-8-yl]-propionamide (example 56) as light yellow oil, MS: 400.1 (M+H)$^+$ and (−)-N-[(7S,8R or 7R,8S)-7-fluoro-4-(7-fluoro-1-methyl-2-oxo-1,2,3,4-tetrahydro-quinolin-6-yl)-5,6,7,8-tetrahydro-isoquinolin-8-yl]-propionamide (example 57) as off-white solid, MS: 400.1 (M+H)$^+$.

Example 58

(rac)-N-(4-(8-Chloro-1-methyl-2-oxo-1,2,3,4-tetrahydroquinolin-6-yl)-6,7-dihydro-5H-cyclopenta[c]pyridin-7-yl)propionamide

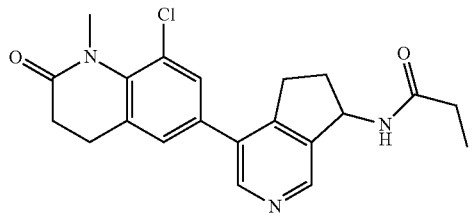 [SMILES: CCC(=O)NC1CCc2c(-c3cc(Cl)c4c(c3)CCC(=O)N4C)cncc21]

In analogy to the procedure described for the preparation of example 28, 8-chloro-1-methyl-6-(4,4,5,5-tetramethyl-[1,3,2]dioxaborolan-2-yl)-3,4-dihydro-1H-quinolin-2-one (intermediate A-8) and (rac)-N-(4-bromo-6,7-dihydro-5H-cyclopenta[c]pyridin-7-yl)propionamide (intermediate A-3) were used to give the title compound as a white powder in 65% yield. MS: 384.3 (M+H)+.

Example 59 and Example 60

(−)-(S or R)—N-(4-(8-Chloro-1-methyl-2-oxo-1,2,3,4-tetrahydroquinolin-6-yl)-6,7-dihydro-5H-cyclopenta[c]pyridin-7-yl)propionamide and (+)-(R or S)—N-(4-(8-Chloro-1-methyl-2-oxo-1,2,3,4-tetrahydroquinolin-6-yl)-6,7-dihydro-5H-cyclopenta[c]pyridin-7-yl)propionamide Example 59

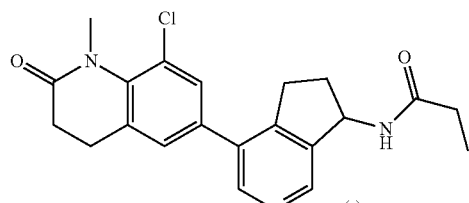

(−)

Example 60

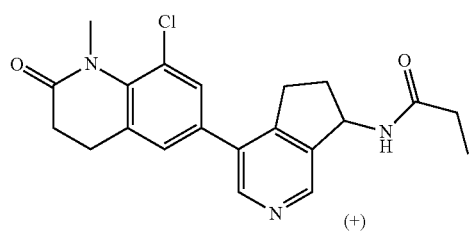

(+)

The title compounds were prepared by chiral separation of (rac)-N-(4-(8-chloro-1-methyl-2-oxo-1,2,3,4-tetrahydroquinolin-6-yl)-6,7-dihydro-5H-cyclopenta[c]pyridin-7-yl)propionamide (example 58) on a Chiralpak AD column (40% 2-propanol in n-heptane) to give 35% (−)-(S or R)—N-(4-(8-chloro-1-methyl-2-oxo-1,2,3,4-tetrahydroquinolin-6-yl)-6,7-dihydro-5H-cyclopenta[c]pyridin-7-yl)propionamide (example 59) as white powder, MS: 384.3 (M+H+) and 36% (+)-(R or S)—N-(4-(8-chloro-1-methyl-2-oxo-1,2,3,4-tetrahydroquinolin-6-yl)-6,7-dihydro-5H-cyclopenta[c]pyridin-7-yl)propionamide (example 60) as white powder. MS: 384.3 (M+H)+.

Example 61

(R)-6-(8-Amino-5,6,7,8-tetrahydroisoquinolin-4-yl)-1-methyl-3,4-dihydroquinolin-2(1H)-one

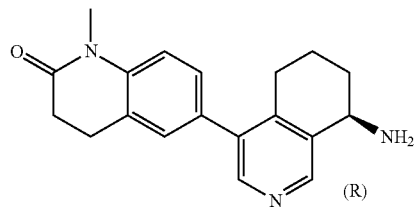

In analogy to the procedure described for the preparation of intermediate A-2 [E], Suzuki reaction of (+)-(R)-4-bromo-5,6,7,8-tetrahydroisoquinolin-8-amine (intermediate B-3b) with 1-methyl-6-(4,4,5,5-tetramethyl-[1,3,2]dioxaborolan-2-yl)-3,4-dihydro-1H-quinolin-2-one (intermediate A-1) gave the title compound as light yellow amorphous solid. MS: 308.2 (M+H)+.

Example 62

3-Chloro-pyridine-2-carboxylic acid [(R)-4-(1-methyl-2-oxo-1,2,3,4-tetrahydro-quinolin-6-yl)-5,6,7,8-tetrahydro-isoquinolin-8-yl]-amide

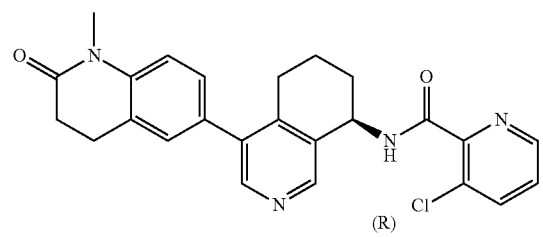

In analogy to the procedure described for the preparation of example 13, coupling of (R)-6-(8-amino-5,6,7,8-tetrahydroisoquinolin-4-yl)-1-methyl-3,4-dihydroquinolin-2(1H)-one (example 61) with 3-chloro-pyridine-2-carboxylic acid gave the title compound as colorless solid. MS: 447.4 (M+H+).

Example 63

N—[(R)-4-(1-Methyl-2-oxo-1,2,3,4-tetrahydro-quinolin-6-yl)-5,6,7,8-tetrahydro-isoquinolin-8-yl]-acetamide

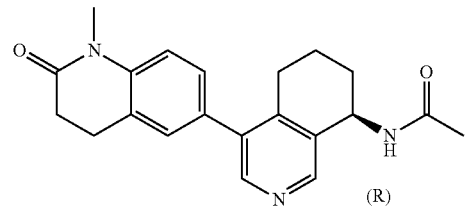

In analogy to the procedure described for the preparation of intermediate B-1, reaction of (R)-6-(8-amino-5,6,7,8-tetrahydroisoquinolin-4-yl)-1-methyl-3,4-dihydroquinolin-2(1H)-one (example 61) with acetyl chloride gave the title compound as colorless amorphous solid. MS: 350.5 (M+H+).

Example 64

Cyclopropanecarboxylic acid [(R)-4-(1-methyl-2-oxo-1,2,3,4-tetrahydro-quinolin-6-yl)-5,6,7,8-tetrahydro-isoquinolin-8-yl]-amide

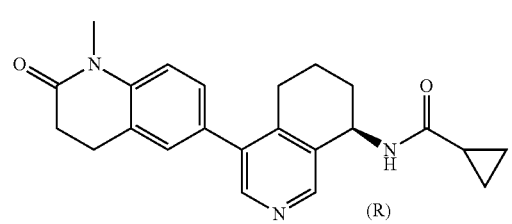

In analogy to the procedure described for the preparation of intermediate B-1, reaction of (R)-6-(8-amino-5,6,7,8-tetrahydroisoquinolin-4-yl)-1-methyl-3,4-dihydroquinolin-2 (1H)-one (example 61) with cyclopropanecarbonyl chloride gave the title compound as a light yellow solid. MS: 376.5 (M+H⁺).

Example 65

N—[(R)-4-(1-Methyl-2-oxo-1,2,3,4-tetrahydro-quinolin-6-yl)-5,6,7,8-tetrahydro-isoquinolin-8-yl]-methanesulfonamide

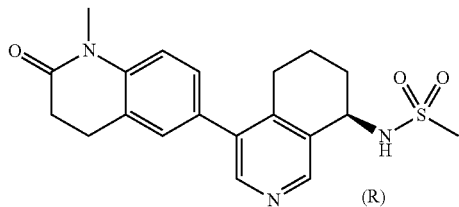

In analogy to the procedure described for the preparation of example 4, reaction of (R)-6-(8-amino-5,6,7,8-tetrahydroisoquinolin-4-yl)-1-methyl-3,4-dihydroquinolin-2(1H)-one (example 61) with methanesulfonyl chloride gave the title compound as a colorless solid. MS: 386.5 (M+H⁺).

Example 66

Cyclopropanesulfonic acid [(R)-4-(1-methyl-2-oxo-1,2,3,4-tetrahydro-quinolin-6-yl)-5,6,7,8-tetrahydro-isoquinolin-8-yl]-amide

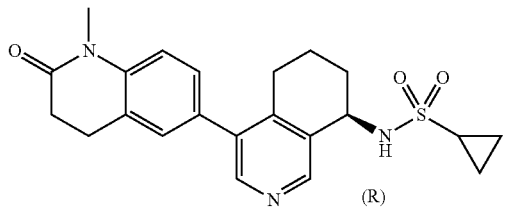

In analogy to the procedure described for the preparation of example 4, reaction of (R)-6-(8-amino-5,6,7,8-tetrahydroisoquinolin-4-yl)-1-methyl-3,4-dihydroquinolin-2(1H)-one (example 61) with cyclopropanesulfonyl chloride gave the title compound as colorless solid. MS: 412.5 (M+H⁺).

Example 67

(rac)-6-(8-Hydroxy-5,6,7,8-tetrahydro-isoquinolin-4-yl)-1-methyl-3,4-dihydroquinolin-2(1H)-one

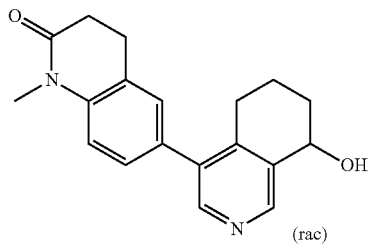 [SMILES: CN1C(=O)CCc2cc(-c3cncc4c3CCCC4O)ccc21]

[A] (rac)-4-Bromo-5,6,7,8-tetrahydro-isoquinolin-8-ol

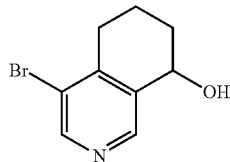

A suspension of 4-bromo-6,7-dihydroisoquinolin-8(5H)-one (intermediate A-2 [C]) (2.135 g, 9.44 mmol) in MeOH (18.9 mL) was cooled to 0° C. and treated with NaBH₄ (357 mg, 9.44 mmol) in 5 portions over 30 min. The reaction was stirred for ¾ h at 0° C., then AcOH was added dropwise until a pH ~5-6 was obtained and the reaction mixture was evaporated. The residue was diluted with water and poured into aq. sat. NaHCO₃-solution, then extracted with EtOAc (3×). The organic layers are washed once with aq. sat. NaHCO₃ and aq. 10% NaCl solution, dried over Na₂SO₄ and concentrated in vacuo. The residue was precipitated with CH₂Cl₂/n-pentane to afford the title compound (1.98 g, 92%) as dark brown viscous oil. MS: 227 (M⁺, 1Br).

[B] (rac)-6-(8-Hydroxy-5,6,7,8-tetrahydro-isoquinolin-4-yl)-1-methyl-3,4-dihydroquinolin-2(1H)-one

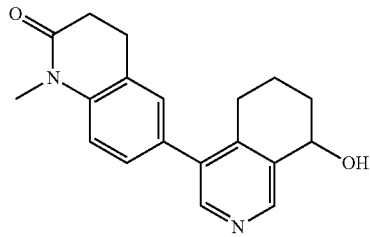 [SMILES: CN1C(=O)CCc2cc(-c3cncc4c3CCCC4O)ccc21]

In analogy to the procedure described for the preparation of intermediate A-2 [E], Suzuki reaction of (rac)-4-bromo-5,6,7,8-tetrahydro-isoquinolin-8-ol with 1-methyl-6-(4,4,5,5-tetramethyl-[1,3,2]dioxaborolan-2-yl)-3,4-dihydro-1H-quinolin-2-one (intermediate A-1) gave the title compound as light red powder. MS: 309.5 (M+H⁺).

Example 68 and Example 69

(S or R)-6-(8-Hydroxy-5,6,7,8-tetrahydro-isoquinolin-4-yl)-1-methyl-3,4-dihydroquinolin-2(1H)-one and (R or S)-6-(8-Hydroxy-5,6,7,8-tetrahydro-isoquinolin-4-yl)-1-methyl-3,4-dihydroquinolin-2(1H)-one Example 68

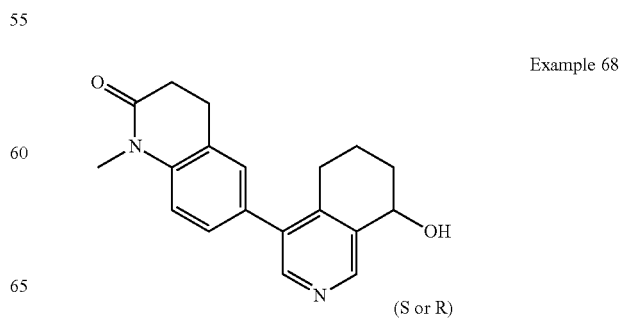

-continued

Example 69

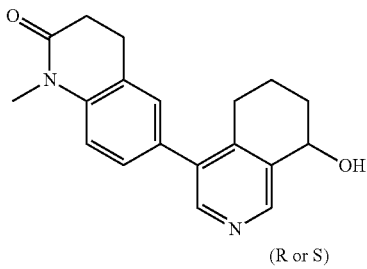

(R or S)

The title compounds were prepared by chiral separation of 6-(rac)-(8-hydroxy-5,6,7,8-tetrahydro-isoquinolin-4-yl)-1-methyl-3,4-dihydroquinolin-2(1H)-one (example 67) on a Chiralpak IA (20 um) column (95% ethanol in n-heptane) to give after precipitation from CH$_2$Cl$_2$ with n-pentane 35% of (S or R)-6-(8-hydroxy-5,6,7,8-tetrahydro-isoquinolin-4-yl)-1-methyl-3,4-dihydroquinolin-2(1H)-one (example 68) as off-white solid, MS: 309.2 (M+H$^+$) and 35% of (R or S)-6-(8-hydroxy-5,6,7,8-tetrahydro-isoquinolin-4-yl)-1-methyl-3,4-dihydroquinolin-2(1H)-one (example 69) as light red solid. MS: 309.2 (M+H$^+$).

Example 70

1-Methyl-6-(8-oxo-5,6,7,8-tetrahydro-isoquinolin-4-yl)-3,4-dihydro-1H-quinolin-2-one

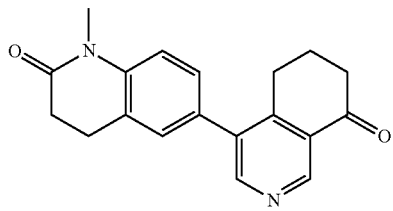 [SMILES: CN1C(=O)CCc2cc(-c3cncc4c3CCCC4=O)ccc21]

In analogy to the procedure described for the preparation of intermediate A-2 [E], the title compound has been obtained by Suzuki reaction of 4-bromo-6,7-dihydroisoquinolin-8 (5H)-one (intermediate A-2 [C]) with 1-methyl-6-(4,4,5,5-tetramethyl-[1,3,2]dioxaborolan-2-yl)-3,4-dihydro-1H-quinolin-2-one (intermediate A-1) as light yellow powder. MS: 307.14 (M+H$^+$).

Example 71

N-[4-(1-Methyl-2-oxo-1,2,3,4-tetrahydro-quinolin-6-yl)-5,6-dihydro-isoquinolin-8-yl]-propionamide

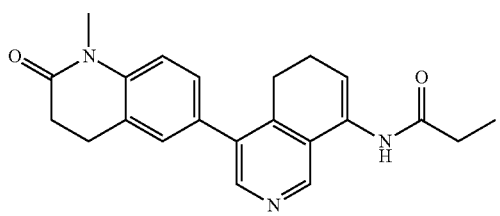 [SMILES: CCC(=O)NC1=CCCc2c1cncc2-c1ccc2c(c1)CCC(=O)N2C]

To a stirred suspension of 1-methyl-6-(8-oxo-5,6,7,8-tetrahydro-isoquinolin-4-yl)-3,4-dihydro-1H-quinolin-2-one) (919 mg, 3 mmol, example 70) and propionic acid amide (658 mg, 9 mmol) in trifluorotoluene (30 mL) was added trifluoromethane sulfonic acid (585 mg, 3.9 mmol) and the reaction was stirred at 102° C. After 4 h, a solution of trifluoromethane sulfonic acid (158 mg, 1.05 mmol) in trifluorotoluene (5 mL) was added and the reaction mixture stirred for further 8 h. After this time, propionic acid amide (219 mg, 3 mmol) and a solution of trifluoromethane sulfonic acid (158 mg, 1.05 mmol) in trifluorotoluene (5 mL) were added and the stirring continued at 102° C. over night. The reaction mixture was allowed to cool down to room temperature and aq. NaOH 2 M (30 mL) was added. The resulting mixture was extracted with dichloromethane (3×) and the organic phases washed with aq. sat. NaCl solution (2×). The combined organic phases were dried over Na$_2$SO$_4$, filtered and evaporated. Crystallization of the crude product (dichloromethane/ethyl acetate/heptane) afforded the title compound (915 mg, 84% yield) as off-white crystals. MS: 362.2 (M+H$^+$).

Example A

A compound of formula (I) can be used in a manner known per se as the active ingredient for the production of tablets of the following composition:

|  | Per tablet |
|---|---|
| Active ingredient | 200 mg |
| Microcrystalline cellulose | 155 mg |
| Corn starch | 25 mg |
| Talc | 25 mg |
| Hydroxypropylmethylcellulose | 20 mg |
|  | 425 mg |

Example B

A compound of formula (I) can be used in a manner known per se as the active ingredient for the production of capsules of the following composition:

|  | Per capsule |
|---|---|
| Active ingredient | 100.0 mg |
| Corn starch | 20.0 mg |
| Lactose | 95.0 mg |
| Talc | 4.5 mg |
| Magnesium stearate | 0.5 mg |
|  | 220.0 mg |

The invention claimed is:

1. A compound of formula (I):

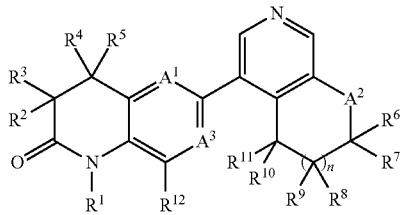

wherein:
R$^1$ is C$_1$-C$_7$-alkyl;
R$^2$ is H;
R$^3$ is H;
R$^4$ is H;
R$^5$ is H;
R$^6$ is H, halogen or C$_1$-C$_7$-alkyl;
R$^7$ is H;
R$^8$ is H;
R$^9$ is H;
R$^{10}$ is H;
R$^{11}$ is H;
R$^{12}$ is H or halogen;
A$^1$ is CR$^{13}$;
A$^2$ is NR$^{14}$ or CR$^{15}$R$^{16}$;
A$^3$ is CR$^{17}$;
R$^{13}$ is H or halogen;
R$^{14}$ is —(CR$^{20}$R$^{21}$)$_q$—(CR$^{22}$R$^{23}$)$_r$—(CR$^{24}$R$^{25}$)$_p$—NR$^{26}$R$^{27}$, wherein the sum of q, r and p is at least 2;
R$^{15}$ is —(CR$^{20}$R$^{21}$)$_q$—(CR$^{22}$R$^{23}$)$_r$—(CR$^{24}$R$^{25}$)$_p$—NR$^{26}$R$^{27}$;
R$^{16}$ is H;
or R$^6$ and R$^{16}$ together with the carbon atoms to which they are attached form a double bond;
R$^{17}$ is H;
R$^{20}$ is H;
R$^{21}$ is H;
R$^{22}$ is H;
R$^{23}$ is H;
R$^{24}$ is H;
R$^{25}$ is H;
R$^{26}$ is H;
R$^{27}$ is H, —S(O)$_2$R$^{31}$, —C(O)R$^{31}$ or —C(O)OR$^{31}$, wherein in case R$^{26}$ is H and R$^{27}$ is H, then the sum of q, r and p is at least 1;
R$^{31}$ is C$_1$-C$_7$-alkyl, chloropyridinyl, hydroxyl-C$_1$-C$_7$-alkyl or C$_3$-C$_8$-cycloalkyl;
n is zero or 1;
p is zero or 1;
q is zero or 1; and
r is zero or 1;
or a pharmaceutically acceptable salt or ester thereof.

2. A compound according to claim 1, wherein R$^6$ is H.

3. A compound according to claim 1, wherein R$^{12}$ is H.

4. A compound according to claim 1, wherein A$^2$ is CR$^{15}$R$^{16}$.

5. A compound according to claim 1, wherein R$^{27}$ is —S(O)$_2$R$^{31}$ or —C(O)R$^{31}$.

6. A compound according to claim 1, wherein R$^{27}$ is —C(O)R$^{31}$.

7. A compound according to claim 1, wherein R$^{31}$ is C$_1$-C$_7$ alkyl.

8. A compound according to claim 1, wherein n is 1.

9. A compound according to claim 1, wherein q, r and p are zero.

10. A compound according to claim 1, selected from the group consisting of
(rac)-N-[4-(1-Methyl-2-oxo-1,2,3,4-tetrahydro-quinolin-6-yl)-5,6,7,8-tetrahydro-isoquinolin-8-yl]-propionamide;
(−)-N-(4-(1-Methyl-2-oxo-1,2,3,4-tetrahydroquinolin-6-yl)-5,6,7,8-tetrahydroisoquinolin-8-yl)propionamide;
(+)-N-(4-(1-Methyl-2-oxo-1,2,3,4-tetrahydroquinolin-6-yl)-5,6,7,8-tetrahydroisoquinolin-8-yl)propionamide;
(R)—N-(4-(1-Methyl-2-oxo-1,2,3,4-tetrahydroquinolin-6-yl)-5,6,7,8-tetrahydroisoquinolin-8-yl)propionamide;
(S)—N-(4-(1-Methyl-2-oxo-1,2,3,4-tetrahydroquinolin-6-yl)-5,6,7,8-tetrahydroisoquinolin-8-yl)propionamide;
(rac)-N-(4-(1-Methyl-2-oxo-1,2,3,4-tetrahydroquinolin-6-yl)-5,6,7,8-tetrahydroisoquinolin-8-yl)ethanesulfonamide;
(−)-N-(4-(1-Methyl-2-oxo-1,2,3,4-tetrahydroquinolin-6-yl)-5,6,7,8-tetrahydroisoquinolin-8-yl)ethanesulfonamide;
(+)-N-(4-(1-Methyl-2-oxo-1,2,3,4-tetrahydroquinolin-6-yl)-5,6,7,8-tetrahydroisoquinolin-8-yl)ethanesulfonamide;
(R)—N-(4-(1-Methyl-2-oxo-1,2, 3,4-tetrahydroquinolin-6-yl)-5,6,7,8-tetrahydroisoquinolin-8-yl)ethanesulfonamide;
(S)—N-(4-(1-Methyl-2-oxo-1,2,3,4-tetrahydroquinolin-6-yl)-5,6,7,8-tetrahydroisoquinolin-8-yl)ethanesulfonamide;
and pharmaceutically acceptable salts thereof.

11. A compound according to claim 1, selected from the group consisting of
(rac)-N-(4-(1-Methyl-2-oxo-1,2,3,4-tetrahydroquinolin-6-yl)-6,7-dihydro-5H-cyclopenta[c]pyridin-7-yl)propionamide;
(−)-N-(4-(1-Methyl-2-oxo-1,2,3,4-tetrahydroquinolin-6-yl)-6,7-dihydro-5H-cyclopenta[c]pyridin-7-yl)propionamide;
(+)-N-(4-(1-Methyl-2-oxo-1,2,3,4-tetrahydroquinolin-6-yl)-6,7-dihydro-5H-cyclopenta[c]pyridin-7-yl)propionamide;
(R)—N-(4-(1-Methyl-2-oxo-1,2,3,4-tetrahydroquinolin-6-yl)-6,7-dihydro-5H-cyclopenta[c]pyridin-7-yl)propionamide;
(S)—N-(4-(1-Methyl-2-oxo-1,2,3,4-tetrahydroquinolin-6-yl)-6,7-dihydro-5H-cyclopenta[c]pyridin-7-yl)propionamide; (rac)-N-(4-(1-Methyl-2-oxo-1,2,3,4-tetrahydroquinolin-6-yl)-6,7-dihydro-5H-cyclopenta[c]pyridin-7-yl)ethanesulfonamide;
{2-[5-(1-Methyl-2-oxo-1,2,3,4-tetrahydro-quinolin-6-yl)-3,4-dihydro-2H-[1,7]naphthyridin-1-yl]-ethyl}-carbamic acid tert-butyl ester;
6-[1-(2-Amino-ethyl)-1,2,3,4-tetrahydro-[1,7]naphthyridin-5-yl]-1-methyl-3,4-dihydro-1H-quinolin-2-one hydrochloride;
N-{2-[5-(1-Methyl-2-oxo-1,2,3,4-tetrahydro-quinolin-6-yl)-3,4-dihydro-2H-[1,7]naphthyridin-1-yl]-ethyl}-propionamide;
N-(2-(5-(1-Methyl-2-oxo-1,2,3,4-tetrahydroquinolin-6-yl)-3,4-dihydro-1,7-naphthyridin-1(2H)-yl)ethyl) ethanesulfonamide;
and pharmaceutically acceptable salts thereof.

12. A compound according to claim 1, selected from the group consisting of
- (2R,S)-2-Hydroxy-N-((4R,S)-4-(1-methyl-2-oxo-1,2,3,4-tetrahydroquinolin-6-yl)-5,6,7,8-tetrahydroisoquinolin-8-yl)propanamide;
- (2R)-2-Hydroxy-N-((4R,S)-4-(1-methyl-2-oxo-1,2,3,4-tetrahydroquinolin-6-yl)-5,6,7,8-tetrahydroisoquinolin-8-yl)propanamide;
- (2S)-2-Hydroxy-N-((4R,S)-4-(1-methyl-2-oxo-1,2,3,4-tetrahydroquinolin-6-yl)-5,6,7,8-tetrahydroisoquinolin-8-yl)propanamide;
- (+)-(2R)-2-Hydroxy-N-((4R or 4S)-4-(1-methyl-2-oxo-1,2,3,4-tetrahydroquinolin-6-yl)-5,6,7,8-tetrahydroisoquinolin-8-yl)propanamide;
- (−)-(2R)-2-Hydroxy-N-((4S or 4R)-4-(1-methyl-2-oxo-1,2,3,4-tetrahydroquinolin-6-yl)-5,6,7,8-tetrahydroisoquinolin-8-yl)propanamide;
- (−)-(2S)-2-Hydroxy-N-((4S or 4R)-4-(1-methyl-2-oxo-1,2,3,4-tetrahydroquinolin-6-yl)-5,6,7,8-tetrahydroisoquinolin-8-yl)propanamide;
- (+)-(2S)-2-Hydroxy-N-((4R or 4S)-4-(1-methyl-2-oxo-1,2,3,4-tetrahydroquinolin-6-yl)-5,6,7,8-tetrahydroisoquinolin-8-yl)propanamide;

and pharmaceutically acceptable salts thereof.

13. A compound according to claim 1, selected from the group consisting of
- (rac)-N-[4-(8-Chloro-1-methyl-2-oxo-1,2,3,4-tetrahydro-quinolin-6-yl)-5,6,7,8-tetrahydro-isoquinolin-8-yl]-propionamide;
- (rac)-Ethanesulfonic acid [4-(8-fluoro-1-methyl-2-oxo-1,2,3,4-tetrahydro-quinolin-6-yl)-5,6,7,8-tetrahydro-isoquinolin-8-yl]-amide;
- (rac)-Ethanesulfonic acid [4-(8-chloro-1-methyl-2-oxo-1,2,3,4-tetrahydro-quinolin-6-yl)-5,6,7,8-tetrahydro-isoquinolin-8-yl]-amide;
- (+)-Ethanesulfonic acid [(R or S)-4-(8-chloro-1-methyl-2-oxo-1,2,3,4-tetrahydro-quinolin-6-yl)-5,6,7,8-tetrahydro-isoquinolin-8-yl]-amide;
- (−)-Ethanesulfonic acid [(S or R)-4-(8-chloro-1-methyl-2-oxo-1,2,3,4-tetrahydro-quinolin-6-yl)-5,6,7,8-tetrahydro-isoquinolin-8-yl]-amide;
- (−)-N—[(S or R)-4-(8-Chloro-1-methyl-2-oxo-1,2,3,4-tetrahydro-quinolin-6-yl)-5,6,7,8-tetrahydro-isoquinolin-8-yl]-propionamide;
- (+)-N—[(R or S)-4-(8-Chloro-1-methyl-2-oxo-1,2,3,4-tetrahydro-quinolin-6-yl)-5,6,7,8-tetrahydro-isoquinolin-8-yl]-propionamide;

and pharmaceutically acceptable salts thereof.

14. A compound according to claim 1, selected from the group consisting of
- (+)-N-[(7S,8R or 7R,8S)-7-Methyl-4-(1-methyl-2-oxo-1,2,3,4-tetrahydro-quinolin-6-yl)-5,6,7,8-tetrahydro-isoquinolin-8-yl]-propionamide;
- (−)-N-[(7S,8S or 7R,8R)-7-Methyl-4-(1-methyl-2-oxo-1,2,3,4-tetrahydro-quinolin-6-yl)-5,6,7,8-tetrahydro-isoquinolin-8-yl]-propionamide;
- (−)-N-[(7R,8S or 7S,8R)-7-Methyl-4-(1-methyl-2-oxo-1,2,3,4-tetrahydro-quinolin-6-yl)-5,6,7,8-tetrahydro-isoquinolin-8-yl]-propionamide;
- (+)-N-[(7R,8R or 7S,8S)-7-Methyl-4-(1-methyl-2-oxo-1,2,3,4-tetrahydro-quinolin-6-yl)-5,6,7,8-tetrahydro-isoquinolin-8-yl]-propionamide;

and pharmaceutically acceptable salts thereof.

15. A compound according to claim 1, selected from the group consisting of
- (rac)-N-(4-(8-Chloro-1-methyl-2-oxo-1,2,3,4-tetrahydro-quinolin-6-yl)-6,7-dihydro-5H-cyclopenta[c]pyridin-7-yl)propionamide;
- (−)-(S or R)—N-(4-(8-Chloro-1-methyl-2-oxo-1,2,3,4-tetrahydroquinolin-6-yl)-6,7-dihydro-5H-cyclopenta[c]pyridin-7-yl)propionamide;
- (+)-(R or S)—N-(4-(8-Chloro-1-methyl-2-oxo-1,2,3,4-tetrahydroquinolin-6-yl)-6,7-dihydro-5H-cyclopenta[c]pyridin-7-yl)propionamide;
- 3-Chloro-pyridine-2-carboxylic acid [(R)-4-(1-methyl-2-oxo-1,2,3,4-tetrahydro-quinolin-6-yl)-5,6,7,8-tetrahydro-isoquinolin-8-yl]-amide;
- N—[(R)-4-(1-Methyl-2-oxo-1,2,3,4-tetrahydro-quinolin-6-yl)-5,6,7,8-tetrahydro-isoquinolin-8-yl]-acetamide;
- Cyclopropanecarboxylic acid [(R)-4-(1-methyl-2-oxo-1,2,3,4-tetrahydro-quinolin-6-yl)-5,6,7,8-tetrahydro-isoquinolin-8-yl]-amide;
- N—[(R)-4-(1-Methyl-2-oxo-1,2,3,4-tetrahydro-quinolin-6-yl)-5,6,7,8-tetrahydro-isoquinolin-8-yl]-methanesulfonamide;
- Cyclopropanesulfonic acid [(R)-4-(1-methyl-2-oxo-1,2,3,4-tetrahydro-quinolin-6-yl)-5,6,7,8-tetrahydro-isoquinolin-8-yl]-amide;
- N-[4-(1-Methyl-2-oxo-1,2,3,4-tetrahydro-quinolin-6-yl)-5,6-dihydro-isoquinolin-8-yl]-propionamide;
- (+)-(R)—N-(4-(1-Methyl-2-oxo-1,2,3,4-tetrahydroquinolin-6-yl)-5,6,7,8-tetrahydroisoquinolin-8-yl)propionamide;

and pharmaceutically acceptable salts thereof.

16. A compound according to claim 1, selected from the group consisting of
- (+)-N-(4-(1-Methyl-2-oxo-1,2,3,4-tetrahydroquinolin-6-yl)-5,6,7,8-tetrahydroisoquinolin-8-yl)propionamide;
- (+)-N-(4-(1-Methyl-2-oxo-1,2,3,4-tetrahydroquinolin-6-yl)-5,6,7,8-tetrahydroisoquinolin-8-yl)ethanesulfonamide;
- (+)-N-(4-(1-Methyl-2-oxo-1,2,3,4-tetrahydroquinolin-6-yl)-6,7-dihydro-5H-cyclopenta[c]pyridin-7-yl)propionamide;
- (rac)-N-(4-(1-Methyl-2-oxo-1,2,3,4-tetrahydroquinolin-6-yl)-6,7-dihydro-5H-cyclopenta[c]pyridin-7-yl)ethanesulfonamide;
- N-{2-[5-(1-Methyl-2-oxo-1,2,3,4-tetrahydro-quinolin-6-yl)-3,4-dihydro-2H-[1,7]naphthyridin-1-yl]-ethyl}-propionamide;

and pharmaceutically acceptable salts thereof.

17. A compound according to claim 1, selected from the group consisting of
- (+)-N—[(R or S)-4-(8-Chloro-1-methyl-2-oxo-1,2,3,4-tetrahydro-quinolin-6-yl)-5,6,7,8-tetrahydro-isoquinolin-8-yl]-propionamide;
- (+)-N-[(7S,8R or 7R,8S)-7-Methyl-4-(1-methyl-2-oxo-1,2,3,4-tetrahydro-quinolin-6-yl)-5,6,7,8-tetrahydro-isoquinolin-8-yl]-propionamide;
- (+)-N-[(7S,8S or 7R,8R)-7-Fluoro-4-(1-methyl-2-oxo-1,2,3,4-tetrahydro-quinolin-6-yl)-5,6,7,8-tetrahydro-isoquinolin-8-yl]-propionamide;
- (+)-(R or S)—N-(4-(8-Chloro-1-methyl-2-oxo-1,2,3,4-tetrahydroquinolin-6-yl)-6,7-dihydro-5H-cyclopenta[c]pyridin-7-yl)propionamide;
- 3-Chloro-pyridine-2-carboxylic acid [(R)-4-(1-methyl-2-oxo-1,2,3,4-tetrahydro-quinolin-6-yl)-5,6,7,8-tetrahydro-isoquinolin-8-yl]-amide;
- N—[(R)-4-(1-Methyl-2-oxo-1,2,3,4-tetrahydro-quinolin-6-yl)-5,6,7,8-tetrahydro-isoquinolin-8-yl]-acetamide;

(+)-(R)—N-(4-(1-Methyl-2-oxo-1,2,3,4-tetrahydroquinolin-6-yl)-5,6,7,8-tetrahydroisoquinolin-8-yl)propionamide;

and pharmaceutically acceptable salts thereof.

18. A compound according to claim 1, wherein the compound is (+)-(S or R)—N-(4-(1-Methyl-2-oxo-1,2,3,4-tetrahydroquinolin-6-yl)-5,6,7,8-tetrahydroisoquinolin-8-yl) propionamide or a pharmaceutically acceptable salt thereof.

19. A compound according to claim 1, wherein the compound is (+)-(R)—N-(4-(1-Methyl-2-oxo-1,2,3,4-tetrahydroquinolin-6-yl)-5,6,7,8-tetrahydroisoquinolin-8-yl)propionamide or a pharmaceutically acceptable salt thereof.

20. A pharmaceutical composition comprising a compound according to claim 1 and a therapeutically inert carrier.

21. A pharmaceutical composition according to claim 20, wherein said compound is (+)-(R)—N-(4-(1-Methyl-2-oxo-1,2,3,4-tetrahydroquinolin-6-yl)-5,6,7,8-tetrahydroisoquinolin-8-yl)propionamide or a pharmaceutically acceptable salt thereof.

* * * * *